US00RE46185E

(19) United States
(12) Reissued Patent
Mehi et al.

(10) Patent Number: US RE46,185 E
(45) Date of Reissued Patent: Oct. 25, 2016

(54) HIGH FREQUENCY ARRAY ULTRASOUND SYSTEM

(71) Applicant: FUJIFILM SonoSite, Inc., Bothell, WA (US)

(72) Inventors: James Mehi, Thornhill (CA); Ronald E. Daigle, Redmond, WA (US); Laurence C. Brasfield, Mercer Island, WA (US); Brian Starkoski, Toronto (CA); Jerrold Wen, Toronto (CA); Kai Wen Liu, North York (CA); Lauren S. Pflugrath, Seattle, WA (US); F. Stuart Foster, Toronto (CA); Desmond Hirson, Thornhill (CA)

(73) Assignee: FUJIFILM SonoSite, Inc., Bothell, WA (US)

(21) Appl. No.: 13/789,539

(22) Filed: Mar. 7, 2013

Related U.S. Patent Documents

Reissue of:
(64) Patent No.: 7,901,358
Issued: Mar. 8, 2011
Appl. No.: 11/592,741
Filed: Nov. 2, 2006

U.S. Applications:
(60) Provisional application No. 60/733,091, filed on Nov. 2, 2005, provisional application No. 60/733,089, filed on Nov. 2, 2005.

(51) Int. Cl.
*A61B 8/00* (2006.01)
*G01S 7/52* (2006.01)
(Continued)

(52) U.S. Cl.
CPC ..... *G01S 7/52095* (2013.01); *A61B 8/56* (2013.01); *A61B 8/565* (2013.01); *G01S 7/52017* (2013.01);
(Continued)

(58) Field of Classification Search
USPC ..... 600/447; 702/75
See application file for complete search history.

(56) References Cited

U.S. PATENT DOCUMENTS 2,205,169 A 5/1937 Hallman
3,922,572 A 11/1975 Cook et al.
(Continued)

FOREIGN PATENT DOCUMENTS

DE 4142372 6/1993
DE 42 26 865 A1 3/1994
(Continued)

OTHER PUBLICATIONS

Canadian Intellectual Property Office, Office Action, CA Patent Application 2,628,100, mailed Dec. 10, 2014, 3 pages.
(Continued)

*Primary Examiner* — Angela M Lie
(74) *Attorney, Agent, or Firm* — Perkins Coie LLP

(57) ABSTRACT

A system for acquiring an ultrasound signal comprises a signal processing unit adapted for acquiring a received ultrasound signal from an ultrasound transducer having a plurality of elements. The system is adapted to receive ultrasound signals having a frequency of at least 20 megahertz (MHz) with a transducer having a field of view of at least 5.0 millimeters (mm) at a frame rate of at least 20 frames per second (fps). The signal processing can further produce an ultrasound image from the acquired ultrasound signal. The transducer can be a linear array transducer, a phased array transducer, a two-dimensional (2-D) array transducer, or a curved array transducer.

74 Claims, 56 Drawing Sheets

Exemplary Operating Environment

(51) Int. Cl.

| | |
|---|---|
| ***G01S 15/89*** | (2006.01) |
| ***G10K 11/34*** | (2006.01) |
| *G01S 7/526* | (2006.01) |
| *G01S 7/524* | (2006.01) |

(52) U.S. Cl.

CPC ..... *G01S 7/52034* (2013.01); *G01S 7/52088* (2013.01); *G01S 15/8915* (2013.01); *G01S 15/8927* (2013.01); *G01S 15/8956* (2013.01); *G01S 15/8997* (2013.01); *G10K 11/341* (2013.01); *G10K 11/346* (2013.01); *G01S 7/5202* (2013.01); *G01S 7/524* (2013.01); *G01S 7/526* (2013.01); *G01S 15/8959* (2013.01)

(56) References Cited

U.S. PATENT DOCUMENTS

| | | | |
|---|---|---|---|
| 4,217,684 | A | 8/1980 | Brisken et al. |
| 4,360,007 | A | 11/1982 | Levy et al. |
| 4,385,255 | A | 5/1983 | Yamaguchi et al. |
| 4,398,325 | A | 8/1983 | Piaget et al. |
| 4,543,829 | A | 10/1985 | Lerch |
| 4,617,707 | A | 10/1986 | Mohaupt et al. |
| 4,802,099 | A | 1/1989 | Logue |
| 4,809,184 | A | 2/1989 | O'Donnell et al. |
| 4,841,977 | A | 6/1989 | Griffith et al. |
| 4,945,155 | A | 7/1990 | Fagerburg et al. |
| 5,014,710 | A | 5/1991 | Maslak et al. |
| 5,045,746 | A | 9/1991 | Wersing et al. |
| 5,065,068 | A | 11/1991 | Oakley |
| 5,095,692 | A | 3/1992 | Scheufeld et al. |
| 5,123,415 | A | 6/1992 | Daigle |
| 5,160,870 | A | 11/1992 | Carson et al. |
| 5,186,177 | A | 2/1993 | O'Donnell et al. |
| 5,203,335 | A | 4/1993 | Noujaim et al. |
| 5,311,095 | A | 5/1994 | Smith et al. |
| 5,318,033 | A | 6/1994 | Savord |
| 5,325,860 | A | 7/1994 | Seward et al. |
| 5,329,496 | A | 7/1994 | Smith |
| 5,345,426 | A | 9/1994 | Lipschutz |
| 5,345,940 | A | 9/1994 | Seward et al. |
| 5,360,007 | A | 11/1994 | Shinomura et al. |
| 5,368,037 | A | 11/1994 | Eberle et al. |
| 5,369,624 | A | 11/1994 | Fukukita et al. |
| 5,371,717 | A | 12/1994 | Bolorforosh |
| 5,388,079 | A | 2/1995 | Kim et al. |
| 5,390,674 | A | 2/1995 | Robinson et al. |
| 5,392,259 | A | 2/1995 | Bolorforosh |
| 5,406,163 | A | 4/1995 | Carson et al. |
| 5,410,516 | A | 4/1995 | Uhlendorf et al. |
| 5,415,175 | A | 5/1995 | Hanafy et al. |
| 5,434,827 | A | 7/1995 | Bolorforosh |
| RE35,011 | E | 8/1995 | Wersing et al. |
| 5,438,554 | A | 8/1995 | Seyed-Bolorforosh et al. |
| 5,438,998 | A | 8/1995 | Hanafy |
| 5,445,155 | A | 8/1995 | Sieben |
| 5,453,575 | A | 9/1995 | O'Donnell et al. |
| 5,456,259 | A | 10/1995 | Barlow et al. |
| 5,460,181 | A | 10/1995 | Seyed-Bolorforosh |
| 5,465,725 | A | 11/1995 | Seyed-Bolorforosh |
| 5,505,088 | A | 4/1996 | Chandraratna et al. |
| 5,522,391 | A | 6/1996 | Beaudin et al. |
| 5,544,655 | A | 8/1996 | Daigle |
| 5,548,564 | A | 8/1996 | Smith |
| 5,553,035 | A | 9/1996 | Seyed-Bolorforosh et al. |
| 5,573,001 | A | 11/1996 | Petrofsky et al. |
| 5,577,506 | A | 11/1996 | Dias |
| 5,582,177 | A | 12/1996 | Hanafy et al. |
| 5,603,324 | A | 2/1997 | Oppelt et al. |
| 5,603,327 | A | 2/1997 | Eberle et al. |
| 5,629,865 | A | 5/1997 | Roth |
| 5,653,236 | A | 8/1997 | Miller |
| 5,655,276 | A | 8/1997 | Pattanayak et al. |
| 5,667,373 | A | 9/1997 | Wright et al. |
| 5,704,105 | A | 1/1998 | Venkataramani et al. |
| 5,704,361 | A | 1/1998 | Seward et al. |
| 5,706,819 | A | 1/1998 | Hwang et al. |
| 5,713,363 | A | 2/1998 | Seward et al. |
| 5,724,312 | A | 3/1998 | Oppelt |
| 5,743,855 | A | 4/1998 | Hanafy et al. |
| 5,744,898 | A | 4/1998 | Smith et al. |
| 5,759,791 | A | 6/1998 | Kuhajda et al. |
| 5,779,644 | A | 7/1998 | Eberle et al. |
| 5,792,058 | A | 8/1998 | Lee et al. |
| 5,795,297 | A | 8/1998 | Daigle |
| 5,796,207 | A | 8/1998 | Safari et al. |
| 5,797,847 | A | 8/1998 | Miller et al. |
| 5,834,880 | A | 11/1998 | Venkataramani et al. |
| 5,844,139 | A | 12/1998 | Miller et al. |
| 5,857,974 | A | 1/1999 | Eberle et al. |
| 5,865,749 | A | 2/1999 | Doten et al. |
| 5,879,303 | A | 3/1999 | Averkiou et al. |
| 5,895,855 | A | 4/1999 | Ishikawa et al. |
| 5,897,501 | A | 4/1999 | Wildes et al. |
| 5,905,692 | A | 5/1999 | Dolazza et al. |
| 5,906,580 | A | 5/1999 | Kline-Schoder et al. |
| 5,938,612 | A | 8/1999 | Kline-Schoder et al. |
| 5,938,615 | A | 8/1999 | Eberle et al. |
| 5,940,123 | A | 8/1999 | Daigle et al. |
| 5,970,025 | A | 10/1999 | Cole et al. |
| 5,976,090 | A | 11/1999 | Hanafy et al. |
| 5,977,691 | A | 11/1999 | Stephens et al. |
| 6,001,062 | A | 12/1999 | Masters |
| 6,029,116 | A | 2/2000 | Wright et al. |
| 6,034,922 | A | 3/2000 | Uhlendorf et al. |
| 6,039,693 | A | 3/2000 | Seward et al. |
| 6,049,159 | A | 4/2000 | Barthe et al. |
| 6,049,958 | A | 4/2000 | Eberle et al. |
| 6,050,945 | A | 4/2000 | Peterson et al. |
| 6,063,034 | A | 5/2000 | Doten et al. |
| 6,064,628 | A | 5/2000 | Uhlendorf et al. |
| 6,073,045 | A | 6/2000 | Dyson et al. |
| 6,074,346 | A | 6/2000 | Oppelt |
| 6,083,164 | A | 7/2000 | Oppelt et al. |
| 6,099,475 | A | 8/2000 | Seward et al. |
| 6,110,116 | A | 8/2000 | Wright et al. |
| 6,123,673 | A | 9/2000 | Eberle et al. |
| 6,128,958 | A | 10/2000 | Cain et al. |
| 6,129,672 | A | 10/2000 | Seward et al. |
| 6,129,677 | A | 10/2000 | Sohma et al. |
| 6,135,971 | A | 10/2000 | Hutchinson et al. |
| 6,183,578 | B1 | 2/2001 | Ritter et al. |
| 6,193,662 | B1 | 2/2001 | Hwang |
| 6,221,017 | B1 | 4/2001 | Uhlendorf et al. |
| 6,235,024 | B1 | 5/2001 | Tu |
| 6,236,144 | B1 | 5/2001 | Millar et al. |
| 6,238,481 | B1 | 5/2001 | Yamashita et al. |
| 6,251,073 | B1 | 6/2001 | Imran et al. |
| 6,255,761 | B1 | 7/2001 | Benjamin |
| 6,258,034 | B1 | 7/2001 | Hanafy |
| 6,262,749 | B1 | 7/2001 | Finger et al. |
| 6,278,224 | B1 | 8/2001 | Sawada et al. |
| 6,283,920 | B1 | 9/2001 | Eberle et al. |
| 6,306,096 | B1 | 10/2001 | Seward et al. |
| 6,315,725 | B1 | 11/2001 | Masters |
| 6,322,505 | B1 | 11/2001 | Hossack et al. |
| 6,350,238 | B1 | 2/2002 | Olstad et al. |
| 6,363,033 | B1 | 3/2002 | Cole et al. |
| 6,403,396 | B1 | 6/2002 | Gudesen et al. |
| 6,417,857 | B2 | 7/2002 | Finger et al. |
| 6,437,487 | B1 | 8/2002 | Mohr, III et al. |
| 6,443,899 | B2 | 9/2002 | Uhlendorf et al. |
| 6,453,526 | B2 | 9/2002 | Lorraine et al. |
| 6,457,365 | B1 | 10/2002 | Stephens et al. |
| 6,483,225 | B1 | 11/2002 | Spigelmyer |
| 6,490,228 | B2 | 12/2002 | Killam |
| 6,492,762 | B1 | 12/2002 | Pant et al. |
| 6,497,664 | B1 | 12/2002 | Randall et al. |
| 6,503,204 | B1 | 1/2003 | Sumanaweera et al. |
| 6,530,887 | B1 | 3/2003 | Gilbert et al. |
| 6,544,180 | B1 | 4/2003 | Doten et al. |
| 6,547,731 | B1 | 4/2003 | Coleman et al. |
| 6,558,323 | B2 | 5/2003 | Wakabayashi et al. |

(56) References Cited

U.S. PATENT DOCUMENTS 6,558,326 B2 5/2003 Pelissier et al.
6,586,702 B2 7/2003 Wiener-Avnear et al.
6,608,371 B2 8/2003 Kurashima et al.
6,612,989 B1 9/2003 Brock-Fisher
6,618,916 B1 9/2003 Eberle et al.
6,626,838 B2 9/2003 Doten et al.
6,635,019 B2 10/2003 Davidsen
6,641,540 B2 11/2003 Fleischman et al.
6,650,264 B1 11/2003 Chan et al.
6,656,124 B2 12/2003 Flesch et al.
6,664,717 B1 12/2003 Mohr, III et al.
6,673,018 B2 1/2004 Friedman
6,676,606 B2 1/2004 Simpson et al.
6,679,845 B2 1/2004 Ritter et al.
6,685,644 B2 2/2004 Seo et al.
6,685,657 B2 2/2004 Jones
6,695,783 B2 2/2004 Henderson et al.
6,705,992 B2 3/2004 Gatzke
6,740,037 B1 5/2004 Schoenfeld
6,757,948 B2 7/2004 Ptchelintsev et al.
6,759,791 B2 7/2004 Hatangadi et al.
6,761,688 B1 7/2004 Mohr, III et al.
6,761,697 B2 7/2004 Rubinstenn et al.
6,780,157 B2 8/2004 Stephens et al.
6,784,600 B2 8/2004 Klee et al.
6,787,974 B2 9/2004 Fjield et al.
6,798,717 B2 9/2004 Wiener-Avnear et al.
6,806,622 B1 10/2004 Schmidt et al.
6,806,623 B2 10/2004 Petersen et al.
6,821,253 B2 11/2004 Wakabayashi et al.
6,822,189 B2 11/2004 Hong et al.
6,822,374 B1 11/2004 Smith et al.
6,822,376 B2 11/2004 Baumgartner
6,831,394 B2 12/2004 Baumgartner et al.
6,837,855 B1 1/2005 Puech
6,851,392 B2 2/2005 Zan et al.
6,873,090 B2 3/2005 Shiraishi et al.
6,875,178 B2 4/2005 Phelps et al.
6,891,311 B2 5/2005 Phelps et al.
6,894,426 B2 5/2005 Shimizu
6,899,682 B2 5/2005 Eberle et al.
6,919,668 B2 7/2005 Nagahara et al.
6,929,608 B1 8/2005 Hutchinson et al.
6,936,009 B2 8/2005 Venkataramani et al.
6,949,071 B1 9/2005 Saied et al.
6,962,567 B2 11/2005 Eberle et al.
6,974,417 B2 12/2005 Lockwood et al.
6,994,674 B2 2/2006 Sheljaskow et al.
7,017,245 B2 3/2006 Baumgartner et al.
7,052,460 B2 5/2006 Liu et al.
7,052,462 B2 5/2006 Fukuda et al.
7,087,970 B2 8/2006 Nakamura
7,091,125 B2 8/2006 Werner et al.
7,134,198 B2 11/2006 Nakatani et al.
7,139,676 B2 11/2006 Barford
7,148,607 B2 12/2006 Sato
7,148,608 B2 12/2006 Baumgartner et al.
7,156,812 B2 1/2007 Seward et al.
7,156,938 B2 1/2007 Baumgartner et al.
7,208,717 B2 4/2007 Partain et al.
7,230,368 B2 6/2007 Lukacs et al.
7,249,513 B1 7/2007 Zipparo et al.
7,255,678 B2 8/2007 Mehi et al.
7,316,059 B2 1/2008 Sato
7,377,900 B2 5/2008 Vitek et al.
7,391,872 B2 6/2008 Pompei
7,424,771 B2 9/2008 Shiraishi et al.
7,451,650 B2 11/2008 Halvorsrod et al.
7,454,820 B2 11/2008 Nakamura
7,459,836 B2 12/2008 Scott
7,489,066 B2 2/2009 Scott et al.
7,518,290 B2 4/2009 Frey
7,901,358 B2 3/2011 Mehi et al.
8,002,708 B2 * 8/2011 Shah ..... G01S 7/52023 367/123
2001/0007940 A1 7/2001 Tu et al.
2001/0041842 A1 11/2001 Eberle et al.
2002/0000763 A1 1/2002 Jones
2002/0050169 A1 5/2002 Ritter et al.
2002/0058873 A1 5/2002 Seward et al.
2002/0077551 A1 6/2002 Fleischman et al.
2002/0130590 A1 9/2002 Shiraishi et al.
2002/0157472 A1 10/2002 Stephens et al.
2002/0173720 A1 11/2002 Seo et al.
2003/0009873 A1 1/2003 Hatangadi et al.
2003/0015037 A1 1/2003 Stephens et al.
2003/0036702 A1 2/2003 Davidsen
2003/0067249 A1 4/2003 Lockwood et al.
2003/0073906 A1 4/2003 Flesch et al.
2003/0127949 A1 7/2003 Nagahara et al.
2003/0173870 A1 9/2003 Hsu
2003/0187356 A1 10/2003 Wakabayashi et al.
2003/0189391 A1 10/2003 Shimizu
2003/0205947 A1 11/2003 Klee et al.
2004/0000841 A1 1/2004 Phelps et al.
2004/0002656 A1 1/2004 Sheljaskow et al.
2004/0011134 A1 1/2004 Sato
2004/0040740 A1 3/2004 Nakatani et al.
2004/0054289 A1 3/2004 Eberle et al.
2004/0068191 A1 4/2004 Seward et al.
2004/0071320 A1 4/2004 Pfister
2004/0082858 A1 4/2004 Fukuda et al.
2004/0111026 A1 6/2004 Schoenfeld
2004/0122319 A1 6/2004 Mehi et al.
2004/0176784 A1 9/2004 Okada
2004/0236219 A1 11/2004 Liu et al.
2005/0039323 A1 2/2005 Sheljaskow
2005/0046030 A1 3/2005 Nakamura
2005/0089205 A1 4/2005 Kapur et al.
2005/0099096 A1 5/2005 Baumgartner et al.
2005/0099097 A1 5/2005 Baumgartner et al.
2005/0124894 A1 6/2005 Puech
2005/0126490 A1 6/2005 Hsieh et al.
2005/0156490 A1 7/2005 Shiraishi et al.
2005/0197543 A1 9/2005 Zan et al.
2005/0197574 A1 9/2005 Eberle et al.
2005/0203402 A1 9/2005 Angelsen et al.
2005/0240102 A1 10/2005 Rachlin et al.
2005/0251043 A1 11/2005 Saied et al.
2005/0251232 A1 11/2005 Hartley et al.
2005/0272183 A1 12/2005 Lukacs et al.
2006/0058681 A1 3/2006 Eberle et al.
2006/0078501 A1 4/2006 Goertz et al.
2006/0241446 A1 10/2006 White et al.
2006/0241461 A1 10/2006 White et al.
2007/0016071 A1 1/2007 Eberle et al.
2007/0059247 A1 3/2007 Lindner et al.
2007/0075063 A1 4/2007 Wilbanks et al.
2007/0078347 A1 4/2007 Srinivasan et al.
2007/0167815 A1 7/2007 Jacobsen et al.
2007/0182287 A1 8/2007 Lukacs et al.
2007/0200460 A1 8/2007 Scott
2007/0205698 A1 9/2007 Chaggares et al.
2007/0222339 A1 9/2007 Lukacs et al.
2008/0007142 A1 1/2008 Toda
2008/0015438 A1 1/2008 Mehi et al.
2008/0273424 A1 11/2008 Wodnicki et al.
2009/0108708 A1 4/2009 Jiang et al.
2009/0240152 A1 9/2009 Angelsen et al.
2009/0298299 A1 12/2009 Cain et al.

FOREIGN PATENT DOCUMENTS

DE 4226865 3/1994
DE 10336101 4/2004
EP 0227926 7/1987
EP 0627635 7/1991
EP 0467690 1/1992
EP 0627635 12/1994
EP 0629992 12/1994
EP 0629994 12/1994
EP 0779108 6/1997
EP 1227525 7/2002
EP 1318551 6/2003

(56) References Cited

FOREIGN PATENT DOCUMENTS

| | | | |
|---|---|---|---|
| EP | 1382301 | | 1/2004 |
| FR | 2828056 | | 1/2003 |
| JP | 56070000 | | 6/1981 |
| JP | 06014928 | A | 1/1994 |
| JP | 08070404 | A | 3/1996 |
| JP | 200480193 | | 3/2004 |
| JP | 2006502828 | A | 1/2006 |
| JP | 2006525837 | A | 11/2006 |
| WO | WO-9717018 | | 5/1997 |
| WO | WO-9934733 | | 7/1999 |
| WO | WO-9945582 | | 9/1999 |
| WO | WO-0152437 | | 7/2001 |
| WO | WO-0243593 | | 6/2002 |
| WO | WO-03040427 | | 5/2003 |
| WO | WO-2004007098 | | 1/2004 |
| WO | WO-2004099814 | | 11/2004 |
| WO | WO-2005104210 | | 11/2005 |
| WO | WO-2007029028 | | 3/2007 |
| WO | WO 2007/056104 | A2 | 5/2007 |
| WO | WO-2007056104 | | 5/2007 |
| WO | WO-2007067282 | | 6/2007 |

OTHER PUBLICATIONS

Japan Patent Office, Notice of Allowance, JP Patent Application 2013-204411, dated Jan. 5, 2015, 3 pages.

Brown, et al.; "A Digital Beamformer for High-Frequency Annular Arrays"; IEEE Transactions on Ultrasonics, Ferroelectrics, and Frequency Control; vol. 52, No. 8; Aug. 2005; pp. 1262-1269.

Hu, et al.; "FPGA Based Digital High Frequency Beamformers for Arrays"; 2004 IEEE Ultrasonics Symposium; pp. 1347-1350.

Brown, et al.; "Performance of a 50 MHz Annular Array Based Imaging System"; 2004 IEEE Ultrasonics Symposium; pp. 760-763.

Wu, et al.; "Design of an Analog Beamformer for Very High-Frequency Ultrasound Transducer Arrays"; Proceedings of SPIE; vol. 3982; 2000; pp. 142-149.

International Search Report dated Jun. 5, 2007.

PCT/US2006/042891, Mehi et al., Nov. 2, 2006, International Search Report, May 6, 2007.

PCT/US2006/042891, Mehi et al., Nov. 2, 2006, Written Opinion, May 6, 2007.

PCT/US2006/042891, Mehi et al., Nov. 2, 2006, International Preliminary Report on Patentability, May 6, 2008.

06827417.4, Mehi et al., Nov. 2, 2006, Examination Report, Sep. 19, 2008.

06827417.4, Mehi et al., Nov. 2, 2006, Amendments Received Before Examination, Jul. 28, 2008.

06827417.4, Mehi et al., Nov. 2, 2006, Amendment to Claims, Jun. 17, 2008.

Brown J. et al., Performance of a 50MHZ annular array based imaging system, *Ultrasonics Symposium, 2004 IEEE* Montreal, Canada Aug. 23-27, 2004, Piscataway, NJ, USA IEEE, Aug. 23, 2004, pp. 760-7637.

Cannata, J. M. et al., "Development of High Frequency (35 MHz) linear ultrasonic array 2-2 composite elements", *Ultrasonics Symposium, 2004 IEEE* Montreal, Canada Aug. 23-27, 2004, Piscataway, NJ, USA IEEE, Aug. 23, 2004, pp. 894-897.

Chang-Hong Hu et al., "An FPGA Based Digital High Frequency Beamformer for Arrays", *Ultrasonics Symposium, 2004 IEEE* Montreal, Canada Aug. 23-27, 2004, Piscataway, NJ, USA IEEE, Aug. 23, 2004, pp. 1347-1350.

Hu et al., "An FPGA Based Digital High Frequency Beamformer for Arrays", 8th Annual Fred S. Grodins Graduate Research Symposium, NIH Resource Center for Medical Ultrasound Transducer Technology, USC Los Angeles, CA, pp. 84-85.

McKeighen, R. E. "Design Guidelines for Medical Ultrasonic Arrays", *SPIE International Symposium on Medical Imaging,* Feb. 25, 1998, San Diego, CA.

Michau, et al., "Piezocomposite 30MHz array for medical imaging: design challenges and performances evaluation of a 128 elements array", *Ultrasonics Symposium, 2004 IEEE* Montreal, Canada Aug. 23-27, 2004, Piscataway, NJ, USA IEEE, Aug. 23, 2004, pp. 898-901.

Oralkan, et al., High-frequency CMUT arrays for high-resolution medical imaging, *Ultrasonics Symposium, 2004 IEEE* Montreal, Canada Aug. 23-27, 2004, Piscataway, NJ, USA IEEE, Aug. 23, 2004, pp. 399-402.

Ritter et al., "A 30-MHz Piezo-composite ultrasound array for medical imaging applications", IEEE Transactions on Ultrasonics, Ferroelectrics and Frequency Control, IEEE Inc. New York, US, vol. 49, No. 2 Feb. 2002, pp. 217-230.

Tutwiler, R. L. et al., "Design of a test system to characterize very high-frequency ultrasound transducer arrays", Proc SPIE Int Soc Opt Eng; Proceedings of SPIE—The International Society for Engineering 1999, Society of Photo-Optical Instrumentation Engineers, Bellingham, WA, USA vol. 3664, 1999, pp. 182-193.

U.S. Appl. No. 12/562,935, filed Sep. 18, 2009, Mehi et al.

U.S. Appl. No. 12/562,998, filed Sep. 18, 2009, Lukacs et al.

Bridal et al., "Milestones on the Road to Higher Resolution, Quantitative, and Functional Ultrasonic Imaging," *Proceedings of the IEEE* 91:1543-1561, 2003.

Brown et al., "In Vivo Assessment of Postnatal Murine Ocular Development by Ultrasound Biomicroscopy," *Current Eye Research* 30:45-51, 2005.

Brown et al., "Quantitation of Hemodynamic Function during Developmental Vascular Regression in the Mouse Eye," *Invest. Ophth. Vis. Sci.* 46:2231-2237, 2005.

Ergun et al., "Broadband Capacitive Micromachined Ultrasonic Transducers Ranging From 10kHz to 60MHz for Imaging Arrays and More," *IEEE Ultrasonics Symposium* 1039-1043, 2002.

Farlow et al., "Micromachining of a Piezocomposite Transducer Using a Copper Vapor Laser," *IEEE Transactions on Ultrasonics, Ferroelectrics, and Frequency Control* 48:639-640, 2001.

Goertz et al., "High Frequency Nonlinear B-Scan Imaging of Microbubble Contrast Agents," *IEEE Transactions on Ultrasonics, Ferroelectrics, and Frequency Control* 52:65-79, 2005.

Guess et al., "Cross-talk Paths in Array Transducers," *IEEE Ultrasonics Symposium* 1279-1282, 1995.

Herman et al., "Advanced-laser Processing of Photonic and Microelectronic Components at Photonics Research Ontario," *SPIE Proc.* 3618:240-250, 1999.

Jensen et al., "A Program for Simulating Ultrasound Systems," *Medical & Biological Engineering & Computing* 34:351-354, 1996.

Lerch et al., "Simulation of Piezoelectric Devices by Two-and Three-Dimensional Finite Elements," *IEEE Transactions on Ultrasonics, Ferroelectrics, and Frequency Control* 37:233-247, 1990.

Liu et al., "Interdigital Pair Bonding for High Frequency (20-50MHz) Ultrasonic Composite Transducers," *IEEE Transactions on Ultrasonics, Ferroelectrics, and Frequency Control* 48:299-306, 2001.

Lukacs et al., "Laser Micromachined High Frequency Ultrasonic Arrays," *IEEE Ultrasonics Symposium* 1209-1212, 1998.

Lukacs et al., "Single Element and Linear Array PZT Ultrasound Biomicroscopy Transducers," *IEEE Ultrasonics Symposium* 1709-1712, 1997.

Lukacs et al., "Single Element and Linear Array Transducer Design for Ultrasound Biomicroscopy," *SPIE* 3341:272-282, 1998.

Lukacs, "Single Element and Linear Arrays High Frequency Ultrasonic Transducers Using PZT Sol Gel Composites," Ph.D. Thesis, Queen's University, 1-165, 1999.

Oralkan et al., "Capacitive Micromachined Ultrasonic Transducers: Next-Generation Arrays for Acoustic Imaging?" *IEEE Trans. Ultrason. Ferroelectr. Freq. Control* 49: 1596-1610, 2002.

Roh et al., "Finite Element Analysis on Reduction of the Cross Talk in Ultrasonic Transducers," *Proceedings of SPIE* 4693:214-221, 2002.

Sherrit et al., "Field Dependence of the Complex Piezoelectric, Dielectric, and Elastic Constants of Motorola PZT 3203 HD Ceramic," *SPIE* 3040:99-109, 1997.

Snook et al., "Design of a 50 MHz Annular Array Using Fine-Grain Lead Titanate," *Proceedings of SPIE* 4687:91-98, 2002.

Wang et al., "Passive Materials for High Frequency Ultrasound Transducers," *SPIE* 3664:35-42, 1999.

Statement of Sale Prior to Apr. 2003.

* cited by examiner

Exemplary Operating Environment

REGION B

REGION A

LEFT SIDE OF FLEX
J1 BTH Connector on Flex

| Table sorted by BTH Pin | | | Table sorted across BTH Rows | | |
|---|---|---|---|---|---|
| BTH Pin | Array Channel | Flex Trace | BTH Pin | Array Channel | Flex Trace |
| 1 | G | G | 1 | G | G |
| 2 | G | G | 3 | 129 | 65L |
| 3 | 129 | 65L | 5 | 131 | 66L |
| 4 | 127 | 64L | 7 | G | G |
| 5 | 131 | 66L | 9 | 133 | 67L |
| 6 | 125 | 63L | 11 | 135 | 68L |
| 7 | G | G | 13 | G | G |
| 8 | G | G | 15 | 137 | 69L |
| 9 | 133 | 67L | 17 | 139 | 70L |
| 10 | 123 | 62L | 19 | 141 | 71L |
| 11 | 135 | 68L | 21 | G | G |
| 12 | 121 | 61L | 23 | 143 | 72L |
| 13 | G | G | 25 | 145 | 73L |
| 14 | G | G | 27 | G | G |
| 15 | 137 | 69L | 29 | 147 | 74L |
| 16 | 119 | 60L | 31 | 149 | 75L |
| 17 | 139 | 70L | 33 | 151 | 76L |
| 18 | 117 | 59L | 35 | G | G |
| 19 | 141 | 71L | 37 | 153 | 77L |
| 20 | 115 | 58L | 39 | 155 | 78L |
| 21 | G | G | 41 | G | G |
| 22 | G | G | 43 | 157 | 79L |
| 23 | 143 | 72L | 45 | 159 | 80L |
| 24 | 113 | 57L | 47 | 161 | 81L |
| 25 | 145 | 73L | 49 | G | G |
| 26 | 111 | 58L | 51 | 163 | 82L |
| 27 | G | G | 53 | 165 | 83L |
| 28 | G | G | 55 | G | G |
| 29 | 147 | 74L | 57 | 167 | 84L |
| 30 | 109 | 55L | 59 | 169 | 85L |
| 31 | 149 | 75L | 61 | 171 | 86L |
| 32 | 107 | 54L | 63 | G | G |

RIGHT SIDE OF FLEX
J3 BTH Connector on Flex

| Table sorted by BTH Pin | | | Table sorted across BTH Rows | | |
|---|---|---|---|---|---|
| BTH Pin | Array Channel | Flex Trace | BTH Pin | Array Channel | Flex Trace |
| 1 | G | G | 1 | G | G |
| 2 | G | G | 3 | 128 | 64R |
| 3 | 128 | 64R | 5 | 126 | 63R |
| 4 | 130 | 65R | 7 | G | G |
| 5 | 126 | 63R | 9 | 124 | 62R |
| 6 | 132 | 66R | 11 | 122 | 61R |
| 7 | G | G | 13 | G | G |
| 8 | G | G | 15 | 120 | 60R |
| 9 | 124 | 62R | 17 | 118 | 59R |
| 10 | 134 | 67R | 19 | 116 | 58R |
| 11 | 122 | 61R | 21 | G | G |
| 12 | 136 | 68R | 23 | 114 | 57R |
| 13 | G | G | 25 | 112 | 56R |
| 14 | G | G | 27 | G | G |
| 15 | 120 | 60R | 29 | 110 | 55R |
| 16 | 138 | 69R | 31 | 108 | 54R |
| 17 | 118 | 59R | 33 | 106 | 53R |
| 18 | 140 | 70R | 35 | G | G |
| 19 | 116 | 58R | 37 | 104 | 52R |
| 20 | 142 | 71R | 39 | 102 | 51R |
| 21 | G | G | 41 | G | G |
| 22 | G | G | 43 | 100 | 50R |
| 23 | 114 | 57R | 45 | 98 | 49R |
| 24 | 144 | 72R | 47 | 96 | 48R |
| 25 | 112 | 56R | 49 | G | G |
| 26 | 146 | 73R | 51 | 94 | 47R |
| 27 | G | G | 53 | 92 | 46R |
| 28 | G | G | 55 | G | G |
| 29 | 110 | 55R | 57 | 90 | 45R |
| 30 | 148 | 74R | 59 | 88 | 44R |
| 31 | 108 | 54R | 61 | 86 | 43R |
| 32 | 150 | 75R | 63 | G | G |

Cont. on Fig.12B2

FIG.12B

Cont. from Fig.12B1

| | | | | | | | | | | | |
|---|---|---|---|---|---|---|---|---|---|---|---|
| 33 | 151 | 76L | 65 | 173 | 87L | 33 | 106 | 53R | 65 | 84 | 42R |
| 34 | 105 | 53L | 67 | 175 | 88L | 34 | 152 | 76R | 67 | 82 | 41R |
| 35 | G | G | 69 | G | G | 35 | G | G | 69 | G | G |
| 36 | G | G | 71 | 177 | 89L | 36 | G | G | 71 | 80 | 40R |
| 37 | 153 | 77L | 73 | 179 | 90L | 37 | 104 | 52R | 73 | 78 | 39R |
| 38 | 103 | 52L | 75 | 181 | 91L | 38 | 154 | 77R | 75 | 76 | 38R |
| 39 | 155 | 78L | 7 | G | G | 39 | 102 | 51R | 7 | G | G |
| 40 | 101 | 51L | 79 | 183 | 92L | 40 | 156 | 78R | 79 | 74 | 37R |
| 41 | G | G | 81 | 185 | 93L | 41 | G | G | 81 | 72 | 36R |
| 42 | G | G | 83 | G | G | 42 | G | G | 83 | G | G |
| 43 | 157 | 77L | 85 | 187 | 94L | 43 | 100 | 50R | 85 | 70 | 35R |
| 44 | 99 | 52L | 87 | 189 | 95L | 44 | 158 | 79R | 87 | 68 | 34R |
| 45 | 159 | 78L | 89 | 191 | 96L | 45 | 98 | 49R | 89 | 66 | 33R |
| 46 | 97 | 51L | 91 | G | G | 46 | 160 | 80R | 91 | G | G |
| 47 | 161 | G | 93 | 193 | 97L | 47 | 96 | 48R | 93 | 64 | 32R |
| 48 | 95 | G | 95 | 195 | 98L | 48 | 162 | 81R | 95 | 62 | 31R |
| 49 | G | 79L | 97 | G | G | 49 | G | G | 97 | G | G |
| 50 | G | 50L | 99 | 197 | 99L | 50 | G | G | 99 | 60 | 30R |
| 51 | 163 | 80L | 101 | 199 | 100L | 51 | 94 | 47R | 101 | 58 | 29R |
| 52 | 93 | 49L | 103 | 201 | 101L | 52 | 164 | 82R | 103 | 56 | 28R |
| 53 | 165 | 81L | 105 | G | G | 53 | 92 | 46R | 105 | G | G |
| 54 | 91 | 48L | 107 | 203 | 102L | 54 | 166 | 83R | 107 | 54 | 27R |
| 55 | G | G | 109 | 205 | 103L | 55 | G | G | 109 | 52 | 26R |
| 56 | G | G | 111 | G | G | 56 | G | G | 111 | G | G |
| 57 | 167 | 84L | 113 | 207 | 104L | 57 | 90 | 45R | 113 | 50 | 25R |
| 58 | 89 | 45L | 115 | 209 | 105L | 58 | 168 | 84R | 115 | 48 | 24R |
| 59 | 169 | 85L | 117 | 211 | 106L | 59 | 88 | 44R | 117 | 46 | 23R |
| 60 | 87 | 44L | 119 | G | G | 60 | 170 | 85R | 119 | G | G |
| 61 | 171 | 86L | 121 | 213 | 107L | 61 | 86 | 43R | 121 | 44 | 22R |
| 62 | 85 | 43L | 123 | 215 | 108L | 62 | 172 | 86R | 123 | 42 | 21R |
| 63 | G | G | 125 | G | G | 63 | G | G | 125 | G | G |
| 64 | G | G | 127 | 217 | 109L | 64 | G | G | 127 | 40 | 20R |

Cont. on Fig.12B3

FIG.12B-2

Cont. from Fig.12B2

| LEFT SIDE OF FLEX J1 BTH Connector on Flex | | | | | | RIGHT SIDE OF FLEX J3 BTH Connector on Flex | | | | | |
|---|---|---|---|---|---|---|---|---|---|---|---|
| 65 | 173 | 87L | 129 | 219 | 110L | 65 | 84 | 42R | 129 | 38 | 19R |
| 66 | 83 | 42L | 131 | 221 | 111L | 66 | 174 | 87R | 131 | 36 | 18R |
| 67 | 175 | 88L | 133 | G | G | 67 | 82 | 41R | 133 | G | G |
| 68 | 81 | 41L | 135 | 223 | 112L | 68 | 176 | 88R | 135 | 34 | 17R |
| 69 | G | G | 137 | 225 | 113L | 69 | G | G | 137 | 32 | 16R |
| 70 | G | G | 139 | G | G | 70 | G | G | 139 | G | G |
| 71 | 177 | 89L | 141 | 227 | 114L | 71 | 80 | 40R | 141 | 30 | 15R |
| 72 | 79 | 40L | 143 | 229 | 115L | 72 | 178 | 89R | 143 | 28 | 14R |
| 73 | 179 | 90L | 145 | 231 | 116L | 73 | 78 | 39R | 145 | 26 | 13R |
| 74 | 77 | 39L | 147 | G | G | 74 | 180 | 90R | 147 | G | G |
| 75 | 181 | 91L | 149 | 233 | 117L | 75 | 76 | 38R | 149 | 24 | 12R |
| 76 | 75 | 38L | 151 | 235 | 118L | 76 | 182 | 91R | 151 | 22 | 11R |
| 77 | G | G | 153 | G | G | 77 | G | G | 153 | G | G |
| 78 | G | G | 155 | 237 | 119L | 78 | G | G | 155 | 20 | 10R |
| 79 | 183 | 92L | 157 | 239 | 120L | 79 | 74 | 37R | 157 | 18 | 9R |
| 80 | 73 | 37L | 159 | 241 | 121L | 80 | 184 | 92R | 159 | 16 | 8R |
| 81 | 185 | 93L | 161 | G | G | 81 | 72 | 36R | 161 | G | G |
| 82 | 71 | 36L | 163 | 243 | 122L | 82 | 186 | 93R | 163 | 14 | 7R |
| 83 | G | G | 165 | 245 | 123L | 83 | G | G | 165 | 12 | 6R |
| 84 | G | G | 167 | G | G | 84 | G | G | 167 | G | R |
| 85 | 187 | 94L | 169 | 247 | 124L | 85 | 70 | 35R | 169 | 10 | 5R |
| 86 | 69 | 35L | 171 | 249 | 125L | 86 | 188 | 94R | 171 | 8 | 4R |
| 87 | 189 | 95L | 173 | 251 | 126L | 87 | 68 | 34R | 173 | 6 | 3R |
| 88 | 67 | 34L | 175 | G | G | 88 | 190 | 95R | 175 | G | R |
| 89 | 191 | 96L | 177 | 253 | 127L | 89 | 66 | 33R | 177 | 4 | 2R |
| 90 | 65 | 33L | 179 | 255 | 128L | 90 | 192 | 96R | 179 | 2 | 1R |

Pin-Out definition for the J1 and J3 BTH connector on the Flex circuit.

FIG.12B-3

ITT Cannon Connector - Array Channel Layout

G = Signal return ground
Open = Trace on transition card is connected to ITT connector, trace is left open circuit on PCB

| | 1 | 2 | 3 | 4 | 5 | 6 | 7 | 8 | 9 | 10 | 11 | 12 |
|---|---|---|---|---|---|---|---|---|---|---|---|---|
| A | 209 | 17 | 213 | 21 | 89 | 25 | 154 | 218 | 22 | 214 | 86 | 130 |
| B | 145 | G | 149 | G | 217 | G | 90 | G | 150 | G | 2 | G |
| C | 195 | 81 | 207 | 85 | 3 | 153 | 196 | 26 | 200 | 86 | Open | 194 |
| D | G | 131 | G | 143 | G | 75 | G | 68 | G | 136 | G | Open |
| E | 3 | 67 | 15 | 79 | 203 | 139 | 4 | 132 | 8 | 72 | Open | Open |
| F | 197 | 133 | 193 | 129 | 13 | 77 | 198 | 70 | Open | Open | 222 | 30 |
| G | 5 | G | 1 | G | 205 | G | 6 | G | Open | G | 158 | G |
| H | 151 | 69 | Open | 65 | 71 | 141 | 208 | 134 | 84 | Open | 216 | 94 |
| I | G | 215 | G | Open | G | 7 | G | 144 | G | 20 | G | 24 |
| J | 87 | 23 | Open | Open | 199 | 135 | 80 | 16 | 212 | 148 | 152 | 88 |
| K | Open | Open | 93 | 29 | 73 | 9 | 202 | 10 | 78 | 14 | 210 | 18 |
| L | Open | G | 157 | G | 137 | G | 74 | G | 206 | G | 82 | G |
| M | 19 | Open | 31 | 221 | 27 | 201 | 12 | 138 | 32 | 142 | 28 | 146 |
| N | G | 211 | G | 159 | G | 155 | G | 204 | G | 224 | G | 220 |
| O | 83 | 147 | 95 | 223 | 91 | 219 | 76 | 140 | 96 | 160 | 92 | 156 |

| | 1 | 2 | 3 | 4 | 5 | 6 | 7 | 8 | 9 | 10 | 11 | 12 |
|---|---|---|---|---|---|---|---|---|---|---|---|---|
| A | 241 | 49 | 245 | 53 | 121 | 57 | 186 | 250 | 54 | 246 | 98 | 162 |
| B | 177 | G | 181 | G | 249 | G | 122 | G | 182 | G | 34 | G |
| C | 227 | 113 | 239 | 117 | 35 | 185 | 228 | 58 | 232 | 116 | Open | 226 |
| D | G | 163 | G | 175 | G | 107 | G | 100 | G | 168 | G | Open |
| E | 35 | 99 | 47 | 111 | 235 | 171 | 36 | 164 | 40 | 104 | Open | Open |
| F | 229 | 165 | 225 | 161 | 45 | 109 | 230 | 102 | Open | Open | 254 | 62 |
| G | 37 | G | 33 | G | 237 | G | 38 | G | Open | G | 190 | G |
| H | 183 | 101 | Open | 97 | 103 | 173 | 240 | 166 | 116 | Open | 248 | 126 |
| I | G | 247 | G | Open | G | 39 | G | 176 | G | 52 | G | 56 |
| J | 119 | 55 | Open | Open | 231 | 167 | 112 | 48 | 244 | 180 | 184 | 120 |
| K | Open | Open | 125 | 61 | 105 | 41 | 234 | 42 | 110 | 46 | 242 | 50 |
| L | Open | G | 189 | G | 169 | G | 106 | G | 238 | G | 114 | G |
| M | 51 | Open | 63 | 253 | 59 | 233 | 44 | 170 | 64 | 174 | 60 | 178 |
| N | G | 243 | G | 191 | G | 187 | G | 236 | G | 256 | G | 252 |
| O | 115 | 179 | 127 | 255 | 123 | 251 | 108 | 172 | 128 | 192 | 124 | 188 |

Exemplary Pin Out for ITT Cannon ZIF Connector

Fig. 15B

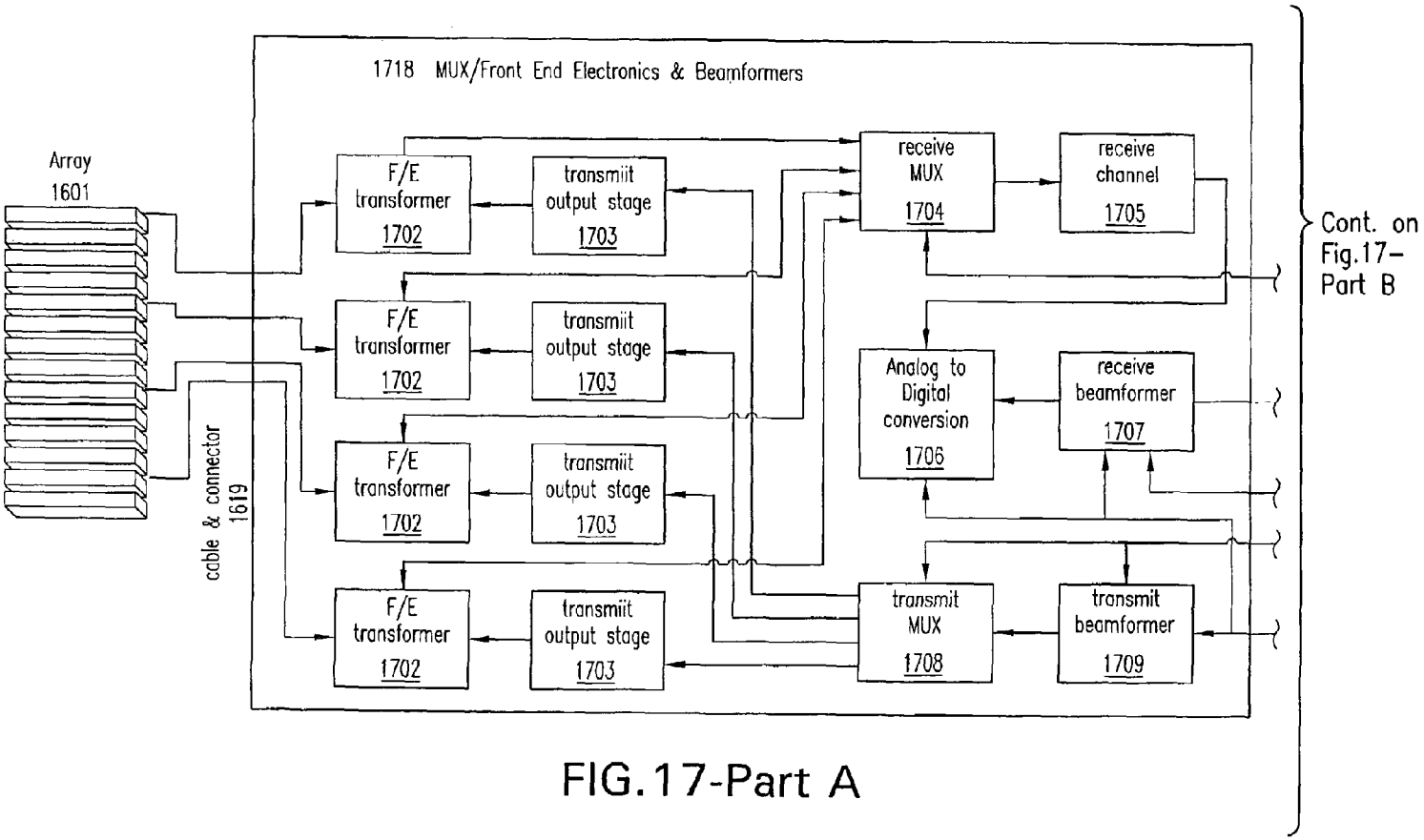
FIG. 17-Part A

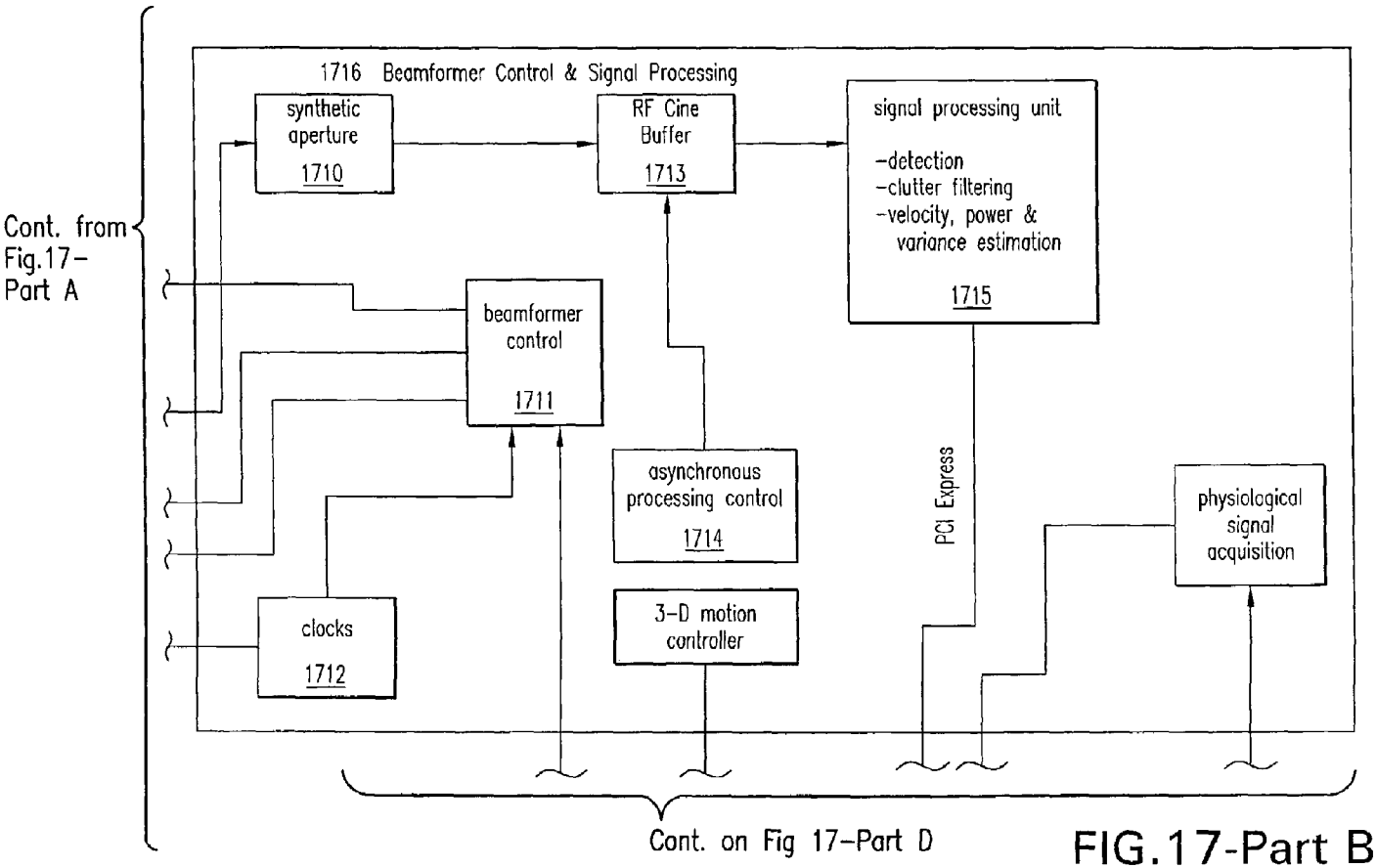
FIG.17-Part B

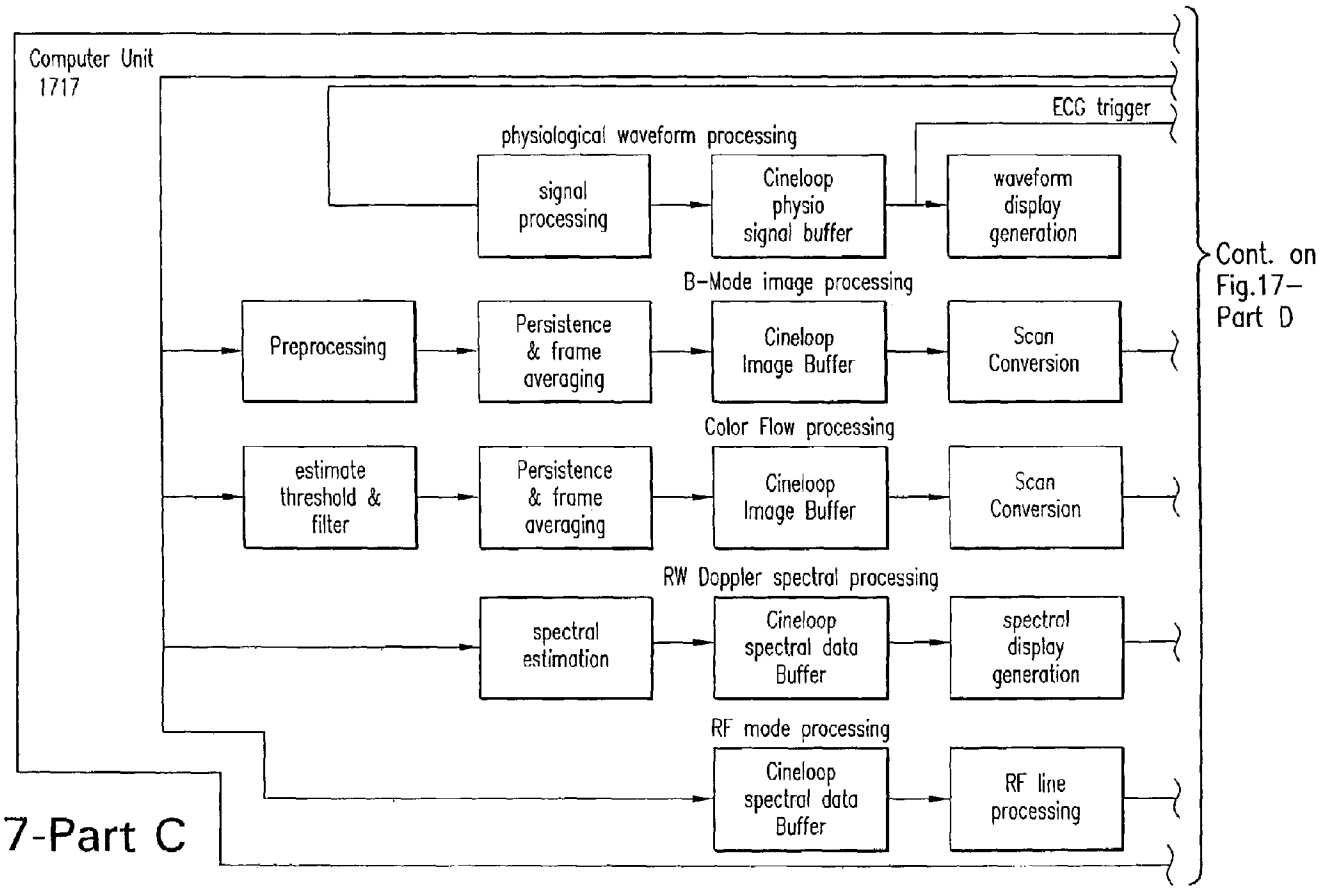
FIG. 17-Part C

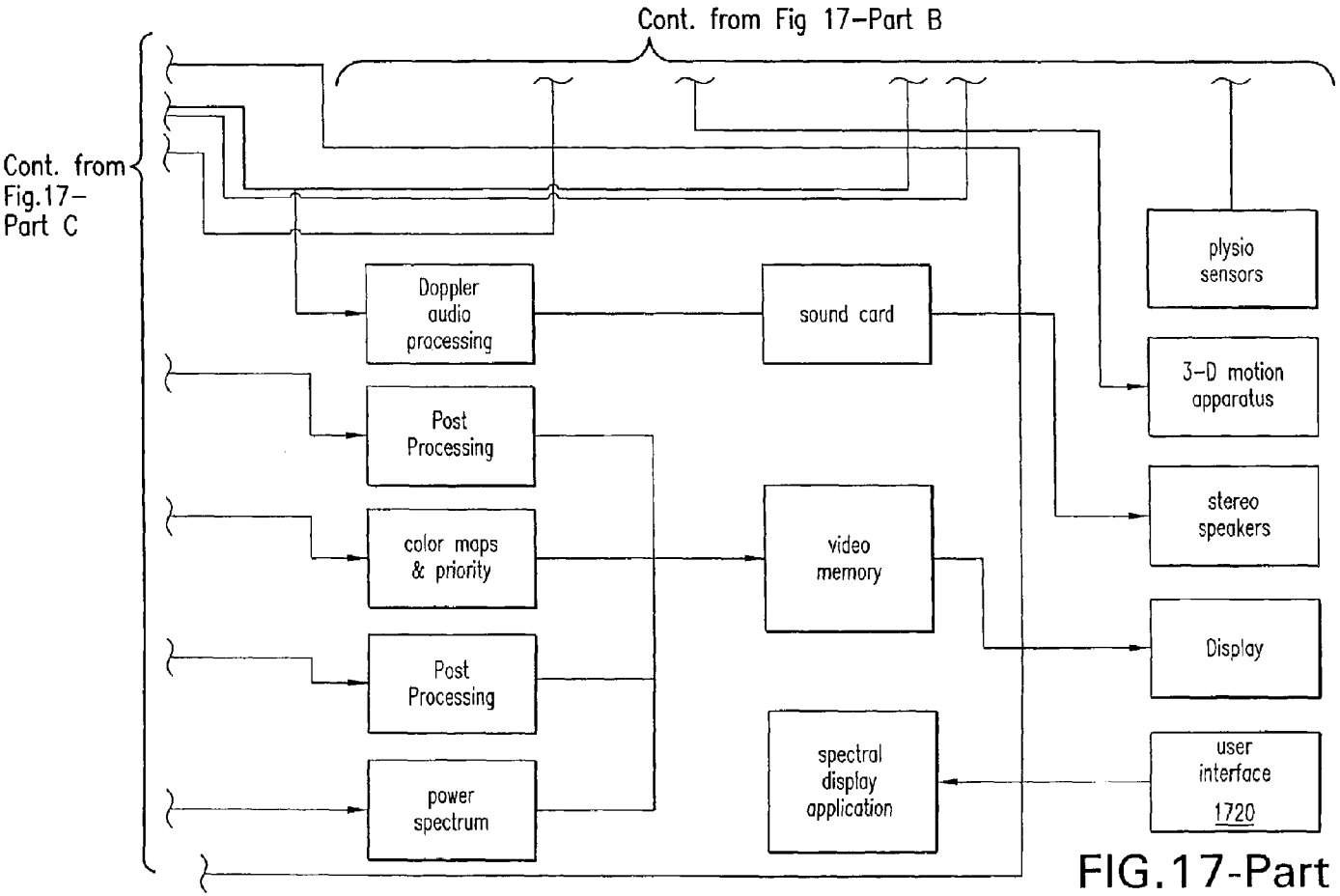
FIG.17-Part D

1814

```
i...........q...i...........q...i...........q...i...........q
                              |0-3|
```

```
q...i...........q...i...........q...i...........q...i
                                   |<-  4-15 ->|
```

HIGH FREQUENCY ARRAY ULTRASOUND SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application claims the benefit of U.S. Provisional Patent Application No. 60/733,091 filed Nov. 2, 2005, and the benefit of U.S. Provisional Patent application No. 60/733,089 filed Nov. 2, 2005, both of which are fully incorporated herein and made a part hereof.

BACKGROUND OF THE INVENTION

Ultrasound echography systems using an arrayed transducer have been used in human clinical applications where the desired image resolution is in the order of millimeters. Operating frequencies in these clinical systems are typically below 10 MHz. With these low operating frequencies, however, such systems are not appropriate for imaging where higher resolutions are needed, for example in imaging small animals such as mice or small tissue structures in humans.

Moreover, small animal imaging applications present several challenging requirements which are not met by currently available imaging systems. The heart rate of an adult mouse may be as high as 500 beats per minute, so high frame rate capability may be desired. The width of the region being imaged, the field of view, should also be sufficient to include the entire organ being studied.

Ultrasound systems for imaging at frequencies above 15 MHz have been developed using a single element transducer. However, arrayed transducers offer better image quality, can achieve higher acquisition frame rates and offer other advantages over single element transducer systems. The embodiments according to the present invention overcome many of the challenges in the current art, including those described above.

SUMMARY OF THE INVENTION

Provided herein is a system and method for acquiring an ultrasound signal comprised of a signal processing unit adapted for acquiring a received ultrasound signal from a ultrasound transducer having a plurality of elements. The system can be adapted to receive ultrasound signals having a frequency of at least 15 megahertz (MHz) with a fixed transducer having a field of view of at least 5.0 millimeters (mm) at a frame rate of at least 20 frames per second (fps). The signal processing unit can further produce an ultrasound image from the acquired ultrasound signal. The transducer can be, but is not limited to, a linear array transducer, a phased array transducer, a two-dimensional (2-D) array transducer, or a curved array transducer. The system can include such a transducer or be adapted to operate with such a transducer.

Also provided herein is a system and method for acquiring an ultrasound signal comprising a processing unit for acquiring received ultrasound signals from an ultrasound transducer operating at a transmit and receive frequency of at least 15 MHz, wherein the processing unit comprises a signal sampler that uses quadrature sampling to acquire the ultrasound signal.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments according to the invention and together with the description, serve to explain the principles of the invention:

FIG. 12B is an exemplary pin-out table for the connector shown in FIGS. 5B and 12A;

FIG. 15B illustrates an exemplary termination pin-out for the individual coax cables of a medical cable assembly to a multi-pin ZIF connector having an exemplary ZIF connector such as an ITT Cannon DLM6 connector;

FIG. 17 is a block diagram further illustrating the exemplary high frequency ultrasonic imaging system shown in FIG. 16;

FIG. 18b is an exemplary embodiment providing additional detail of the front end electronics shown in FIG. 18a;

DETAILED DESCRIPTION

The present invention may be understood more readily by reference to the following detailed description of the invention and the Examples included therein and to the Figures and their previous and following description.

Before the present compounds, compositions, articles, devices, and/or methods are disclosed and described, it is to be understood that this invention is not limited to specific methods, specific components, or to particular computer architecture, as such may, of course, vary. It is also to be understood that the terminology used herein is for the purpose of describing particular embodiments only and is not intended to be limiting. As used in the specification and the appended claims, the singular forms "a," "an" and "the" include plural referents unless the context clearly dictates otherwise. Thus, for example, reference to "a processing unit," or to "a receive channel" includes two or more such processing units or receive channels, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Figure 1:
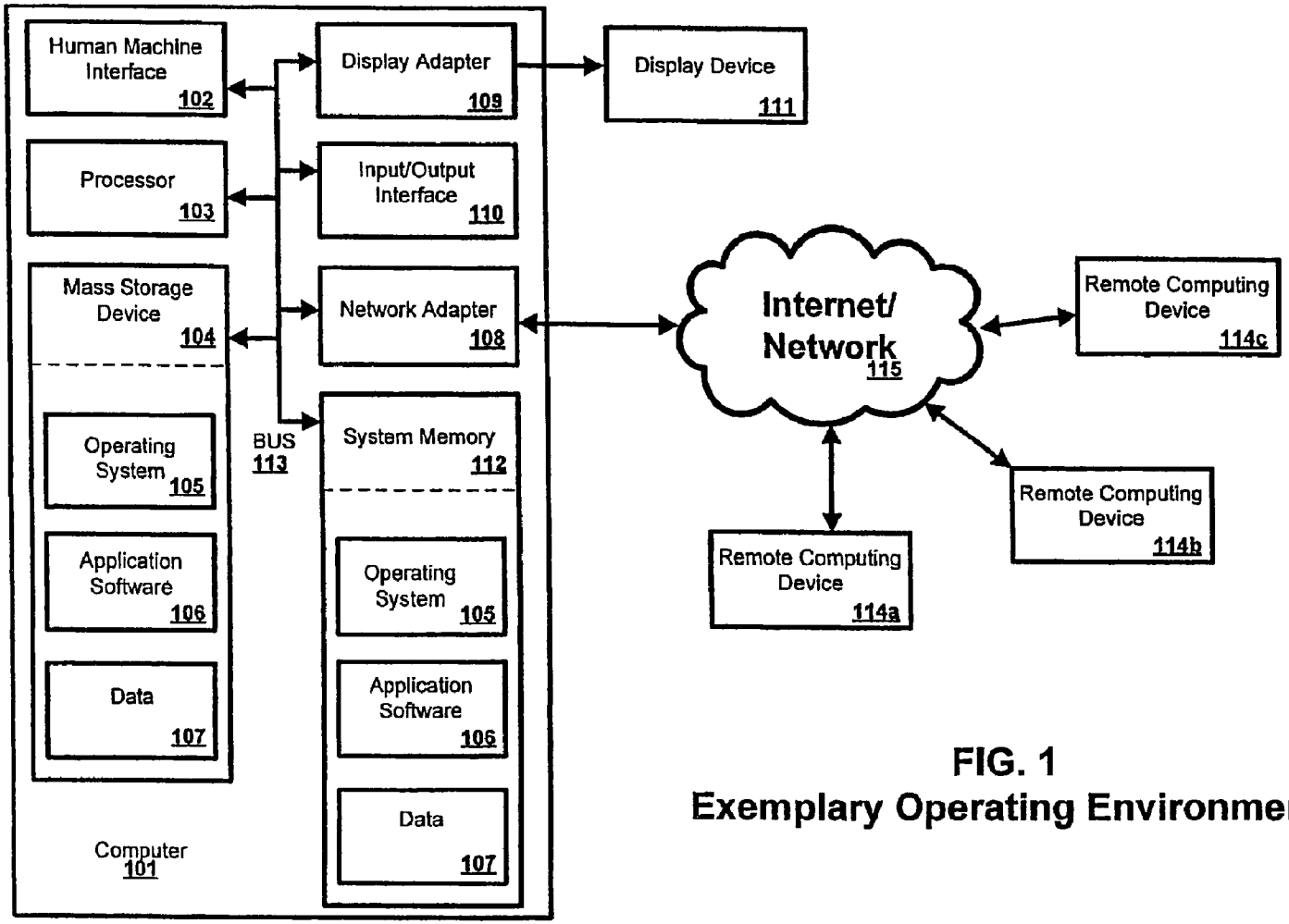
FIG. 1 is a representation in block diagram form of a computing operating environment.

Aspects of the exemplary systems disclosed herein can be implemented via a general-purpose computing device such as one in the form of a computer 101 shown in FIG. 1. The components of the computer 101 can include, but are not limited to, one or more processors or processing units 103, a system memory 112, and a system bus 113 that couples various system components including the processor 103 to the system memory 112.

The system bus 113 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 113, and all buses specified in this description can also be implemented over a wired or wireless network connection and each of the subsystems, including the processor 103, a mass storage device 104, an operating system 105, application software 106, data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically includes a variety of computer readable media. Such media can be any available media that is accessible by the computer 101 and includes both volatile and non-volatile media, removable and non-removable media. The system memory 112 includes computer readable media in the form of volatile memory, such as random access memory (RAM), and/or non-volatile memory, such as read only memory (ROM). The system memory 112 typically contains data such as data 107 and/or program modules such as operating system 105 and application software 106 that are immediately accessible to and/or are presently operated on by the processing unit 103.

The computer 101 may also include other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 104, including by way of example, an operating system 105 and application software 106. Each of the operating system 105 and application software 106 (or some combination thereof) may include elements of the programming and the application software 106. Data 107 can also be stored on the mass storage device 104. Data 104 can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer 101 via an input device (not shown). Examples of such input devices include, but are not limited to, a keyboard, pointing device (e.g., a "mouse"), a microphone, a joy stick, a serial port, a scanner, and the like. These and other input devices can be connected to the processing unit 103 via a human machine interface 102 that is coupled to the system bus 113, but may be connected by other interface and bus structures, such as a parallel port, game port, or a universal serial bus (USB). In an exemplary system of an embodiment according to the present invention, the user interface can be chosen from one or more of the input devices listed above. Optionally, the user interface can also include various control devices such as toggle switches, sliders, variable resistors and other user interface devices known in the art. The user interface can be connected to the processing unit 103. It can also be connected to other functional blocks of the exemplary system described herein in conjunction with or without connection with the processing unit 103 connections described herein.

A display device 111 can also be connected to the system bus 113 via an interface, such as a display adapter 109. For example, a display device can be a monitor or an LCD (Liquid Crystal Display). In addition to the display device 111, other output peripheral devices can include components such as speakers (not shown) and a printer (not shown) which can be connected to the computer 101 via Input/Output Interface 110.

The computer 101 can operate in a networked environment using logical connections to one or more remote computing devices 114a,b,c. By way of example, a remote computing device can be a personal computer, portable computer, a server, a router, a network computer, a peer device or other common network node, and so on. Logical connections between the computer 101 and a remote computing device 114a,b,c can be made via a local area network (LAN) and a general wide area network (WAN). Such network connections can be through a network adapter 108. A network adapter 108 can be implemented in both wired and wireless environments. Such networking environments are common-place in offices, enterprise-wide computer networks, intranets, and the Internet 115. The remote computer 114a,b,c may be a server, a router, a peer device or other common network node, and typically includes all or many of the elements already described for the computer 101. In a networked environment, program modules and data may be stored on the remote computer 114a,b,c. The logical connections include a LAN and a WAN. Other connection methods may be used, and networks may include such things as the "world wide web" or Internet.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of application software 106 may be stored on or transmitted across some form of computer readable media. Computer readable media can be any available media that can be accessed by a computer. By way of example, and not limitation, computer readable media may comprise "computer storage media" and "communications media." Computer storage media include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Aspects of the exemplary systems shown in the Figures and described herein, can be implemented in various forms including hardware, software, and a combination thereof. The hardware implementation can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), field programmable gate array(s) (FPGA), etc. The software comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

Aspects of the exemplary systems can be implemented in computerized systems. Aspects of the exemplary systems, including for instance the computing unit 101, can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

Aspects of the exemplary systems can be described in the general context of computer instructions, such as program modules, being executed by a computer. Generally, program modules include routines, programs, objects, components, data structures, etc. that perform particular tasks or implement particular abstract data types. The system and method may also be practiced in distributed computing environments where tasks are performed by remote processing devices that are linked through a communications network. In a distributed computing environment, program modules may be located in both local and remote computer storage media including memory storage devices.

Among many possible applications, the described embodiments enable in vivo visualization, assessment, and measurement of anatomical structures and hemodynamic function in longitudinal imaging studies of small animals. The systems can provide images having very high resolution, image uniformity, depth of field, adjustable transmit focal depths, multiple transmit focal zones for multiple uses. For example, the ultrasound image can be of a subject or an anatomical portion thereof, such as a heart or a heart valve. The image can also be of blood and can be used for applications including evaluation of the vascularization of tumors. The systems can be used to guide needle injections.

The described embodiments can also be used for human clinical, medical, manufacturing (e.g., ultrasonic inspections, etc.) or other applications where producing an image at a transmit frequency of 15 MHz or higher is desired.

Embodiments according to the described systems can comprise one or more of the following, which are described in greater detail herein: an array transducer that can be operatively connected to a processing system that may be comprised of one or more of signal and image processing capabilities; digital transmit and receive beamformer subsystems; analog front end electronics; a digital beamformer controller subsystem; a high voltage subsystem; a computer module; a power supply module; a user interface; software to run the beamformer; a scan converter, and other system features as described herein.

An arrayed transducer used in the system can be incorporated into a scanhead that, in one embodiment, may be attached to a fixture during imaging which allows the operator to acquire images free of the vibrations and shaking that usually result from "free hand" imaging. A small animal subject may also be positioned on a heated platform with access to anesthetic equipment, and a means to position the scanhead relative to the subject in a flexible manner. The scanhead can be attached to a fixture during imaging. The fixture can have various features, such as freedom of motion in three dimensions, rotational freedom, a quick release mechanism, etc. The fixture can be part of a "rail system" apparatus, and can integrate with the heated mouse platform.

The systems can be used with platforms and apparatus used in imaging small animals including "rail guide" type platforms with maneuverable probe holder apparatuses. For example, the described systems can be used with multi-rail imaging systems, and with small animal mount assemblies as described in U.S. patent application Ser. No. 10/683,168, entitled "Integrated Multi-Rail Imaging System," U.S. patent application Ser. No. 10/053,748, entitled "Integrated Multi-Rail Imaging System," U.S. patent application Ser. No. 10/683,870, now U.S. Pat. No. 6,851,392, issued Feb. 8, 2005, entitled "Small Animal Mount Assembly," and U.S. patent application Ser. No. 11/053,653, entitled "Small Animal Mount Assembly," which are each fully incorporated herein by reference.

Small animals can be anesthetized during imaging and vital physiological parameters such as heart rate and temperature can be monitored. Thus, an embodiment of the system may include means for acquiring ECG and temperature signals for processing and display. An embodiment of the system may also display physiological waveforms such as an ECG, respiration or blood pressure waveform.

Overview

Provided herein are embodiments of a system for acquiring ultrasound signals comprising a signal processing unit adapted for acquiring a received ultrasound signal from an ultrasound transducer having a plurality of elements. The system can be adapted to receive ultrasound signals having a frequency of at least 15 megahertz (MHz) with a transducer having a field of view of at least 5.0 millimeters (mm) at a frame rate of at least 20 frames per second (fps). In other embodiments, the ultrasound signals can be acquired at an acquisition rate of 50, 100, or 200 (fps). Optionally, ultrasound signals can be acquired at an acquisition rate of 200 frames per second (fps) or higher. In other examples, the received ultrasound signals can be acquired at a frame rate within the range of about 100 fps to about 200 fps. In some exemplary aspects, the length of the transducer is equal to the field of view. The field of view can be wide enough to include organs of interest such as the small animal heart and surrounding tissue for cardiology, and full length embryos for abdominal imaging. In one embodiment, the two-way bandwidth of the transducer can be approximately 50% to 100%. Optionally, the two-way bandwidth of the transducer can be approximately 60% to 70%. Two-way bandwidth refers to the bandwidth of the transducer that results when the transducer is used both as a transmitter of ultrasound and a receiver—that is, the two-way bandwidth is the bandwidth of the one-way spectrum squared.

The processing unit produces an ultrasound image from the acquired ultrasound signal(s). The acquired signals may be processed to generate an ultrasound image at display rate that is slower than the acquisition rate. Optionally, the generated ultrasound image can have a display rate of 100 fps or less. For example, the generated ultrasound image has a display rate of 30 fps or less. The field of view can range from about 2.0 mm to about 30.0 mm. When a smaller field of view is utilized, the processing unit can acquire the received ultrasound signals at an acquisition rate of at least 300 frames per second (fps). In other examples, the acquisition rate can be 50, 100, 200 or more frames per second (fps).

In one embodiment, in which a 30 MHz center frequency transducer is used, the image generated using the disclosed systems may have a lateral resolution of about 150 microns (μm) or less and an axial resolution of about 75 microns (μm) or less. For example, the image can have an axial resolution of about 30 microns (μm). Furthermore, embodiments according to the present invention transmit ultrasound that may be focused at a depth of about 1.0 mm to about 30.0 mm. For example, the transmitted ultrasound can be focused at a depth of about 3.0 mm to about 10.0 mm. In other examples, the transmitted ultrasound can be focused at a depth of about 2.0 mm to about 12.0 mm, of about 1.0 mm to about 6.0 mm, of about 3.0 mm to about 8.0 mm, or of about 5.0 mm to about 30.0 mm.

Transducers

In various embodiments, the transducer can be, but is not limited to, a linear array transducer, a phased array transducer, a two-dimensional (2-D) array transducer, or a curved array transducer. A linear array is typically flat, i.e., all of the elements lie in the same (flat) plane. A curved linear array is typically configured such that the elements lie in a curved plane. The transducers described herein are "fixed" transducers. The term "fixed" means that the transducer array does not utilize movement in its azimuthal direction during transmission or receipt of ultrasound in order to achieve its desired operating parameters, or to acquire a frame of ultrasound data. Moreover, if the transducer is located in a scanhead or other imaging probe, the term "fixed" may also mean that the transducer is not moved in an azimuthal or longitudinal direction relative to the scan head, probe, or portions thereof during operation. The described transducers, which are fixed as described, are referred to throughout as an "array," a "transducer," an "ultrasound transducer," an "ultrasound array," an "array transducer," an "arrayed transducer," an "ultrasonic transducer" or combinations of these terms, or by other terms which would be recognized by those skilled in the art as referring to an ultrasound transducer. The transducers as described herein can be moved between the acquisition of ultrasound frames, for example, the transducer can be moved between scan planes after acquiring a frame of ultrasound data, but such movement is not required for their operation. As one skilled in the art would appreciate however, the transducer of the present system can be moved relative to the object imaged while still remaining fixed as to the operating parameters. For example, the transducer can be moved relative to the subject during operation to change position of the scan plane or to obtain different views of the subject or its underlying anatomy.

Arrayed transducers are comprised of a number of elements. In one embodiment, the transducer used to practice one or more aspects of the present invention comprises at least 64 elements. In one aspect, the transducer comprises 256 elements. The transducer can also comprise fewer or more than 256 elements. The transducer elements can be separated by a distance equal to about one-half the wavelength to about two times the wavelength of the center transmit frequency of the transducer (referred to herein as the "element pitch."). In one aspect, the transducer elements are separated by a distance equal to about the wavelength of the center transmit frequency of the transducer. Optionally, the center transmit frequency of the transducer used is equal to or greater than 15 MHz. For example, the center transmit frequency can be approximately 15 MHz, 20 MHz, 30 MHz, 40 MHz, 50 MHz, 55 MHz or higher. In some exemplary aspects, the ultrasound transducer can transmit ultrasound into the subject at a center frequency within the range of about 15 MHz to about 80 MHz. In one embodiment according to the present invention, the transducer has a center operating frequency of at least 15 MHz and the transducer has an element pitch equal to or less than 2.0 times the wavelength of sound at the transducer's transmitted center frequency. The transducer can also have an element pitch equal to or less than 1.5 times the wavelength of sound at the transducers transmitted center frequency.

By non-limiting example, one transducer that may be used with the described system can be, among others, an arrayed transducer as described in U.S. patent application Ser. No. 11/109,986, entitled "Arrayed Ultrasonic Transducer," filed Apr. 20, 2005 and published on Dec. 8, 2005 as U.S. Patent Application Publication No.: US 2005/0272183 A1, which is fully incorporated herein by reference and made a part hereof. The transducer may also comprise an array of piezoelectric elements which can be electronically steered using variable pulsing and delay mechanisms. The processing system according to various embodiments of the present invention may include multiple transducer ports for the interface of one or more transducers or scanheads. As previously described, a scanhead can be hand held or mounted to rail system and the scanhead cable can be flexible.

Whether the system includes a transducer, or is adapted to be used with a separately acquired transducer, each element of the transducer can be operatively connected to a receive channel of a processing unit. Optionally, the number of transducer elements is greater than the number of receive channels. For example, the transducer may comprise at least 64 elements that are operatively connected to at least 32 receive channels. In one aspect, 256 elements are operatively connected to 64 receive channels. In another aspect, 256 elements are operatively I connected to 128 receive channels. In yet another aspect, 256 elements are operatively connected to 256 receive channels. Each element can also be operatively connected to a transmit channel.

Sampling

The system can further comprise one or more signal samplers for each receive channel. The signal samplers can be analog-to-digital converters (ADCs). The signal samplers can use direct sampling techniques to sample the received signals. Optionally, the signal samplers can use bandwidth sampling to sample the received signals. In another aspect, the signal samplers can use quadrature sampling to sample the received signals. Optionally, with quadrature sampling, the signal samplers comprise sampling clocks shifted 90 degrees out of phase. Also with quadrature sampling the sampling clocks also have a receive period, and the receive clock frequency can be approximately equal to the center frequency of a received ultrasound signal but may be different from the transmit frequency. For example, in many situations, the center frequency of the received signal has been shifted lower than the center frequency of the transmit signal due to frequency dependent attenuation in the tissue being imaged. For these situations the receive sample clock frequency can be lower than the transmit frequency.

An acquired signal can be processed using an interpolation filtration method. Using the interpolation filtration method a delay resolution can be used, which can be less than the receive clock period. In an exemplary aspect, the delay resolution can be, for example, 1/16 of the receive clock period.

The processing unit can comprise a receive beamformer. The receive beamformer can be implemented using at least one field programmable gate array (FPGA) device. The processing unit can also comprise a transmit beamformer. The transmit beamformer can also be implemented using at least one FPGA device.

In one aspect, 512 lines of ultrasound are generated, transmitted into the subject and received from the subject for each frame of the generated ultrasound image. In a further aspect, 256 lines of ultrasound can also be generated, transmitted into the subject and received from the subject for each frame of the generated ultrasound image. In another aspect, at least two lines of ultrasound can be generated, transmitted into the subject and received from the subject at each element of the array for each frame of the generated ultrasound image. Optionally, one line of ultrasound is generated, transmitted into the subject and received from the subject at each element of the array for each frame of the generated ultrasound image.

The ultrasound systems described herein can be used in multiple imaging modes. For example, the systems can be used to produce an image in B-mode, M-mode, Pulsed Wave (PW) Doppler mode, power Doppler mode, color flow Doppler mode, RF-mode and 3-D mode. The systems can be used in Color Flow Imaging modes, including directional velocity color flow, Power Doppler imaging and Tissue Doppler imaging. The systems can also be used with Steered PW Doppler, with very high pulse repetition frequencies (PRF). The systems can also be used in M-Mode, with simultaneous B-Mode, for cardiology or other applications where such techniques are desired. The system can optionally be used in Duplex and Triplex modes, in which M-Mode and PW Doppler and/or Color Flow modes run simultaneously with B-Mode in real-time. A 3-D mode in which B-Mode or Color Flow mode information is acquired over a 3-dimensional region and presented in a 3-D surface rendered display can also be used. A line based image reconstruction or "EKV" mode, can be used for cardiology or other applications, in which image information is acquired over several cardiac cycles and recombined to provide a very high frame rate display. Line based image reconstruction methods are described in U.S. patent application Ser. No. 10/736,232, now U.S. Pat. No. 7,052,460 issued May 30, 2006 and entitled "System for Producing an Ultrasound Image Using Line Based Image Reconstruction," which is incorporated fully herein by reference and made a part hereof. Such line based imaging methods image can be incorporated to produce an image when a high frame acquisition rate is desirable, for example when imaging a rapidly beating mouse heart. In the RF acquisition mode, raw RF data can be acquired, displayed and made available for off-line analysis.

In one embodiment, the transducer can transmit at a pulse repetition frequency (PRF) of at least 500 hertz (Hz). The system can further comprise a processing unit for generating a color flow Doppler ultrasound image from the received ultrasound. Optionally, the PRF is between about 100 Hz to about 150 KHz. In M-Mode or RF Mode the PRF is between about 100 Hz and about 10 KHz. For Doppler modes, the PRF can be between about 500 Hz and about 150 KHz. For M-Mode and RF mode, the PRF can be between about 50 Hz and about 10 KHz.

Exemplary Arrayed Transducer

Referring now to FIGS. 2A-15B, a circuit board according to an embodiment of the present invention is adapted to accept an exemplary transducer and that is further adapted to connect to at least one conventional connector. As noted herein, the conventional connector can be adapted to complementarily connect with a cable for transmission and/or supply of required signals. With regard to the figures, due to the fine detail of the circuit board and unless otherwise indicated, the figures are merely representative of complementary circuit boards and associated multi element arrays. FIGS. 5A-5C show various views of an exemplary circuit board for a 256 element array having a 75 micron pitch.

Figure 2B:
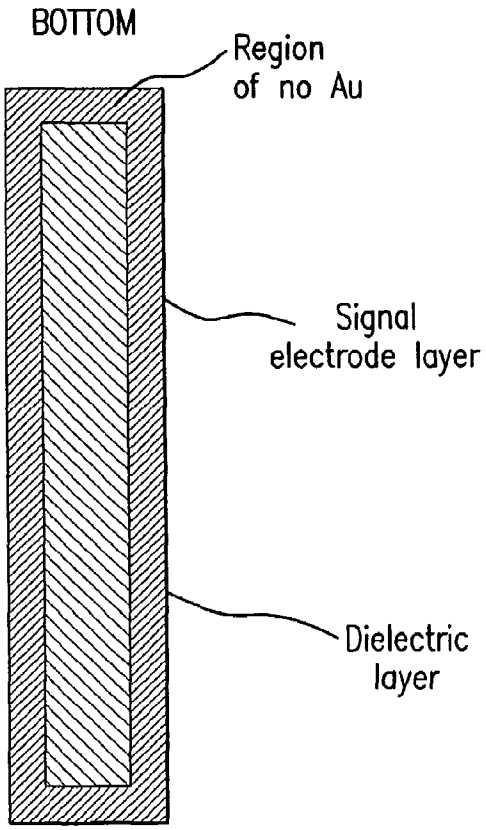
FIGS. 2A-2C, are exemplary top, bottom and cross-sectional views of an exemplary schematic PZT stack of the present invention, the top view showing, at the top and bottom of the PZT stack, portions of the ground electric layer extending outwardly from the overlying lens; the bottom view showing, at the longitudinally extending edges, exposed portions of the dielectric layer between individual signal electrode elements (as one will appreciate, not show in the center portion of the PZT stack are the lines showing the individualized signal electrode elements—one signal electrode per element of the PZT stack)
Figure 2A:
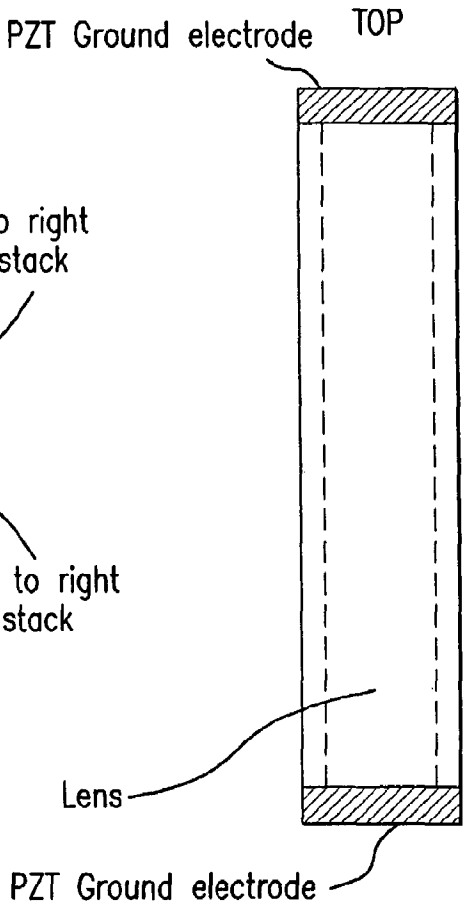

Referring now in particular to FIGS. 2A-4B, an exemplary transducer for use with the exemplary circuit board is illustrated. In FIGS. 2A-4B, exemplary top, bottom and cross-sectional views of an exemplary schematic PZT stack are shown. FIG. 2A shows a top view of the PZT stack and illustrates portions of the ground electric layer that extend from the top and bottom portions of the PZT stack. In one aspect, the ground electric layer extends the full width of the PZT stack. FIG. 2B shows a bottom view of the PZT stack. In this aspect, along the longitudinally extending edges of the PZT stack, the PZT stack forms exposed portions of the dielectric layer between individual signal electrode elements. In another aspect, the signal elements extend the full width of the PZT stack. As one will appreciate, not shown in the underlying "center portion" of the PZT stack are lines showing the individualized signal electrode elements. As one will further appreciate, there is one signal electrode per element of the PZT stack, e.g., 256 signal electrodes for a 256-element array.

Figure 2C:
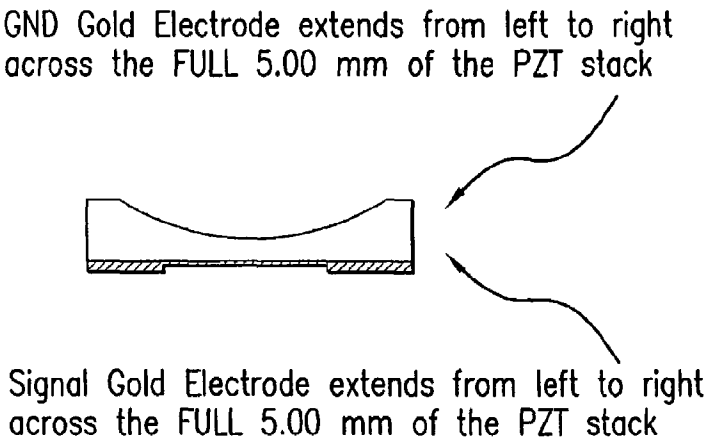
Figure 3A:
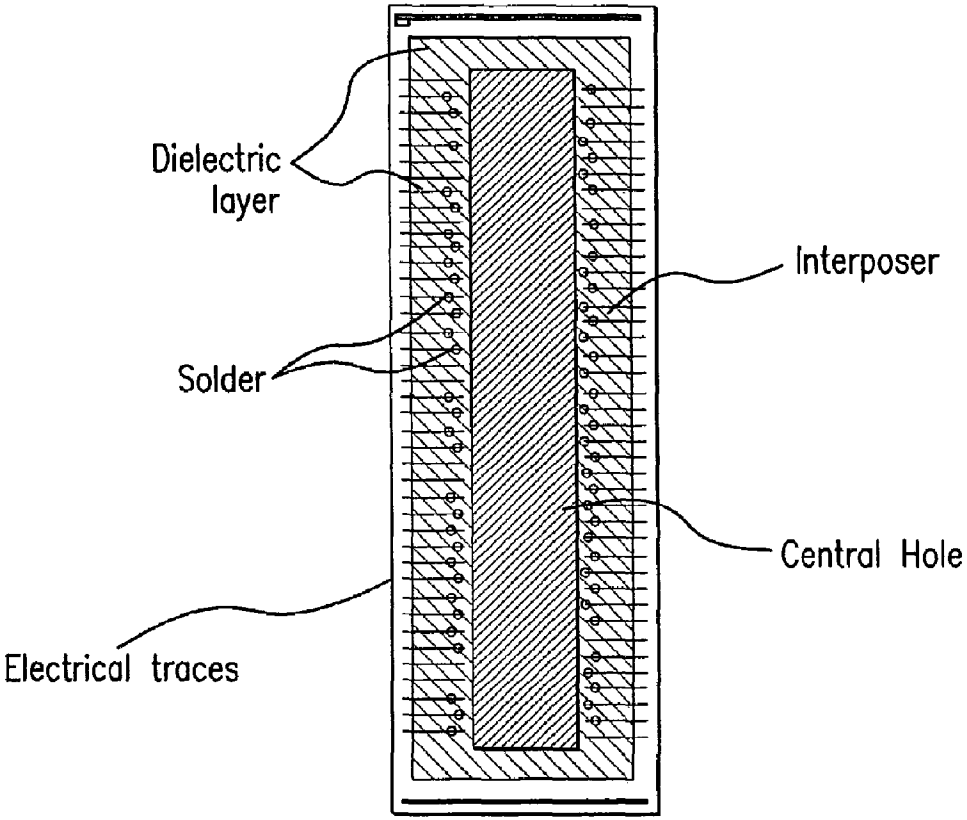
FIG. 3A is a top plan view of an interposer for use with the PZT stack of FIGS. 2A-2C, showing electrical traces extending outwardly from adjacent the central opening of the transducer and ground electrical traces located at the top and bottom portions of the interposer, showing a dielectric layer disposed thereon a portion of the surface of the interposer, the dielectric layer defining an array of staggered wells positioned along an axis parallel to the longitudinal axis of the interposer, each well communicating with an electrical trace of the interposer, and further showing a solder paste ball bump mounted therein each well in the dielectric layer such that, when a PZT stack is mounted thereon the dielectric layer and heat is applied, the solder melts to form the desired electrical continuity between the individual element signal electrodes and the individual trances on the interposer—the well helping to retain the solder within the confines of the well.
Figure 3B:
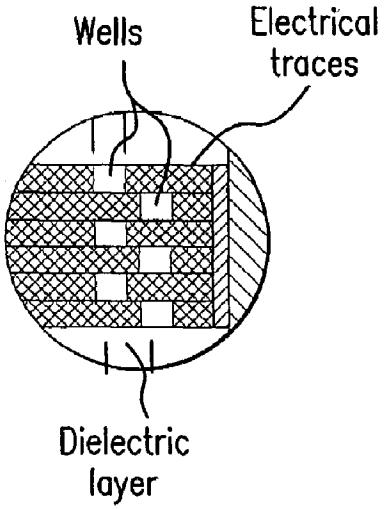
FIG. 3B is a partial enlarged view of the staggered wells of the dielectric layer and the electrical traces of the underlying interposer of FIG. 3A, the well sized to accept the solder paste ball bumps.

FIG. 3A is a top plan view of an interposer for use with the PZT stack of FIGS. 2A-C, comprising electrical traces extending outwardly from adjacent the central opening of the interposer. The interposer further comprises ground electrical traces located at the top and bottom portions of the piece.

The interposer can further comprise a dielectric layer disposed thereon a portion of the top surface of the interposer about the central opening of the piece. In this aspect, and referring also to FIG. 3B, the dielectric layer defines two arrays of staggered wells, one array being on each side of the central opening and extending along an axis parallel to the longitudinal axis of the interposer. Each well is in communication with an electrical trace of the interposer. A solder paste can be used to fill each of the wells in the dielectric layer such that, when a PZT stack is mounted thereon the dielectric layer and heat is applied, the solder melts to form the desired electrical continuity between the individual element signal electrodes and the individual trances on the interposer. In use, the well helps to retain the solder within the confines of the well.

Figures 4A, 4B:
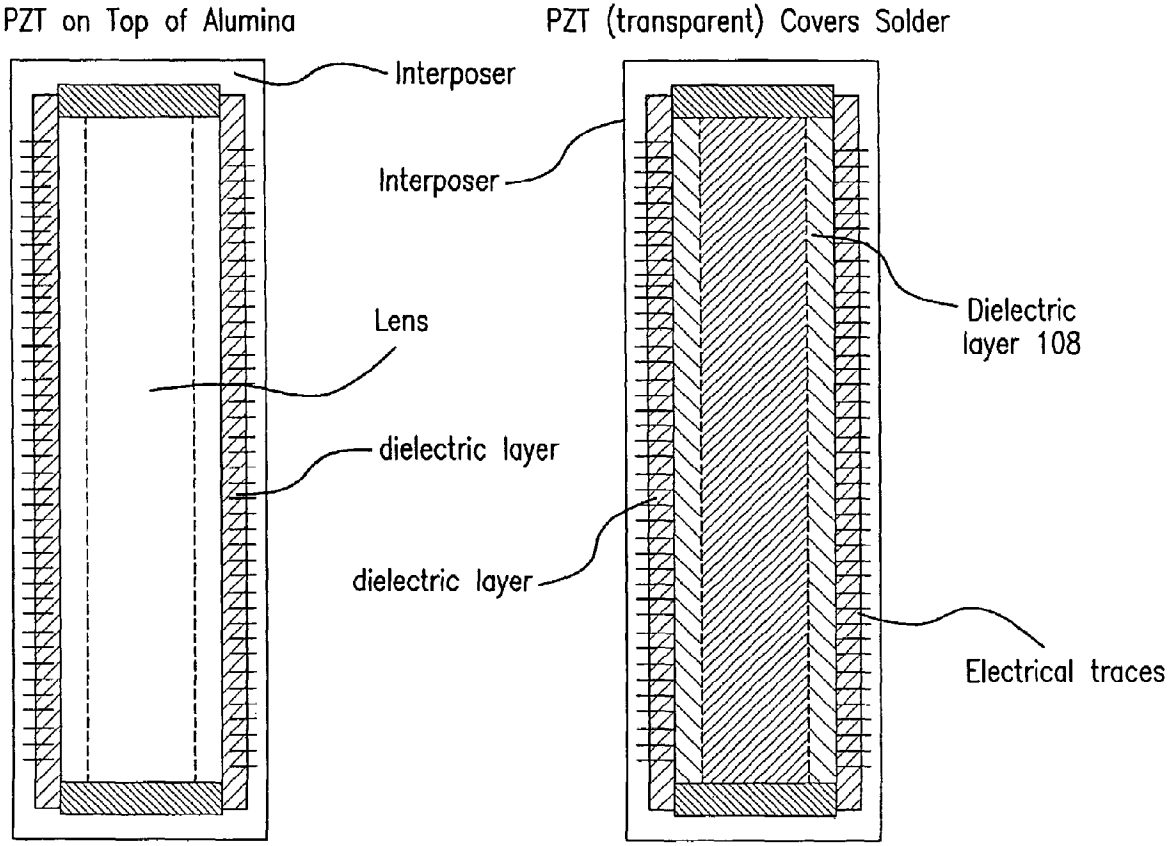
FIG. 4A is a top plan view of the PZT stack of FIG. 2A mounted thereon the dielectric layer and the interposer of FIG. 3A.
FIG. 4B is a top plan view of the PZT stack of FIG. 2A mounted thereon the dielectric layer and interposer of FIG. 3A, showing the PZT stack as a transparent layer to illustrate the mounting relationship between the PZT stack and the underlying interposer, the solder paste ball bumps mounted therebetween forming an electrical connection between the respective element signal electrodes and the electrical traces on the interposer.
Figure 5A:
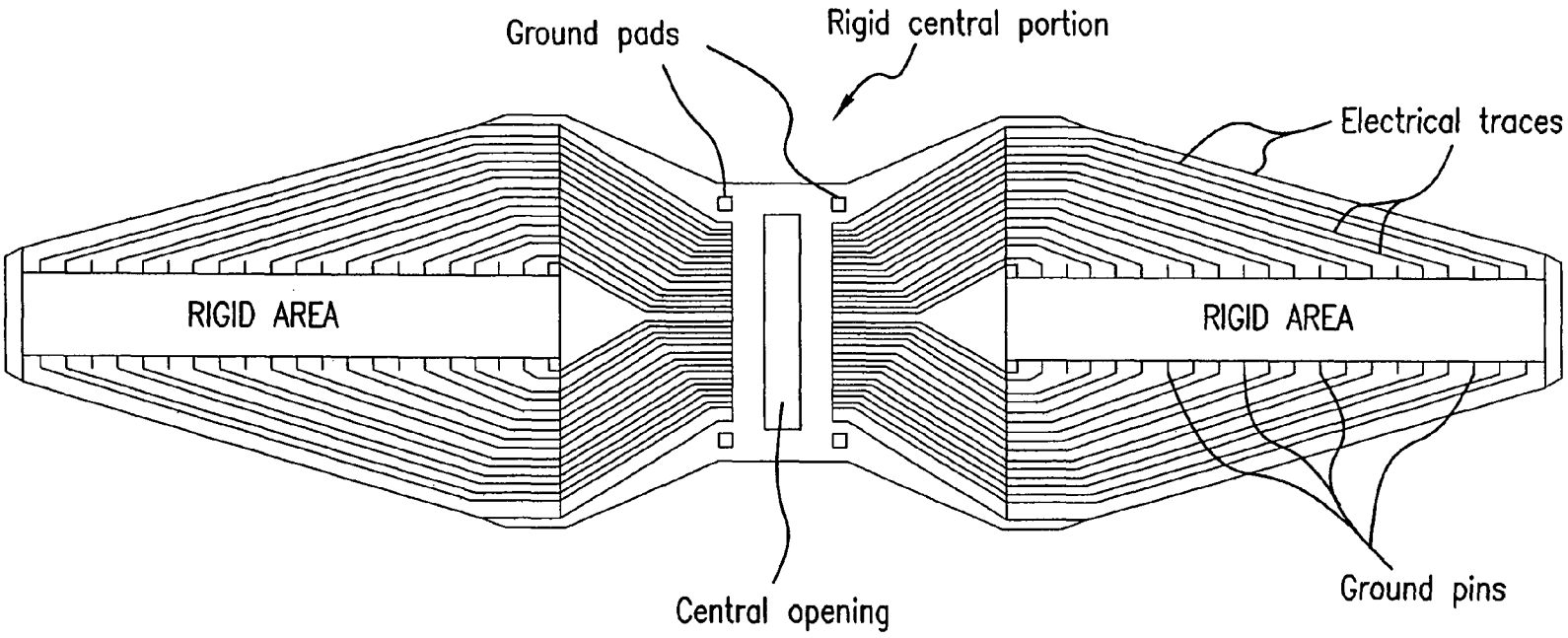
FIG. 5A is a schematic top plan view of an exemplary circuit board for mounting the transducer of the present invention thereto, the circuit board having a plurality of board electrical traces formed thereon, each board electrical trace having a proximal end adapted to couple to an electrical trace of the transducer and a distal end adapted to couple to a connector, such as, for example, a cable for communication of signals therethrough.
Figure 5B:
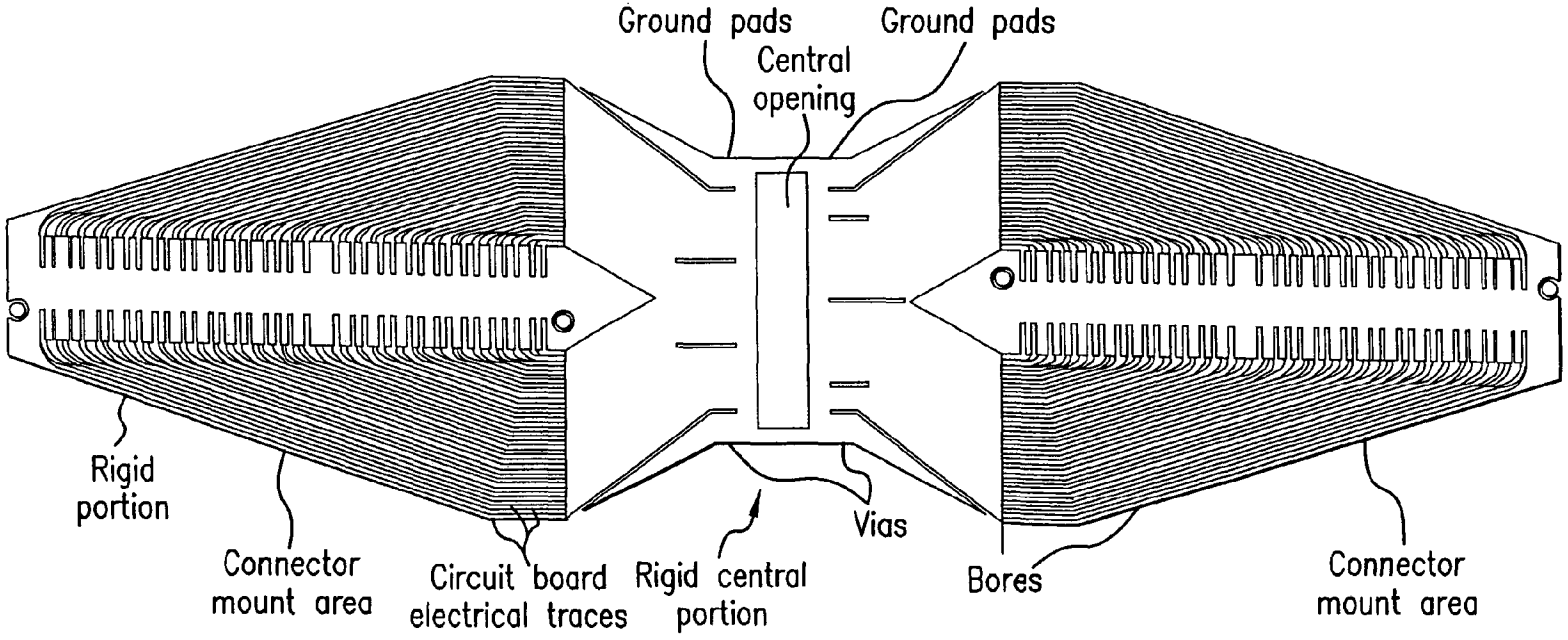
FIG. 5B is a top plan view of an exemplary circuit board for mounting of an exemplary 256-element array having a 75 micron pitch.
Figure 5C:
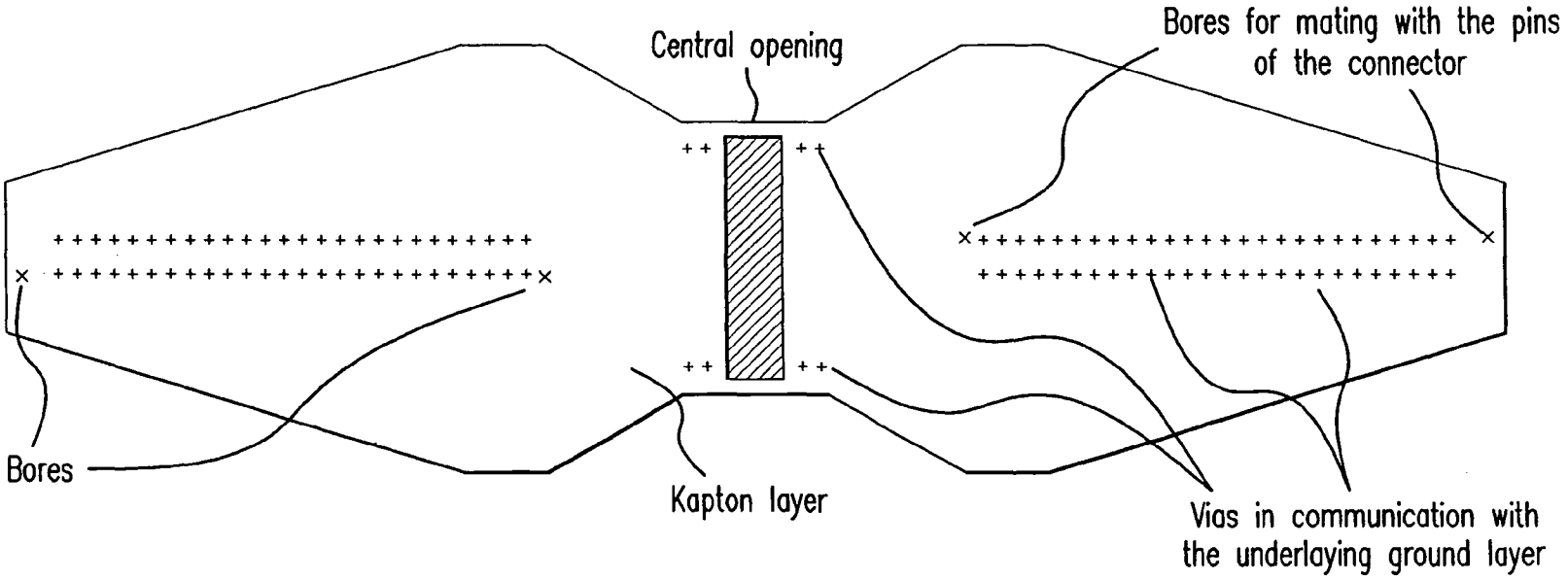
FIG. 5C is a top plan view of the vias of the circuit board of FIG. 5B that are in communication with an underlying ground layer of the circuit board.

FIG. 4A is a top plan view of the PZT stack shown in FIG. 2A mounted thereon the dielectric layer of the interposer shown in FIG. 3A. To aid in the understanding of the invention, FIG. 4B provides a top plan view of the PZT stack shown in FIG. 2A mounted thereon the dielectric layer and interposer shown in FIG. 3A, in which the PZT stack is shown as a transparency. This provides an illustration of the mounting relationship between the PZT stack and the underlying dielectric layer/interposer, the solder paste mounted therebetween forming an electrical connection between the respective element signal electrodes and the electrical traces on the interposer.

Referring now to FIG. 5A, a schematic top plan view of an exemplary circuit board for mounting the transducer of the present invention thereto is illustrated. In one aspect, at least a portion of the circuit board can be flexible. In one embodiment, the circuit board comprising a bottom copper ground layer and a Kapton™ layer mounted to the upper surface of the bottom copper ground layer. In one aspect, the circuit board can also comprise a plurality of underlying substantially rigid support structures. In this aspect, a central portion surrounding a central opening in the circuit board can have a rigid support structure mounted to the bottom surface of the bottom copper ground layer. In a further aspect, portions of the circuit board to which the connectors can be attached also have rigid support structures mounted to the bottom surface of the bottom copper ground layer.

The circuit board further comprise a plurality of board electrical traces formed thereon the top surface of the Kapton™ layer, each board electrical trace having a proximal end adapted to couple to an electrical trace of the transducer and a distal end adapted to couple to a connector, such as, for example, a cable for communication of signals therethrough. In one aspect, the length of the circuit forming each electrical trace has a substantially constant impedance.

The circuit board also comprises a plurality of vias that pass though the Kapton™ layer and are in communication with the underlying ground layer so that signal return paths, or signal ground paths, can be formed. Further, the circuit board comprises a plurality of ground pins. Each ground pin has a proximal end that is coupled to the ground layer of the circuit board (passing through one of the vias in the Kapton layer) and a distal end that is adapted to couple to the connector.

FIG. 5B is a top plan view of an exemplary circuit board for mounting of an exemplary 256-element array having a 75 micron pitch and FIG. 5C is a top plan view of the vias of the circuit board of FIG. 5B that are in communication with an underlying ground layer of the circuit board. FIG. 5B also defines bores in the circuit board that are sized and shaped to accept pins of the connectors such that, when the connector is mounted thereon portions of the circuit board, there will be correct registration of the respective electrical traces and ground pins with the connector.

Figure 6:
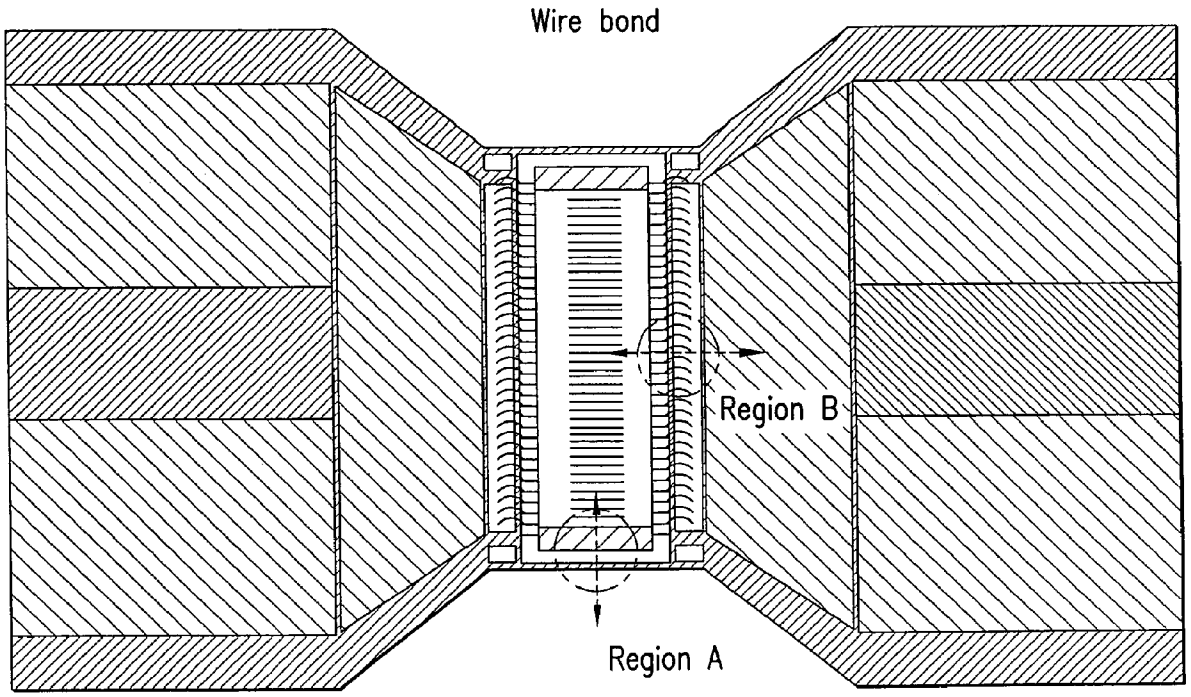
FIG. 6 is a top plan view of a portion of the exemplified circuit board showing, in Region A, the ground electrode layer of the transducer wire bonded to an electrical trace on the interposer, which is, in turn, wire bonded to ground pads of the circuit board, and further showing, in Region B, the individual electrical traces of the transducer wire bonded to individual board electrical traces of the circuit board.
Figure 7A:
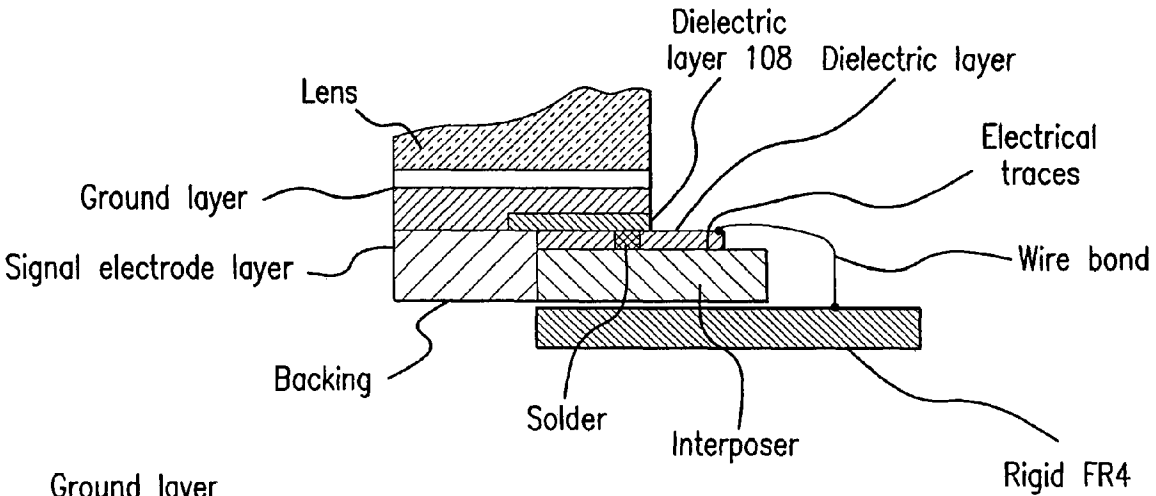
FIG. 7A is a partial enlarged cross-sectional view of Region A of FIG. 6, showing the dielectric layer positioned about the solder paste ball bumps and between the PZT stack and the interposer.
Figure 7B:
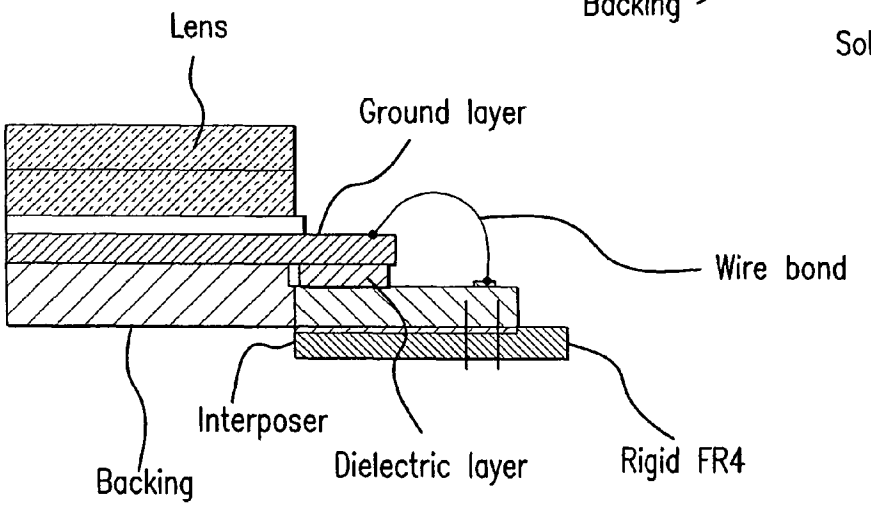
FIG. 7B is a partial enlarged cross-sectional view of Region B of FIG. 6, showing the dielectric layer between the PZT stack and the interposer.
Figure 8A:
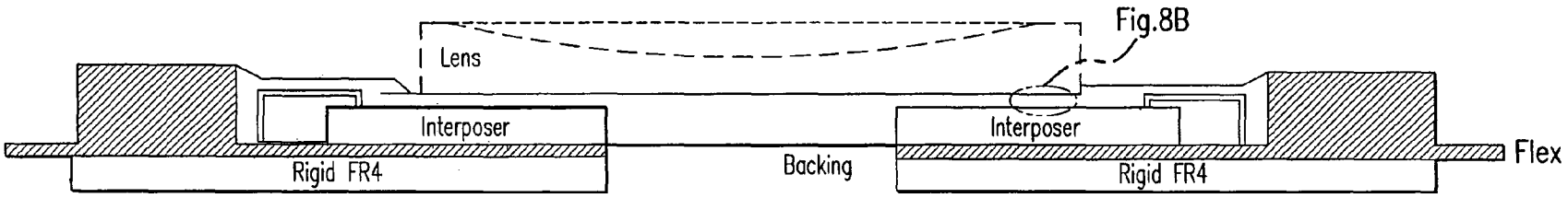
FIGS. 8A and 8B are partial cross-sectional views of an exemplified transducer mounted to a portion of the circuit board.
Figure 8B:
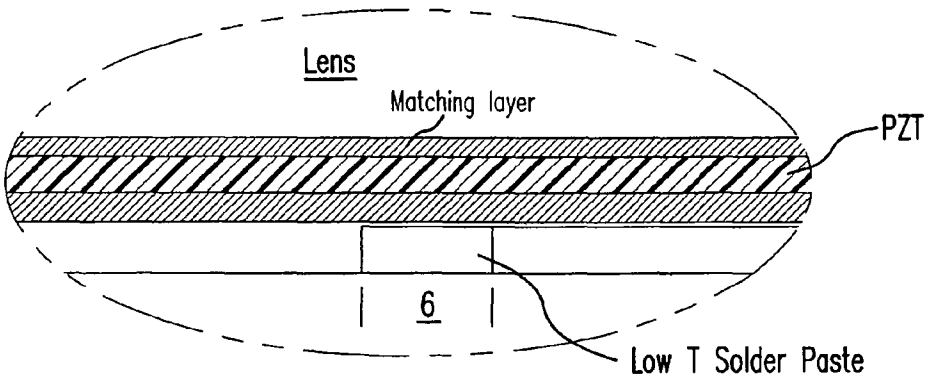
Figure 9:
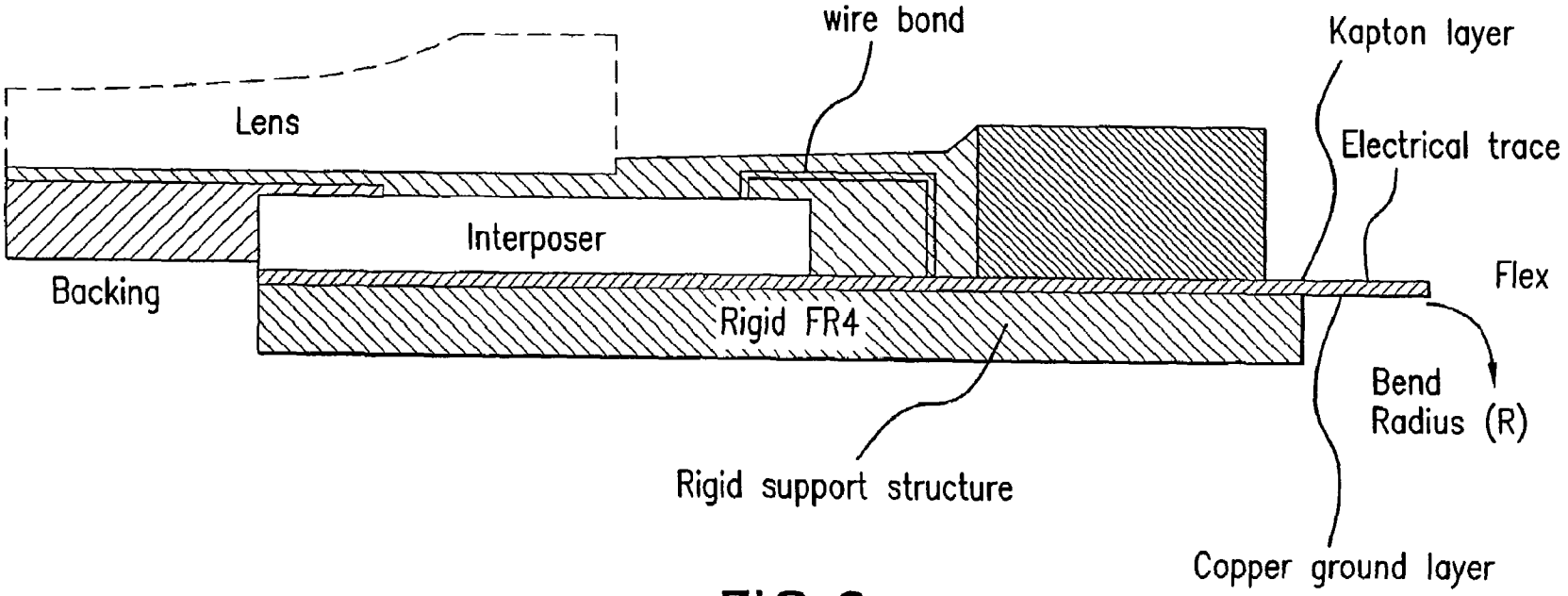
FIG. 9 is an enlarged partial view Region B of an exemplified transducer mounted to a portion of the circuit board.
Figure 10:
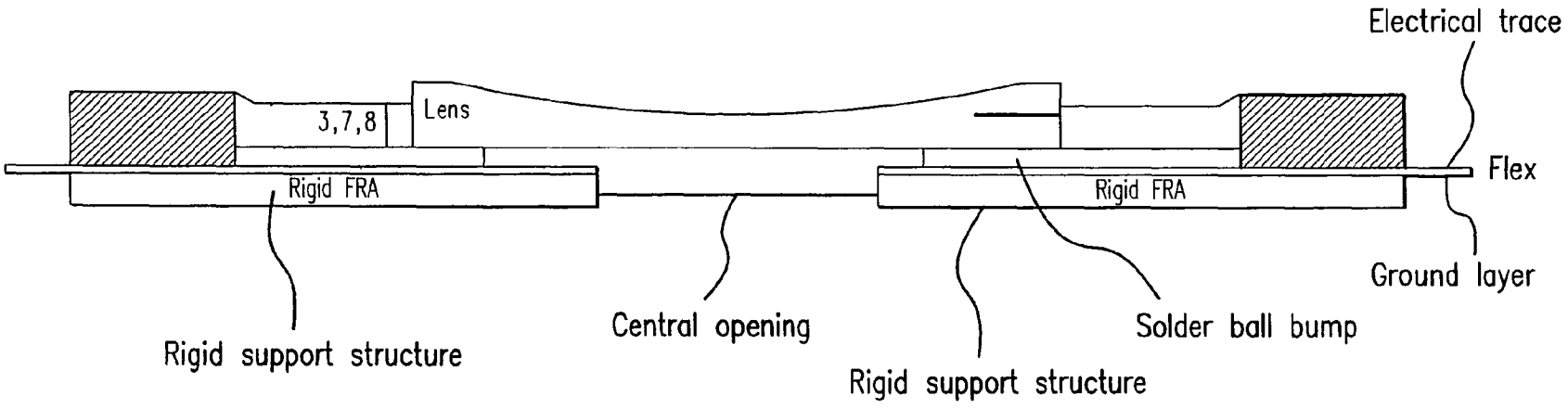
FIG. 10 is a partial enlarged cross-sectional view of a transducer that does not include an interposer, showing a solder paste ball bump mounted thereon the underlying circuit board, each ball bump being mounted onto one board electrical trace of the circuit board, and showing the PZT stack being mounted thereon so that the respective element signal electrodes of the PZT stack are in electrical continuity, via the respective ball bumps, to their respective board electrical trace of the circuit board.

FIG. 6 illustrates a partial enlarged top plan view of a portion of the exemplified circuit board showing, in Region A, the ground electrode layer of the transducer being wire bonded to an electrical trace on the interposer, which can be, in turn, wire bonded to ground pads of the circuit board. The ground pads of the circuit board are in communication, through vias in the Kapton™ layer, with the underlying bottom copper ground layer. As illustrated, in Region B, the individual electrical traces of the transducer are wire bonded to individual board electrical traces of the circuit board. Referring now to FIG. 8A, in one aspect the central opening of the circuit board underlies the backing material of the transducer. FIG. 7A is an enlarged partial view Region B of an exemplified transducer mounted to a portion of the circuit board.

Figure 11B:
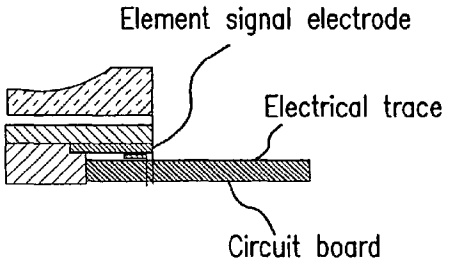
FIG. 11B is a partial enlarged cross-sectional view of FIG. 10, showing the ball bump disposed therebetween and in electrical communication with the electrical trace of the circuit board and the element signal electrode of the PZT stack.
Figure 11A:
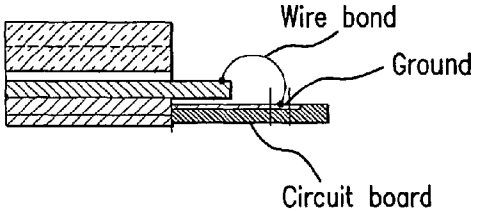
FIG. 11A is a partial enlarged cross-sectional view of FIG. 10, showing the ground electrode layer of the transducer without an interposer wire bonded to ground pads of the circuit board.

Referring now to FIGS. 11A-11B, a transducer mounting is shown that does not include an interposer to the substantially rigid central portion of the circuit board. This embodiment allows for the elimination of most of the wire bonds. In this aspect, the PZT stack is surface mounted onto the circuit board directly by, for example, means of a series of gold ball bumps. The gold ball bump means is a conventional surface mounting technique and represents another type of surface mounting techniques consistent with the previously mentioned surface mounting techniques. In this example, the rigidized central portion of the circuit board can provide the same functionality as the interposer. Wire bonds, or other electrical connection, from the ground electrode of the PZT stack to the ground of the circuit board are still required to compete the signal return of the assembled device. FIG. 11A shows the ground electrode layer of the transducer (without interposer) wire bonded to the ground pads of the circuit board.

In one aspect, the gold ball bumps are applied directly onto the circuit board. Each ball bump is positioned in communication with one electrical trace of the circuit board. When the PZT stack is applied, it is aligned with the electrical traces of the circuit board and electrical continuity is made via the ball bumps. The PZT stack is secured to the circuit board by, for example and not meant to be limiting, a) use of an underfill, such as a UV curable; b) use of an ACF tape; c) by electroplating pure Indium solder onto the electrodes of either the PZT or the circuit board and reflowing the Indium to provide a solder joint between the signal electrode on the PZT and the gold ball bump on the circuit board, and the like.

An arrayed transducer can be operatively connected to the processing unit of the system using the flex circuit as shown in FIGS. 2A-11. Referring now to FIGS. 12-15, the flex circuit can be operatively connected with a BTH connector. BTH connectors are common and are available in a variety of sizes. The BTH connector comprises a number of pins for mating with a BSH connector. The number of pins can be at least one greater than the number of array elements or traces of flex. For example, the number pins can be equal twice the number of array elements or corresponding traces of flex. Thus, in one example, 2×180=360 pins can be used for the 256 traces on the flex circuit of a 256 element array. In another example, 256 pins can be used for the exemplary 256 element array. The BSH connector can be connectively seated within the BTH. The BSH connector is operatively connected with an interface such as a printed circuit board that is terminated with a plurality of coaxial cables. A larger common cable formed from the plurality of coaxial cables can be terminated with a ZIF end for interfacing with the processing unit of the ultrasound system at a ZIF receptacle or interfacing site. One exemplary ZIF connector that can be used is a 360 Pin DLM6 ITT Cannon ZIF™ connector as available from ITT Corporation of White Plains, N.Y. As would be clear to one skilled in the art, however, alternative ZIF™ connectors can be used for interfacing with the processing unit and can have more or less than 360 pins.

The connection can comprise a cable or bundle of cables. The cable can connect each element of the array to the processing unit in a one-to-one relationship; that is, each element can be electrically connected with its own signal and a ground lead to a designated connection point in the processing unit whereby the plurality of individual element connections are bundled together to form the overall cable. Optionally, each individual electrical connection can be unbundled and not physically formed into a cable or cable assembly.

Suitable cables can be coaxial cables, twisted pairs, and copper alloy wiring. Other connection means can be via non-physically connected methods such as RF links, infrared links, and similar technologies where appropriate transmitting and receiving components are included.

The individual element connections can comprise coaxial cable of a type typically used for connection array elements to processing units. These coaxial cables can be of a low loss type. The coaxial cables typically comprise a center conductor and some type of outer shielding insulated from the center conductor and encased in an outer layer of insulation. These coaxial cables can have nominal impedances appropriate for use with an array. Example nominal impedances can be 50 ohms or more, including 50 ohms, 52 ohms, 73 ohms, 75 ohms or 80 ohms.

An exemplary medical cable for use with one or more of the ultrasound imaging systems described herein comprises a minimum of 256 coaxial cables of 40 AWG with a nominal impedance of about 75 ohms with coaxial cable lengths of about 2.0 m. The length can be less than 2.0 m or greater than 2.0 m. The medical cable jacket length can accommodate the cable length, can include additional metal sheaths for electrical shielding and can be made of PVC or other flexible materials.

Cables and the connections for connecting an array transducer to the processing unit, including those described herein can be fabricated by companies such as Precision Interconnect-Tyco Electronics (Tyco Electronics Corporation, Wilmington, Del.).

The exemplary cable, at the proximal end, can further comprise of flex/strain relief, 12 PCBs interfacing between the coaxial cables and the ZIF™ pins, a 360 Pin ITT Cannon ZIF™ connector and actuation handle (DLM6-360 type), and a shielded casing around the connector. The exemplary cable, at the distal end, can comprise of a flex/strain relief cable terminated to two PCBs, interfacing between the coaxial cables and the flex circuit board, wherein each PCB has 1 BSH-090-01-L-D-A Samtec Connector (Samtec, Inc., New Albany, Ind.) and each PCB has 75 Ohm characteristic impedance traces with cables terminated from both sides of the PCB in a staggered layout.

The cable can use a "flex circuit" method of securing and connecting a plurality of coax cables which comprise the large cable. In an exemplary embodiment, the array has 256-elements. The array is mounted in the central region of a flex circuit. The flex circuit has two ends such that the odd numbered elements 1,3,5,7 . . . 255 are terminated on the left end of the flex with a BTH-090 connector labeled J1, and that the even numbered elements 2,4,6,8 . . . 256 are terminated on the right end of the flex with a BTH-090 connector labeled J3. For both ends, the elements are terminated in sequence along the upper and bottom rows of their respective connectors with GND (signal return) pins evenly dispersed across the connector in a repeated pattern.

The repeat pattern is defined from the outer edge of the flex towards the central region of the flex and is as follows:

2 signal pins, GND
3 signal pins, GND
2 signal pins, GND
3 signal pins . . .
. . . , GND 3 signal pins, GND
2 signal pins, GND
2 signal pins, GND.

Figure 12A:
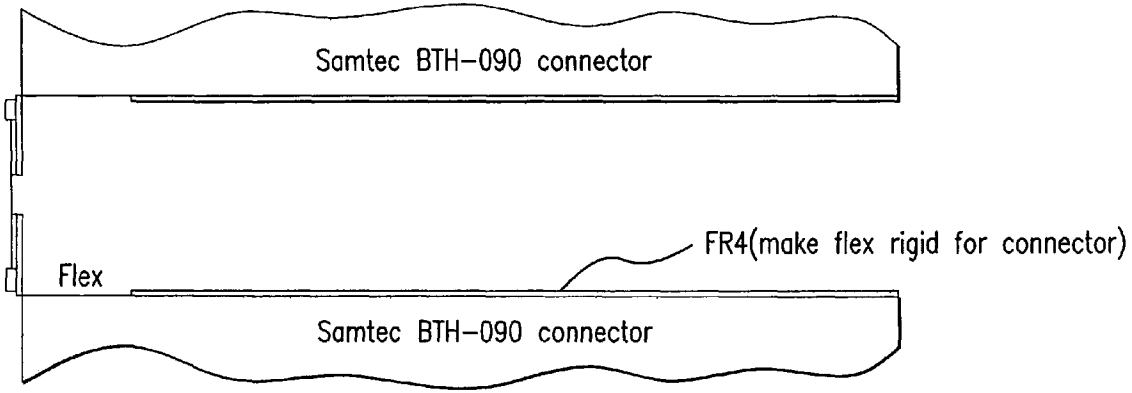
FIG. 12A is a schematic showing the flex circuit board and a pair of Samtec BTH-090 connectors mounted to a rigid portion of the circuit board.

A schematic showing a side view of the folded flex circuit, with the array mounted in the central array of the flex is shown in FIG. 12A and an associated pin out table for the connectors on the flex circuit is shown in FIG. 12B.

The flex circuit can be connected to the exemplary cable described above. The flex circuit can be connected to a Precision Interconnect-Tyco Electronics medical cable assembly. The electrical, for example, connection from the flex to the ZIF™ connector can be made through two scanhead PCBs followed by a coax cable bundle and 12 short PCBs each with a 2×15 connector inserted into ZIF™ pins.

Each scanhead PCB (total of two) can comprise one BSH-090 connector, 128 traces (all traces with controlled impedance of for example 75 Ohms at 30 MHz) and can be terminated with 128 (40 AWG 75 Ohm) coax cables. The PCB can have outer dimensions of 0.525" by 2.344."

Figure 13:
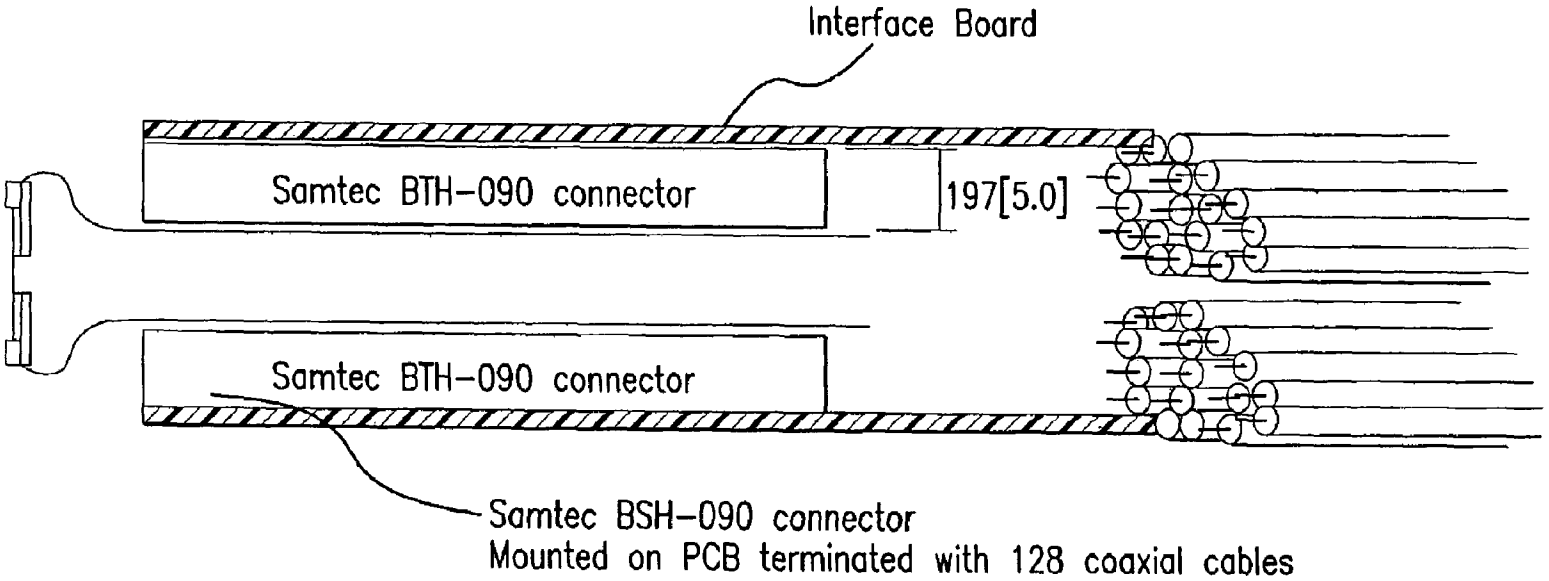
FIG. 13 is a schematic showing a side view of the individual coaxial cables that are to be operatively coupled to the pair of Samtec BTH-090 connectors on the flex circuit board via a pair of BSH-090 connectors.
Figure 14:
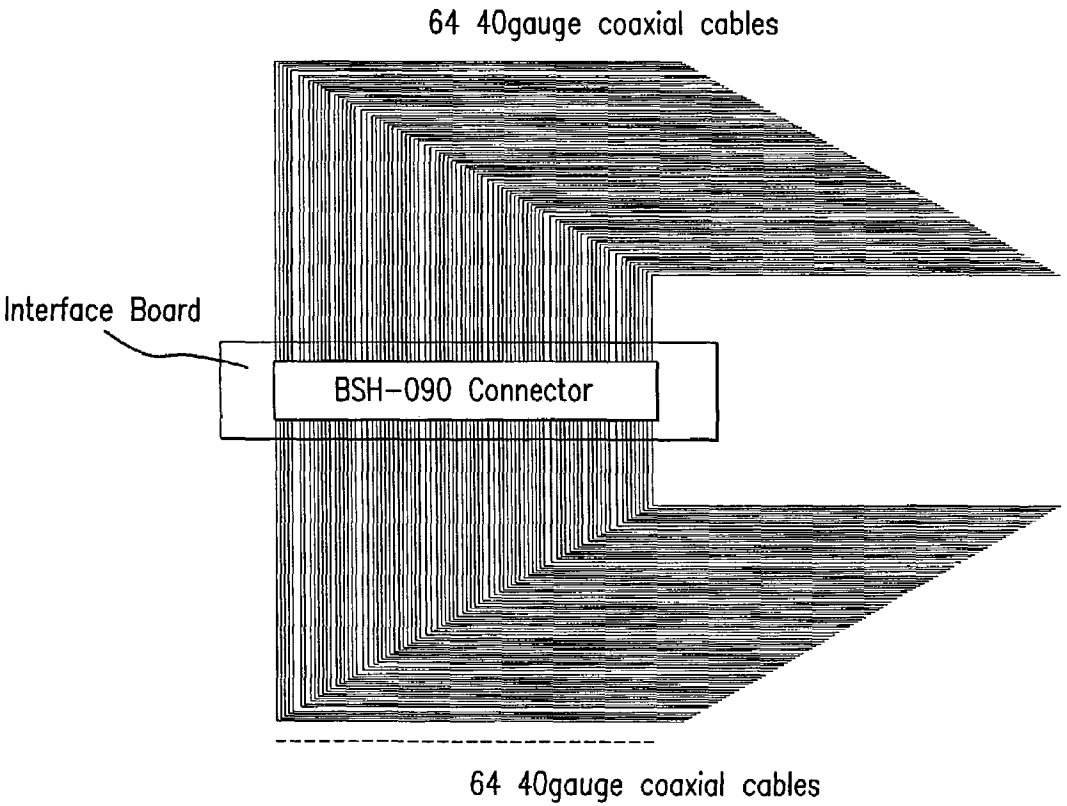
FIG. 14 is a schematic showing an exemplary plan view of half of the coaxial leads therein the cable connected to one of the BSH-090 connectors.

FIG. 13 illustrates the design of the two scanhead PCBs. FIG. 14 illustrates how the PCBs can be connected to the flex circuit and illustrates the staggered nature of how the coax cable ribbons can be soldered to the PCB. There are two scanhead PCBs. The left board can be connected to the J1 connector on the flex and the right board can be connected to the J3 connector. Each scanhead PCB can have one BSH-090 connector. The pin-out for each scanhead trace can be matched to the pin out for the J1 and J3 connector.

ZIF Connector

Figure 15A:
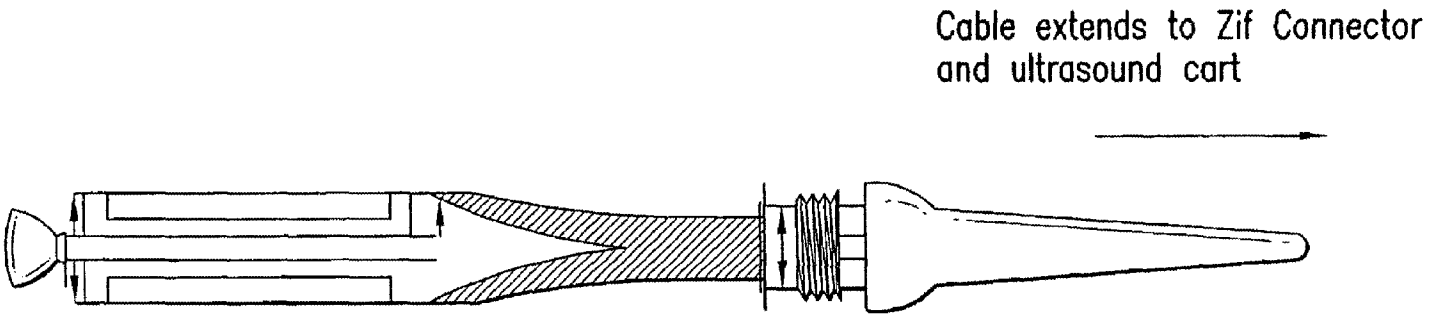
FIG. 15A is an illustration of an exemplary plan view of the distal end of a medical cable assembly connected to the folded flex circuit board, the cable's proximal end (not shown) may include a multi-pin ZIF connector that interfaces with the ultrasound system and may be used to practice one or more aspects of the present invention.

An exemplary medical cable, as partially shown in FIG. 15A, comprises a ZIF connector on the proximal end, the end of the cable which connects to the processing unit. One skilled in the art will appreciate that several designs of cable assemblies are possible. FIG. 15B illustrates a pin out that can be used for the exemplary ZIF Connector. The pins labeled as G are signal return pins. The pins labeled as N/C are not terminated with coaxial cables and these pins are reserved to be used as either for shielding to chassis ground or for other unspecified functions. The N/C pins can be accessible by simply removing the ZIF housing and soldering to the unused traces on any of the 12 PCBs connected to the ZIF.

The 12 individual PCBs used to connect to the ZIF connector have coax cables connected on one or both sides of the board. One edge of the PCB can have a connector suitable for insertion into the ZIF connector (Samtec SSW or equivalent) and each PCB shall have the appropriate traces and vias required to connect the correct coaxial cable to the correct ZIF pin. Each PCB can have a Samtec SSW, or equivalent, connector with two rows of 15 pins, although the number of coax cables may differ on some of the 12 PCBs as defined in the FIG. 15B. The general layout of the pins on the 2×15 connector is universal and is shown in Table 1.

One of the 12 PCBs requires provisions in the trace layout to include an EEPROM as defined in FIG. 15B. Two of the 12 PCBs require some of the pins to be terminated as required to provide the hard-coded PROBE ID number that will identify the particular array design included inside the array assembly.

Various connection methods can be used including connectors of various styles. For these various connection methods, the impedance can be 75 Ohms at a center frequency of 30 MHz.

TABLE 1

The layout of connections on the connector end of the ZIF PCB that plugs into the ITT Connector. General Pattern

| | |
|---|---|
| Signal | Signal |
| Signal | GND |
| Signal | Signal |
| GND | Signal |
| Signal | Signal |
| Signal | Signal |
| Signal | GND |
| Signal | Signal |
| GND | Signal |
| Signal | Signal |
| Signal | Signal |
| Signal | GND |
| Signal | Signal |
| GND | Signal |
| Signal | Signal |

Ultrasound System

Figure 16:
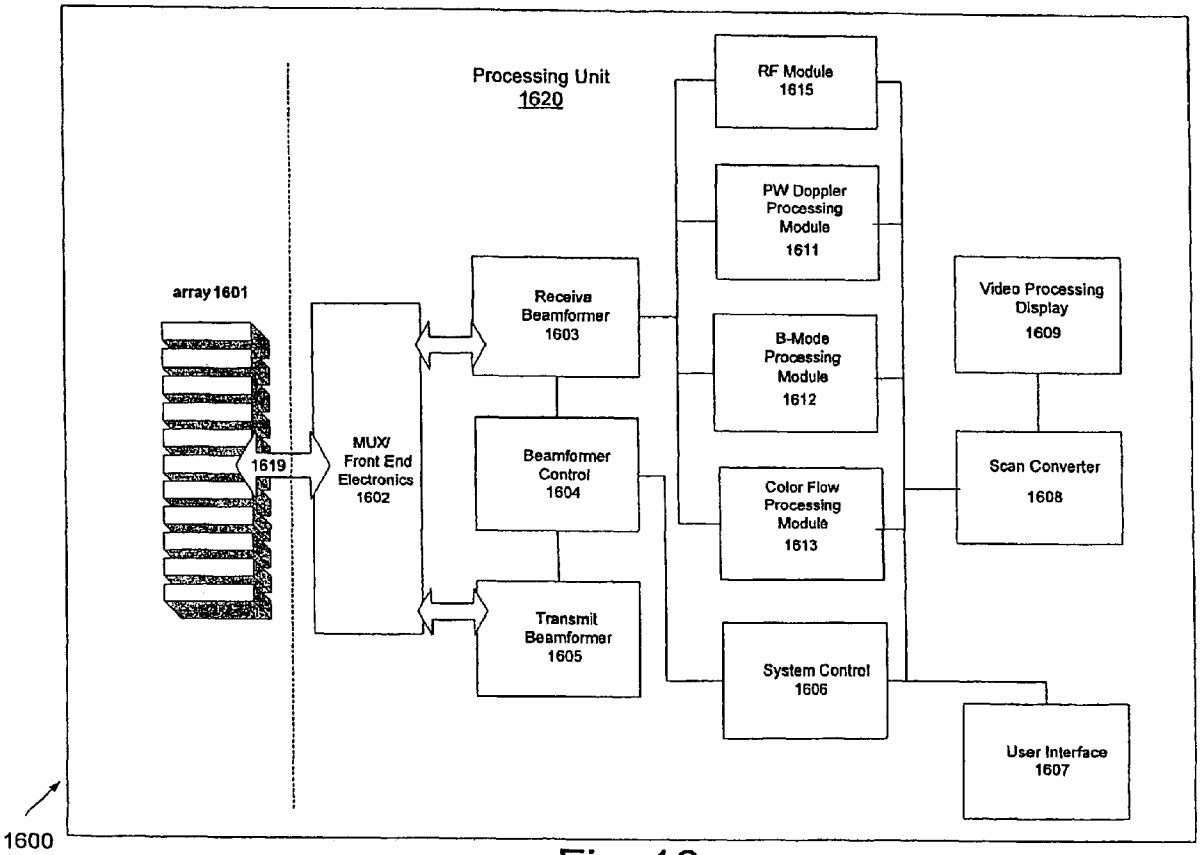
FIG. 16 is a block diagram illustrating an exemplary high frequency ultrasonic imaging system.

An exemplary embodiment of an ultrasound system 1600 according to the present invention is shown in FIG. 16. FIG. 16 is a block diagram illustrating an exemplary high frequency ultrasonic imaging system 1600. The blocks shown in the various Figures can be functional representations of processes that take place within an embodiment of the system 1600. In practice, however, the functions may be carried out across several locations or modules within the system 1600.

The exemplary system 1600 comprises an array transducer 1601, a cable 1619, and a processing unit 1620. The cable 1619 connects the processing unit 1620 and the array transducer 1601. The processing unit may comprise software and hardware components. The processing unit can comprise one or more of a multiplexer(MUX)/front end electronics 1602, a receive beamformer 1603, a beamformer control 1604, a transmit beamformer 1605, a system control 1606, a user interface 1607, a scan converter 1608, a video processing display unit 1609, and processing modules including one or more of a M-mode processing module (not shown), a PW Doppler processing module 1611, a B-mode processing module 1612, a color flow processing module 1613, a 3-D mode processing module (not shown), and a RF mode processing module 1615. The center frequency range of the exemplary system can be about 15-55 MHz or higher. When measured from the outside edge of the bandwidths, the frequency range of the exemplary system can be about 10-80 MHz or higher.

The array transducer 1601 interfaces with the processing unit 1620 at the MUX/front end electronics (MUX/FEE) 1602. The MUX portion of the MUX/FEE 1602 is a multiplexer which can electronically switch or connect a plurality of electrical paths to a lesser number of electrical paths. The array transducer 1601 converts electrical energy to ultrasound energy and vice versa and is electrically connected to the MUX/FEE 1602.

The MUX/FEE 1602 comprises electronics which generate a transmit waveform which is connected to a certain subset of the elements of the array, namely the elements of the active aperture. The subset of elements is called the active aperture of the array transducer 1601. The electronics of the MUX/FEE 1602 also connects the active aperture of the array to the receive channel electronics. During operation, the active aperture moves about the array transducer 1601, in a manner determined by components described herein.

The MUX/FEE 1602 switchably connects the elements of the active aperture to transmit and receive channels of the exemplary system. In an exemplary 256-element array transducer embodiment of the invention, there are 64 transmit channels and 64 receive channels that can be switchably connected to the active aperture of up to 64 elements. The up to 64 elements of the active aperture are contiguous. In certain embodiments of the invention, there is a separate transmit MUX and a separate receive MUX. Other embodiments of the invention share the MUX for both the transmit channels and the receive channels.

During a transmit cycle of the exemplary ultrasound system 1600, the front end electronics portion of the MUX/FEE 1602 supply a high voltage signal to the elements of the active aperture of the array transducer 1601. In one aspect, the front end electronics can also provide protection circuitry for the receiver channels to protect them from the high voltage transmit signal, as the receive channels and the transmit channels have a common connection point at the elements of the array transducer 1601. The protection can be in the form of isolation circuitry which limits the amount of transmit signal that can leak or pass into the receive channel to a safe level which will not cause damage to the receive electronics. Characteristics of the MUX/FEE 1602 include a fast rise time on the transmit side, and high bandwidth on the transmit and receive channels.

The MUX/FEE 1602 passes signals from the transmit beamformer 1605 to the array transducer 1601. In an exemplary embodiment, the transmit beamformer 1605 generates and supplies separate waveforms to each of the elements of the active aperture. In an exemplary embodiment, the waveform for each element of the active aperture is the same. In another aspect, the waveforms for each element of the active aperture are not all the same and in some embodiments have differing center frequencies.

In one exemplary embodiment, each separate transmit waveform has a delay associated with it. The distribution of the delays for each element's waveform is called a delay profile. The delay profile is calculated in a way to cause the desired focusing of the transmit acoustic beam to the desired focal point. In certain embodiments, the transmit acoustic beam axis is perpendicular to the plane of the array 1601, and the beam axis intersects the array 1601 at the center of the active aperture of the array transducer 1601. The delay profile can also steer the beam so that it is not perpendicular to the plane of the array 1601. In an exemplary aspect of the present invention, a delay resolution of 1/16 can be used. Or, in other words, 1/16 of the period of the center frequency of the transmit center frequency, though other delay resolutions are contemplated within the scope of this invention. For example at a 50 MHz center frequency, the period is 20 nanoseconds, so 1/16 of that period is 1.25 nanoseconds, which is the exemplary delay resolution used to focus the acoustic beam. It is to be appreciated that the delay resolution may be different than $1/16^{th}$ of a period, for example delay resolutions less than $1/16^{th}$ (e.g., 1/24, 1/32, etc) as well as delay resolutions greater than 1/16 (e.g., 1/12, 1/8, etc.) are contemplated within the scope of this invention.

The receive beamformer 1603, can also be connected to elements of the active aperture of the array transducer 101 via the MUX/FEE 1602. During transmit an acoustic signal penetrates into the subject and generates a reflected signal from the tissues of the subject. The reflected signal is received by the elements of the active aperture of the array transducer 1601 and converted into an analog electrical signal emanating from each element of the active aperture. The electrical signal is sampled to convert it from an analog to a digital signal in the receive beamformer 1603. Embodiments of the invention use quadrature sampling for digitization of the received signal. During the receive cycle of the system 1600, the array transducer 1601 also has a receive aperture that is determined by the beamformer control 1604, which tells the receive beamformer 1603 which elements of the array to include in the active aperture and what delay profile to use. The receive beamformer 1603 of the exemplary embodiment is a digital beamformer.

The receive beamformer 1603 introduces delays into the received signal of each element of the active aperture. The delays are collectively called the delay profile. The receive delay profile can be dynamically adjusted based on time-of-flight—that is, the length of time that has elapsed during the transmission of the ultrasound into the tissue being imaged. The time-of-flight is used to focus the receive beamformer to a point of focus within the tissue. In other words, the depth of the receive beam is adjusted using a delay profile which incorporates information pertaining to the time-of-flight of the transmitted beam.

The received signal from each element of the active aperture is summed wherein the sum incorporates the delay profile. The summed received signal flows along the receive channel from the receive beamformer 1603 to one or more of the processing module(s) 1611, 1612, 1613, and/or 1615, including those not shown in FIG. 16), as selected by the user interface 1607 and system controls 1606, which act based upon a user input.

The beam former control 1604 is connected to the MUX/FEE 1602 through the transmit beamformer 1605 and the receive beamformer 1603. It is also connected to the system control 1606. The beamformer control 1604 provides information to the MUX/FEE 1602 so that the desired elements of the array transducer 1601 are connected to form the active aperture. The beamformer control 1604 also creates and sends to the receive beamformer 1603 the delay profile for use with the reception of a particular beam. In embodiments of the invention, the receive delay profile can be updated repeatedly based upon the time of flight. The beamformer control 1604 also creates and sends to the transmit beamformer 1605 the transmit delay profile.

The system control 1606 operates in a manner known to one of ordinary skill in the art. It takes input from the user interface 1607 and provides the control information to the various components of the system 1600 in order to configure the system 1600 for a chosen mode of operation. The scan converter 1608 operates in a manner known in the art and takes the raw image data generated from the one or more of the processing modules and converts the raw image data into an image that can be displayed by the video processing/display 1609. For some processing modes of operation, the image can be displayed without using the scan converter 1608 if the video characteristics of the image are the same as those of the display.

The processing modules, except as noted herein, function in a manner known to one of ordinary skill in the art. For the PW Doppler module 1611 and the color flow processing module 1613, the pulse repetition frequency (PRF) can be high due to the high center frequencies of embodiments of this invention. The maximum unaliased velocities which may be measured are proportional to the PRF and inversely proportional to the transmit center frequency. The PRFs required to allow for the unaliased measurement of specific velocities given specific transmit center frequencies may be calculated in a method known to one of ordinary skill in the art. Given that the transmit center frequencies used are in the range of 15 to 55 MHz, or higher, and the blood flow velocities can be as high as 1 m/s and in some cases greater than 1 m/s unaliased measurement of the Doppler signal resulting from those velocities will require the PRF for PW Doppler to be up to 150 KHz. Embodiments of the invention have a PW Doppler mode which supports PRFs up to 150 KHz, which for a center frequency of 30 MHz allows for unaliased measurement of blood velocities up to 1.9 m/s in mice with a zero degree angle between the velocity vector of the moving target and the ultrasound beam axis.

In certain embodiments, the RF module 1615 uses interpolation. If the sampling method used is quadrature sampling, then the RF signal may be reconstructed from the quadrature baseband samples by zero padding and filtering, as would be known to one of ordinary skill in the art. If Nyquist sampling is used, then no reconstruction is required since the RF signal is sampled directly. In certain embodiments, the RF module 1615 reconstructs the RF signal from the quadrature samples of the receive beamformer output. The sampling takes place at the center frequency of the receive signal, but in quadrature, giving a baseband quadrature representation of the signal. The RF signal is created by first zero padding the quadrature sampled data stream, with the number of zeros determined by the desired interpolated signal sample rate. Then, a complex bandpass filter is applied to the zero padded data stream, which rejects the frequency content of the zero padded signal that is outside the frequency band from fs/2 to 3 fs/2, where fs is the sample frequency. The result after filtering is a complex representation of the original RF signal. The RF signal is then passed on to the main computer unit for further processing such as digital filtering and envelope detection and display. The real part or the complex representation of the RF signal may be displayed. For example, the RF data acquired for a particular scan line may be processed and displayed. Alternatively, RF data from a certain scan line averaged over a number of pulse echo returns can be displayed, or RF data acquired from a number of different scan lines can be averaged and displayed. The scan lines to be used for acquisition of the RF data can be specified by the user based on evaluation of the B-Mode image, by placing cursor lines overlaid on the B-Mode image. A Fast Fourier Transform (FFT) of the RF data can also be calculated and displayed. The acquisition of RF data and the acquisition of B-Mode data can be interleaved so as to allow for the display of information from both modes concurrently in real time. The acquisition of physiological signals such as the ECG signal can also occur concurrently with the acquisition of RF data. The ECG waveform can be displayed while the RF data is acquired. The timing of the acquisition of RF data can be synchronized with user defined points within the ECG waveform, thereby allowing for the RF data to be referenced to specific times during a cardiac cycle. The RF data can be stored for processing and evaluation at a later time.

FIG. 17 shows a block diagram of the system 1600 further illustrating components of an embodiment of the invention. The array transducer 1601 is connected to the front end transformer 1702 via a cable 1619. The cable 1619 comprises signal pathways from the elements of the array transducer 1601 to the front end transformers 1702. An exemplary embodiment of the cable is described herein and comprises individual micro-coax cables. In addition, connectors can be used on one or both ends of the cable 1619. In one aspect of the invention, a connector with pins equal to twice the number of elements can be used and an exemplary connector is described herein. For each element of the array transducer 1601 a signal and a ground path can be used. In other embodiments of the invention, the ground connection is shared for a grouping of elements. Alternatively, the MUX/Front End Electronics 1702, 1703, 1704, 1708 can be located inside the housing for the linear transducer array 1601

FIG. 17 provides representative details of the circuitry for four elements of the array transducer 1601 as examples for the larger system 1600 wherein there is a front end transformer 1702 and transmit output stage 1703 for each element. For an embodiment with a 256 element array transducer 1601, there are 256 front end transformers 1702 and transmit output stages 1703. The front end transformers 1702 and transmit output stages 1703 are more fully described below. During receive, the electrical signal from an element of the array transducer 1601 passes through the front end transformer 1702 into the receive multiplexer 1704. The receive multiplexer 1704 selects which element and front end transformer are connected to the receive channel 1705. The receive channel 1705 comprises a low noise amplifier and a time gain control, both more fully described below. The signal then passes from the receive channel 1705 into the analog-to-digital conversion 1706 module where it is digitized. The digital received signal then passes into the receive beamformer 1707, which is a digital beamformer. In block 1707, a delay profile generated in the beamformer control is applied to the received signal. The signal from the received beamformer 1707 travels into the synthetic aperture memory 1710. The synthetic aperture memory adds the received data from two successive ultrasound lines. An ultrasound line is considered to be the data resulting from returning ultrasound echoes that is received after the transmission of an ultrasound pulse into tissue. Synthetic aperture imaging performs as one of ordinary skill in the art would understand. In part, synthetic aperture imaging refers to a method of increasing the effective size of the transmit or receive aperture. For example, if there are 64 channels in the beamformer, during the reception of one line of ultrasound data, up to 64 transmit channels and 64 receive channels can be used. Synthetic aperture imaging will use two lines of ultrasound data, added together. The first ultrasound line can be acquired with a receive aperture which can span elements 33 to 96. The second ultrasound line is received with an aperture segmented into two blocks, located at elements 1 to 32 and 97 to 128. Both ultrasound lines use the same transmit aperture. When the 2 ultrasound lines are summed, the resulting ultrasound line is essentially the same as that which would have been received had the receive aperture consisted of 128 channels located at elements 1 to 128, provided that there is no appreciable motion of the tissue being imaged during the time required to acquire the two lines of ultrasound data. In this instance two ultrasound lines were required rather than just one, so the frame rate is lowered by a factor of two. The two receive apertures can be arranged in a different way, as long as together they form a 128 element aperture. Alternatively, the transmit aperture size can be increased while keeping the receive aperture the same. More than 2 ultrasound lines can be used to increase the aperture by more than a factor of two. The signal from the synthetic aperture memory 1710 is then stored in the RF cine buffer 1713, which is a large memory that sores many received RF lines, as controlled by the asynchronous processing control module 1714. The buffered receive signal is then read into the signal processing unit 1715 at an appropriate rate. The signal processing unit 1715 may be implemented with a dedicated CPU on the beamformer control board. The received signal passes from the signal processing unit 1715 to the computer unit 1717 where it is further processed according to the mode selected by the user. The processing of the received signal by the computer unit 1717 is generally of the type known to a person of ordinary skill in the art, with exceptions as noted herein.

In one embodiment, as shown in FIG. 17, the computer unit 1717 comprises system software configured to process signals according to the operation mode of the system. For example, the system software in the main computer unit 1717 may be configured to carry out B-Mode processes which may include, for example, preprocessing; persistence processing; cineloop image buffer; scan conversion; image pan; zoom and postprocessing. The system software in the main computer unit 1717 may also be configured to carry out processes for color flow imaging (CFI), which may include, for example, threshold decision matrix; estimate filtering; persistence and frame averaging; cineloop CFI image buffer; scan conversion; color maps and priority. The system software in the main computer unit 1717 may also be configured to carry out processes for PW Doppler, which may include, for example spectral estimation (FFT); estimate filtering; cineloop spectral data buffer; spectral display generation; postprocessing and dynamic range and audio processing.

The embodiment of the system of FIG. 17 is also comprised of a user interface panel 1720. In this embodiment the user interface panel 1720 is similar to the standard user interface found on most clinical ultrasound systems. For example, the B-Mode user interface may have image format controls that include image depth; image size; dual image activate; dual image left/right select; flip image left/right; flip image up/down and zoom. Transmit controls may include transmit power (transmit amplitude); transmit focal zone location; number of transmit zones selection; transmit frequency and number of cycles. Image optimization controls may include; B-Mode Gain; TGC sliders; preprocessing; persistence; dynamic range; frame rate/resolution control and post-processing curves.

As another example of mode-dependent interface controls, a color flow imaging user interface may have image format controls that may include color flow mode select (e.g., color flow velocity, Power Doppler, Tissue Doppler); trackball; steering angle; color box position/size select (after selection trackball is used to adjust position or size); preset recall; preset menu and invert color map. Transmit controls may include transmit power (transmit amplitude); transmit focal zone location and transmit frequency. Image optimization controls may include; color flow gain; gate size; PRF (alters velocity scale); clutter filter select; frame rate/resolution control; preprocessing select; persistence; dynamic range (for Power Doppler only) and color map select.

Yet another example of a user interface is a PW Doppler user interface which may have PW Doppler format controls that may include PW Doppler mode select; trackball; activate PW cursor (trackball is used to adjust sample volume position); sample volume size; Doppler steering angle; sweep speed; update (selects either simultaneous or interval update imaging); audio volume control and flow vector angle. Transmit controls may include transmit power (transmit amplitude) and transmit frequency. Spectral Display optimization controls may include PW Doppler gain; spectral display size; PRF (alters velocity scale); clutter filter select; preprocessing and dynamic range.

An exemplary M-Mode user interface may have image format controls including M-Mode cursor activation; trackball (used to position cursor); strip size and sweep speed. Transmit controls may include transmit power (transmit amplitude); transmit focal zone location; transmit frequency and number of cycles. Image optimization controls may include M-Mode gain; preprocessing; dynamic range and post-processing.

An exemplary RF Mode user interface may have, for example, RF line acquisition controls that may include RF line position; RF gate; number of RF lines acquired; RF region activate; RF region location; RF region size; number of RF lines in region; averaging; and B-Mode interleave disable. Transmit controls may include transmit power (transmit amplitude); transmit focal zone location; transmit f-number; transmit frequency; number of cycles; acquisition PRF and steering angle. Receive processing controls may include RF Mode gain; filter type, order; window type and number of lines averaged.

The digital samples of the received signal are processed at a rate which is generally different from the rate at which the data is acquired. Such processing is referred to herein as "asynchronous signal processing." The processing rate is the rate at which data is displayed, typically about 30 frames per second (fps.) As one would recognize, however, the data can be displayed at a rate up to the acquisition rate or can be displayed at less than about 30 fps. The data can be acquired at much faster frame rates, in certain embodiments of the invention at about 300 frames per second, or at a speed necessary to acquire the diagnostic information desired. For example, image date of a rapidly moving anatomical structures such as a heart valve can be acquired using a faster frame rate and then can be displayed at a slower frame rate. Data acquisition rates can be less than 30 fps, 30 fps, or more than 30 fps. For example, data acquisition rates can be 50, 100, 200, or 300 or more fps.

The display rate can be set such that it does not exceed that which the human eye can process. Some of the frames which can be acquired can be skipped during display, although all of the data from the receive beamformer output is stored in an RF data buffer such as the RF cine buffer 1713. The data is sometimes referred to as RF data or by the sampling method used to acquire the data, (for instance in the case of quadrature sampling, the data can also be referred to as baseband quadrature data). The quadrature or RF data is processed prior to display. The processing may be computationally intensive, so there are advantages to reducing the amount of processing used, which is accomplished by processing only the frames which are to be displayed at the display rate, not the acquisition rate. The frames that were skipped over during display can be viewed when live imaging stops or the system is "frozen." The frames in the RF buffer 1713 can be retrieved, processed, and played back at a slower rate, e.g., if the acquisition rate is 300 frames per second, the play back of every frame at 30 frames per second would be 10 times slower than normal, but would allow the operator to view rapid changes in the image. The playback feature is usually referred to as the "Cineloop" feature by persons of ordinary skill in the art. Images can be played back at various rates, or frame by frame, backwards and forwards.

The system 1600 shown in FIG. 17 can also comprise various items which one of ordinary skill in the art would recognize as being desirable for the function of the system, such as clocks 1712, memory, sound card and speakers, video card and display, etc. and other functional blocks as shown in FIG. 17.

Figure 18A:
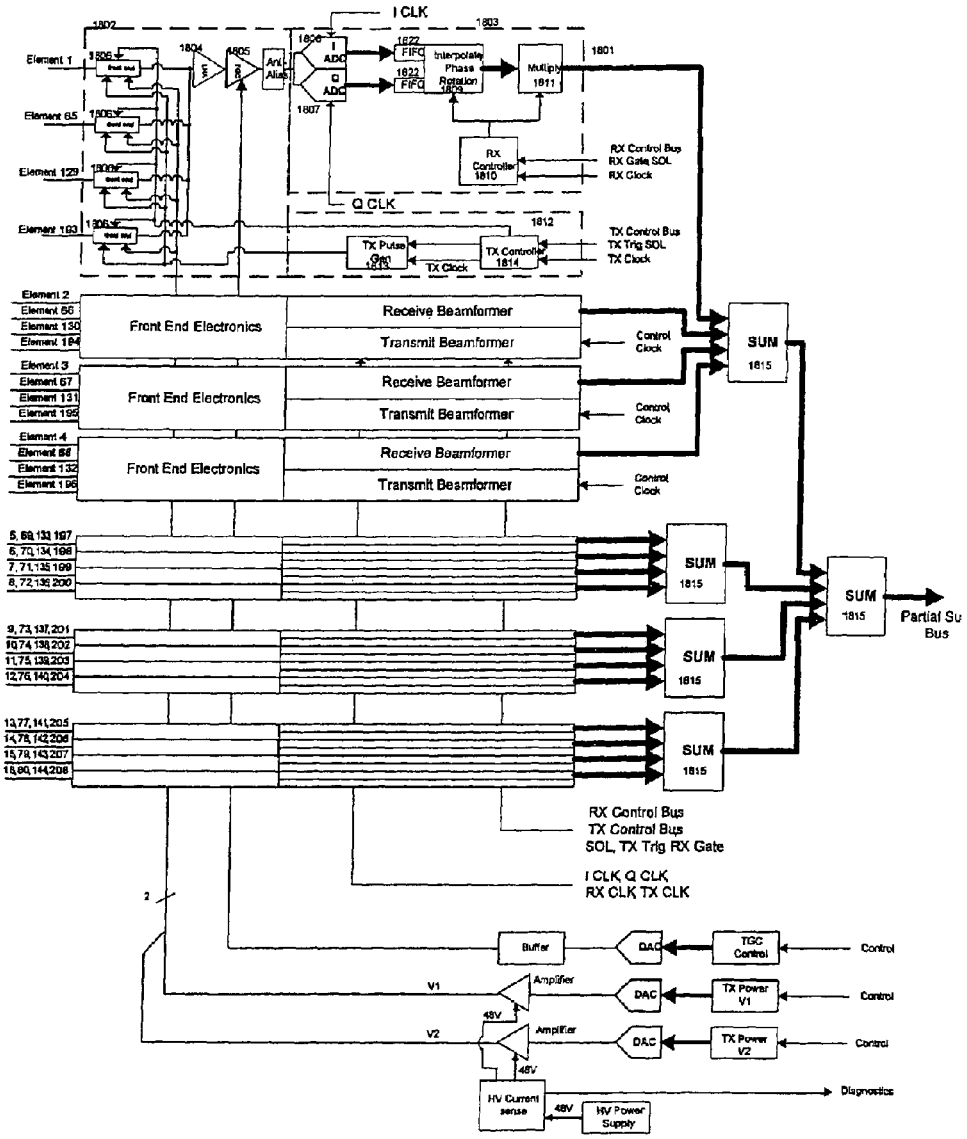
FIG. 18a is a schematic diagram illustrating exemplary receive beamformers, transmit beamformers, front end electronics, and associated components.
Figure 18B:
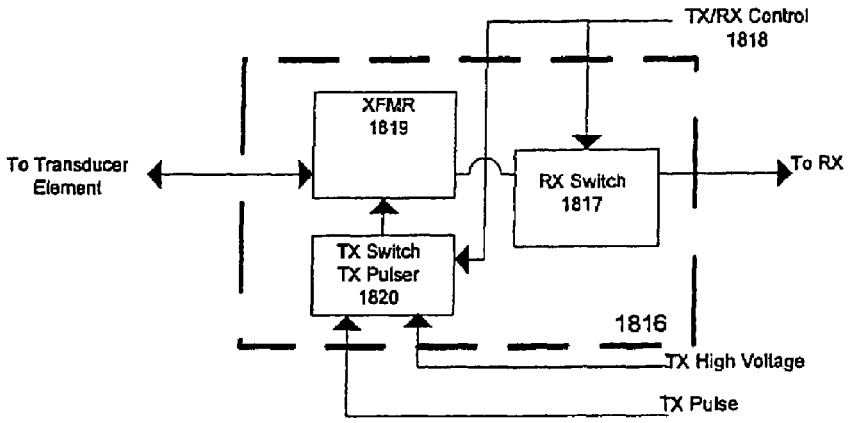

FIGS. 18a and 18b provide additional detail of an embodiment of the MUX/Front End Electronics 1702, 1703, 1704, 1708 and the receive beamformer 1707 and transmit beam former 1709 functions according to an embodiment of the present invention. In the embodiment shown in FIG. 18a, a channel, for instance a receive channel, can be connected to a node and that node is connected to, for example, four (4) elements of the array transducer 1601 through a switching circuit, or multiplexing circuit, as shown in FIG. 18a. For instance, channel 1 1801 may be switchably connected to elements numbered 1, 65, 129, and 193 in FIG. 18a so that only one of those four elements are connected to channel 1 1801 at any given time. This, in essence, is the performance of the multiplexing function of the MUX/Front End Electronics 1702, 1703, 1704, 1708 during the receive cycle of the system 1600. The assignment of four switchably connected elements to a channel is done such that contiguous elements of any given subset of elements can comprise the active aperture. For example, if the array transducer were comprised of 256 elements, then 64 or less elements can form the subset that comprises the active aperture.

The multiplexing of the elements of the array transducer 1601 for the receive cycle can be carried out by a RX switch 1817 as shown in an exemplary diagram (FIG. 18b) of the front end 1802. A control signal 1818 from the beamformer control 1711 determines which RX switch 1817 is activated, thereby connecting the chosen element of the four (4) available elements for that module 1802 to the receive channel. As one skilled in the art would appreciate, the multiplexing scheme illustrated in FIGS. 18a and 18b can be applied to transducers of varying numbers of elements (other than 256 elements) and of varying maximum active aperture sizes (other than up to 64 elements).

The exemplary front end 1816 shown in FIG. 18b also comprises the transformer 1819 and pulser 1820, which are described in more detail below. In one aspect, the front end 1816 provides isolation of the receive channel from the transmit waveform, discussed previously herein.

The received signal from the selected array transducer element passes into the low noise amplifier (LNA) 1804. From the LNA 1804, the then amplified signal passes into time gain control (TGC) 1805. Since elapsed time is proportional to the depth of the received reflected signals, this is also referred to as a depth dependent gain control. In an ultrasound system, as time goes by from the transmission of an ultrasound wave, the signal passes deeper into the tissue and is increasingly attenuated; the reflected signal also suffers this attenuation. The TGC 1805 amplifies the received signal according to a time varying function in order to compensate for this attenuation. The factors which can be used to determine the time varying TGC gain are time of flight, tissue characteristics of the subject or subject tissue under study, and the application (e.g. imaging modality). The user may also specify gain as a function of depth by adjusting TGC controls on the user interface panel 1607. Embodiments may use, for example, an Analog Devices (Norwood, Mass.) AD8332 or similar device to perform the LNA 1804 and TGC 1805 functions. From the TGC 1805, the receive signal passes into the receive beamformer 1803 where it is sampled by a sampler, in this embodiment, the analog-to-digital converters 1807 and 1808. In other embodiments according to the invention only one analog-to-digital converter is used if sampling is done at a rate greater than the Nyquist rate; for instance at 2 or 3 times the Nyquist rate, where the Nyquist rate involves sampling the ultrasound signals from the individual elements at a rate which is at least twice as high as the highest frequency in the signal.

In other embodiments of the invention, quadrature sampling is employed and two analog-to-digital converters are used, namely the "I" and the "Q" sampler. In the exemplary embodiment of the receive beamformer 1803, the receive signal is digitized in blocks 1807 and 1808 using quadrature sampling analog-to-digital converters (ADC); two ADCs are required per channel, with sampling clocks shifted 90° out of phase. The sample rate used can be the center frequency of the receive signal. For comparison, direct sampling would use a sampling rate in theory of at least twice the highest frequency component in the receive signal, but practically speaking at least three times the sampling rate is preferred. Direct sampling would use one ADC per channel.

Once sampled, the now digitized received signal passes into a Field Programmable Gate Array (FPGA) in which various functions associated with receive beamforming are implemented. Within the FPGA, the digitized received signal can undergo a correction for the DC offset of the ADC. This is implemented by the subtraction of a value equal to the measured DC offset at the ADC output. Each ADC may have a different DC offset correction value. The DC offset may be determined by averaging a number of digital samples appearing at the output of the ADC with no signal present at the receive channel input, for example, during a calibration period at system start up. The digitized signal next passes into a FIFO buffer 1822 where each sample is stored for an appropriate duration so that the appropriate delay profile can be implemented. The delay can be implemented in both coarse and fine manners. A coarse delay can be implemented by shifting the signal by one or more sample points to obtain the desired delay. For instance, if the desired delay is one sample period, then shifting by one sample in the appropriate direction provides a signal with the appropriate delay. However, if a delay of a value not equal to the sample period is desired, a fine delay can be implemented using an interpolation filter 1809.

From the FIFO buffer 1822, the digitized received signal passes into the interpolation filter 1809 for the calculation of any fine delay. The interpolation filter 1809 is used in a system where the sample period is greater than the appropriate fine delay resolution. For instance, if the sample rate is the center frequency of the ultrasound signal and is 50 MHz, the sample rate is one sample every 20 nanoseconds. However, a delay resolution of 1.25 nanoseconds (1/16 of 20 nanoseconds) is used in certain embodiments to provide the desired image quality, though other delay resolutions are contemplated within the scope of this invention. The interpolation filter 1809 is used to calculate a value for the signal at points in time other than the sampled point. The interpolation filter 1809 is applied to the in-phase and quadrature portions of the sampled signal. Embodiments of the interpolation filter 1809 comprise a finite impulse response (FIR) filter. The coefficients of each filter can be updated dynamically by the beamformer control module based on the time of flight, sample by sample. After processing by the interpolation filter, a phase rotation can be applied by a multiplier 1811 multiplying the in-phase and quadrature components by the appropriate coefficients. The phase rotation is used to incorporate into the interpolated sample the correct phase relative to the ADC sample frequency. The RX controller 1810 controls the FIFO modules and the interpolation filters. The receive delay is updated dynamically, so the interpolation filter coefficients at each channel need to change at certain intervals. The delay implemented by the FIFO also needs to change at certain intervals. Also, the receive aperture size is adjusted dynamically, so each channel becomes active at a specific time during the reception of the ultrasound signal; a channel is activated by multiplying by 1 instead of 0 at the "multiply" module 1811. The multiply module 1811 can also apply a "weight" which is a value between 0 and 1, independently to each channel in the receive aperture. This process, which is known as apodization, is known to one skilled in the art. The value by which the interpolated sample is multiplied by may vary with time, so as to implement an apodized receive aperture which expands dynamically during the reception of the ultrasound signal.

Figure 18C:
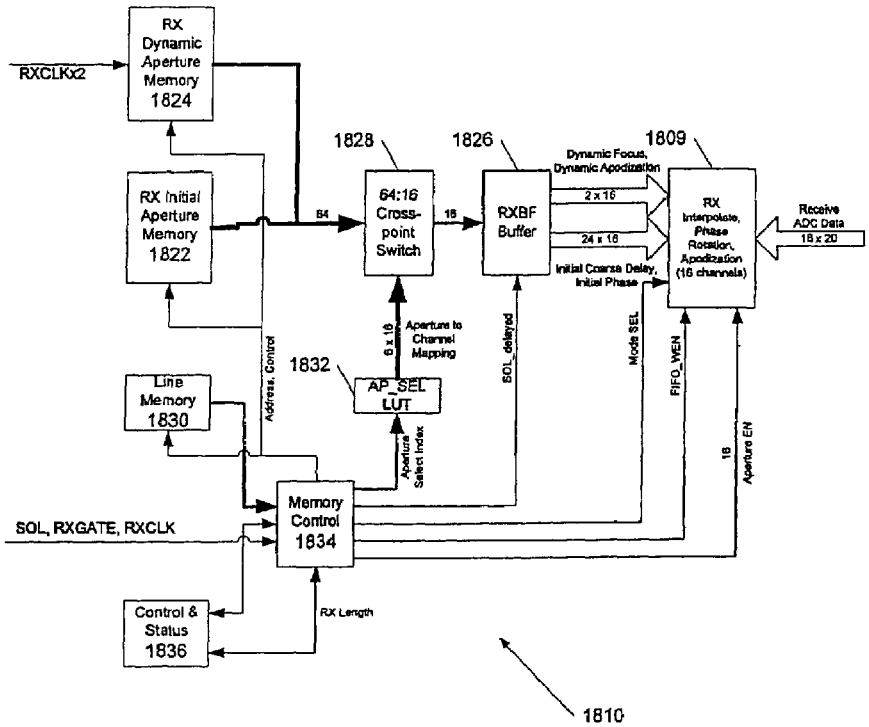
FIG. 18c is an exemplary embodiment of a receive controller (RX controller) in an embodiment according to the present invention.

FIG. 18c is an exemplary embodiment of a receive controller (RX controller) in an embodiment according to the present invention. The Receive Controller 1810 is used to program the correct delay profile, aperture size and receive apodization data into the processing block 1809 which implements the interpolation and phase rotation and apodization. The Receive Controller 1810 of FIG. 18c sets the initial parameters (Initial Coarse Delay, Initial Phase) once per start-of-line (SOL) trigger and sets the dynamic parameters (Dynamic Focus, Dynamic Apodization) once per receive clock (RXCLK) period. The initial receive delay profile is stored in RX Initial Aperture Memory 1822. The dynamic receive delay profile is stored in the RX Dynamic Aperture Memory 1824. The delay profile is loaded into the RXBF Buffer 1826 via the 64:16 Crosspoint Switch 1828 before the SOL trigger. The crosspoint switch 1828 selects 16 of the 64 aperture channel configurations. These are used to program the 16 receive channels that are on a single Channel board.

The configuration for each receive line is stored in the Line Memory 1830. Each line configuration in the Line Memory 1830 contains the Aperture Select Index, the Mode Select, and the Aperture Enable. The Aperture Select index is used to determine the Aperture to Channel mapping. The Mode Select is used to access multiple delay profiles. The Aperture Enable index controls the initial aperture size. The aperture select look-up table (AP_SEL LUT) 1832 is a method to reduce the number of possible configurations and therefore number of bits required to store in the line memory. The AP_SEL LUT 1832 is re-programmable.

The Memory Control 1834 is a state machine that decodes the line configuration. The state machine is configured by the Control and Status memory 1836. It is configured differently for different modes (e.g. B-Mode, Color Flow Mode, PW Doppler Mode, etc.). The Memory Control 1834 controls the loading of the aperture memory into the RXBF Buffer 1826 and generates the SOL_delayed and FIFO_WEN signals. The pulse SOL_delayed is used to transfer the initial delay parameters into the RX Phase Rotation and RX Apodization block 1809 in a single RXCLK period. The dynamic receive parameters are then transferred in each subsequent RXCLK period. The FIFO_WEN signal starts the receive ADC data acquisition into the FIFO for the RX interpolation filter.

The Control and Status Memory 1836 also contains common parameters such as the Receive Length. The Receive Length parameter determines how many receive samples to collect for each line.

It is to be appreciated that increasing the number of receive channels allows for larger receive apertures, which can benefit deep imaging by improving lateral resolution and penetration. The synthetic aperture mode allows for apertures greater than 64 to be used, but at the expense of a reduction in frame rate. With an increase in the number of receive channels, this can be done without a frame rate penalty.

In one embodiment according to the present invention, the receive beamformer 1803 allows for multi-line beamforming. Multi-line beamforming allows for higher frame rates by processing multiple receive lines in parallel. Frame rate increases by a factor equal to the number of parallel receive lines. Since beamforming occurs simultaneously for multiple receive apertures, higher data processing rates through the interpolation filters 1809 are used. The amount of data transferred from the receive beamformer to a host CPU would increases by a factor equal to the number of parallel receive lines. The transmit beam is broadened so that it overlaps the multiple receive lines.

The signal from each receive beamformer 1803 is then summed by summers 1815. The summed signal represents a received signal at a given time that is reflected from a given depth. The summed received signal is then routed through modules described earlier and shown in FIG. 17, to the appropriate processing module for the mode of operation selected by the user.

During the transmit operation cycle of the system 1600, selected transmit output stages are connected to the transmit channel in order to form the active aperture. In this aspect, the multiplexing is done prior to the transmit output stage. For example, as previously described, transmit channel 1 1801 can be switchably connected to the transmit output stages corresponding to elements numbered 1, 65, 129, and 193 in FIGS. 18a and 18b so that only one of those four transmit output stages are connected to transmit channel 1 1801 at any given time. It can also be seen in FIGS. 18a and 18b that transmit channel 2 can be switchably connected to the transmit output stages corresponding to elements 2, 66, 130 and 194, and so on. This is the performance of the multiplexing function of the MUX/Front End Electronics 1702, 1703, 1704, 1708 during the transmit cycle of the system.

Figure 20:
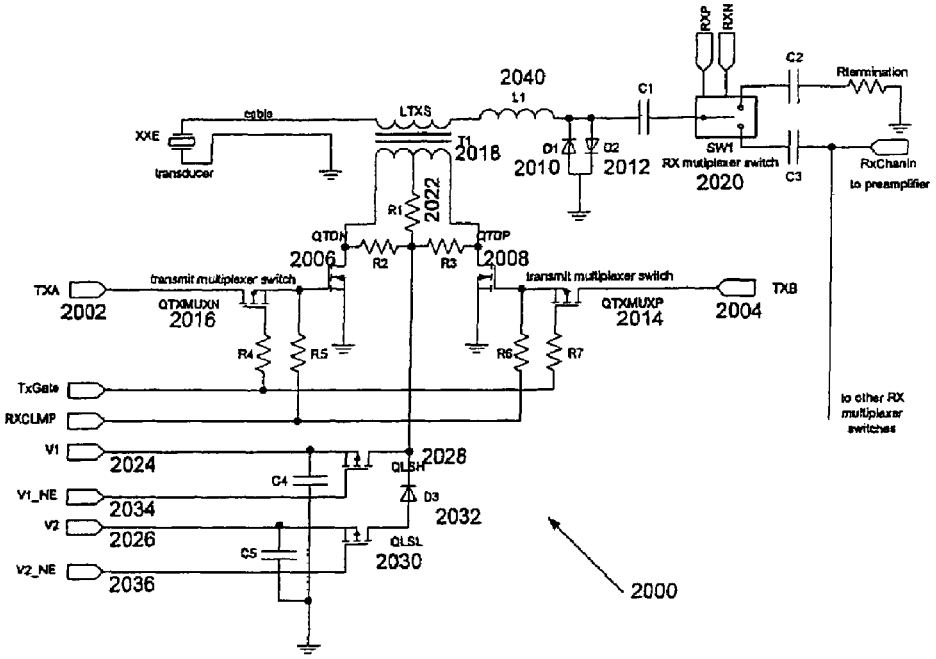
FIG. 20 is a schematic diagram of a TX/RX Switch and Pulser and related circuitry.

Referring to FIG. 20, the transmit signal which is multiplexed is the pair of signals designated by TXA 2002 and TXB 2004, which drive the gates of the transmit pulser MOSFETs QTDN 2006 and QTDP 2008 as shown in FIG. 20. These signals 2002, 2004 are unipolar signals of a sufficiently low level so that multiplexing by MOSFET type switches can be used. The assignment of four switchably connected transmit output stages to a transmit channel is done such that contiguous elements of any given subset of elements can comprise the active transmit aperture. For example, in an array transducer comprised of 256 elements, 64 or less elements can form the subset that comprises the active transmit aperture.

Optionally, the transmit multiplexing can be done after the transmit output stage using multiplexing circuitry able to accommodate a higher voltage bipolar signal.

Referring back to FIGS. 18a-18d, the transmit beamformer 1812 generates the transmit waveform with the specified delay present in the waveform in that the waveform is not sent until the appropriate time per the delay profile. The transmit waveform can be a low voltage signal, including a digital signal. Optionally the transmit waveform can be a high voltage signal used by the array transducer to convert electrical energy to ultrasound energy. The operation of the transformer 1819 and pulser 1820 are described in greater detail below.

During the process of transmit beamforming, one or more of each of the transmit channels within the active transmit aperture can produce a transmit waveform which can be delayed relative to a reference control signal. The number of transmit channels determines the maximum transmit aperture size. The benefit of increasing the number of transmit channels is improved lateral resolution and penetration for deep imaging. In various embodiments, the array transducer has 64 transmit channels or may have 96 or 128 transmit channels. The delays can vary from channel to channel, and collectively the delays are referred to as the transmit delay profile. Transmit beamforming may also include the application of a weighting function to the transmit waveforms, a process known to one of ordinary skill in the art as "apodization." Transmit apodization uses independent control of the amplitude of the transmitted waveform at each channel. The benefit to image quality is improved contrast resolution due to a reduction in spurious lobes in the receive beam profile, which can be either side lobes or grating lobes. Each transmitter output stage can have an independently controlled supply voltage, and control hardware.

Transmit waveshaping involves the generation of arbitrary waveforms as the transmit signal, i.e., the modulation of amplitude and phase within the transmit waveform. The benefit is an improvement to axial resolution through shaping of the transmit signal spectrum. Techniques such as coded excitation can be used to improve penetration without loss of axial resolution.

The transmit beamformer 1812 described herein may be implemented in one embodiment with an FPGA device. A typical implementation of a transmit beamformer 1812 which provides a delay resolution of, for example, 1/16 the transmit clock period may require a clock which is 16 times the transmit clock frequency. For the frequency range of the system described here, this would imply a maximum clock frequency of 16 times 50 MHz, or 800 MHz, and a typical FPGA device may not support clock frequencies at that rate. However, the transmit beamformer 1812 implementation described below uses a clock frequency within the FPGA of only eight (8) times the transmit clock frequency.

Each channel of the transmit beamformer is comprised of a TX controller 1814 and a Tx pulse generator 1813. The TX controller 1814 uses a parameter called, for example, an ultrasound line number (also known as a ray number), to select the active transmit aperture through the appropriate configuration of the transmit multiplexer. The ray number value identifies the origin of the ultrasound scan line with respect to the physical array. Based on the ray number, a delay value is assigned to each transmit channel in the active transmit aperture. The TX pulse generator 1813 generates a transmit waveform for each transmit channel using waveform parameters and control signals as described herein.

Figure 18D:
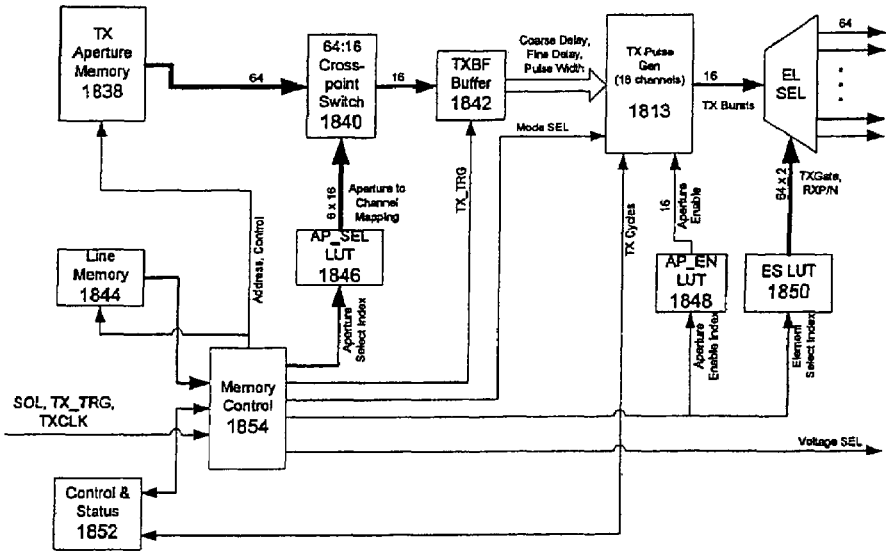
FIG. 18d is an illustration of an exemplary transmit controller (TX controller) in an embodiment according to the present invention.

FIG. 18d is an illustration of an exemplary transmit controller (TX controller) in an embodiment according to the present invention. The transmit controller 1814 is used to program the TX pulse generator 1813 with the correct delay profile (coarse delay and fine delay for each channel) and transmit waveform for each line. It re-programs the TX pulse generator 1813 before each line. The sequence of lines is used to produce a 2-D image. Each line requires a certain subset of the array elements to be used to form the transmit aperture. Each array element within the aperture must be connected to a channel in the TX pulse generator 1813, and the transmit channels must be configured to produce the desired transmit waveforms with delays according to the desired transmit delay profile.

The delay profile and transmit waveform for the entire aperture is stored in the TX Aperture Memory 1838. Multiple delay profiles can be stored in the TX Aperture Memory 1838. Multiple delay profiles are required for B-Mode imaging in which multiple focal zones are used, and PW Doppler and Color Flow Imaging modes in which the Doppler mode focal depth and transmit waveforms are different than those used for B-Mode. In this exemplary embodiment, the TX Aperture Memory 1838 contains delay profile and transmit pulse wave shape data for a 64 channel aperture. On each Channel Board there are 16 transmit channels, each of which can be connected to one of four different array elements through a transmit output stage. A 64:16 crosspoint switch 1840 is used to route the correct transmit waveform data sets to each of the 16 channels. The control of the other 48 channels is implemented on the other 3 channel boards. The TXBF buffer 1842 temporarily stores the TX pulse generator data before the start of line (SOL) trigger. The TX_TRG trigger moves the data from the TXBF Buffer 1842 into the TX Pulse generator 1813 in one TXCLK period.

The configuration for each transmit line is stored in the Line Memory 1844. Each line configuration in the Line Memory 1844 contains the following information: Aperture Select Index, Mode Select, Aperture Enable Index, and Element Select Index. The Aperture Select index is used to determine the Aperture to Channel mapping. The Mode Select is used to access multiple delay profiles. The Aperture Enable index controls the aperture size. The Element Select index controls which element is active in the case that there are more array elements than transmit channels or receive channels. The indexing of the Aperture Select, Aperture Enable and Element Select look-up tables (AP_SEL LUT 1846, AP_EN LUT 1848, ES LUT 1850) is a method to reduce the number of possible configurations and therefore number of bits required to store in the line memory 1844. The look-up tables are all re-programmable.

The Control and Status memory 1852 contains common parameters such as the number of transmit cycles (TX Cycles), the number of lines in the frame, and also configures the state machine in the Memory Control block 1854. Memory Control 1854 is a state machine that decodes the Aperture Select, Aperture Enable and Element Select line information.

Referring to FIG. 20, it can be seen that the transmit waveform is actually two signals, referred to as the "A" and "B" signals, one of which is applied to the gate of pulser drive MOSFET QTDN 62006 and the other applied to the gate of pulser drive MOSFET QTDP 2008. The "B" signal can be identical to the "A" signal except that it is delayed by ½ the period of the transmit clock. The delay applied to each transmit waveform is divided into two components, the "coarse delay" and the "fine delay". The coarse delay can be in units of ½ of the transmit frequency period, and the fine delay can be in units of 1/16 the transmit frequency period, though other units of fine delay are contemplated within the scope of this invention. Other aspects of the transmit waveform which can be adjusted are the transmit center frequency, pulse width, number of cycles and the "dead time". The "dead time" is the time interval following the first half cycle of the output pulse in which neither of the two output stage MOSFETs, QTDN 2006 and QTDP 2008, are turned on. Alteration of the transmit center frequency, pulse width and dead time may be used to alter the frequency content of the final transmit signal to the transducer element.

Figure 22:
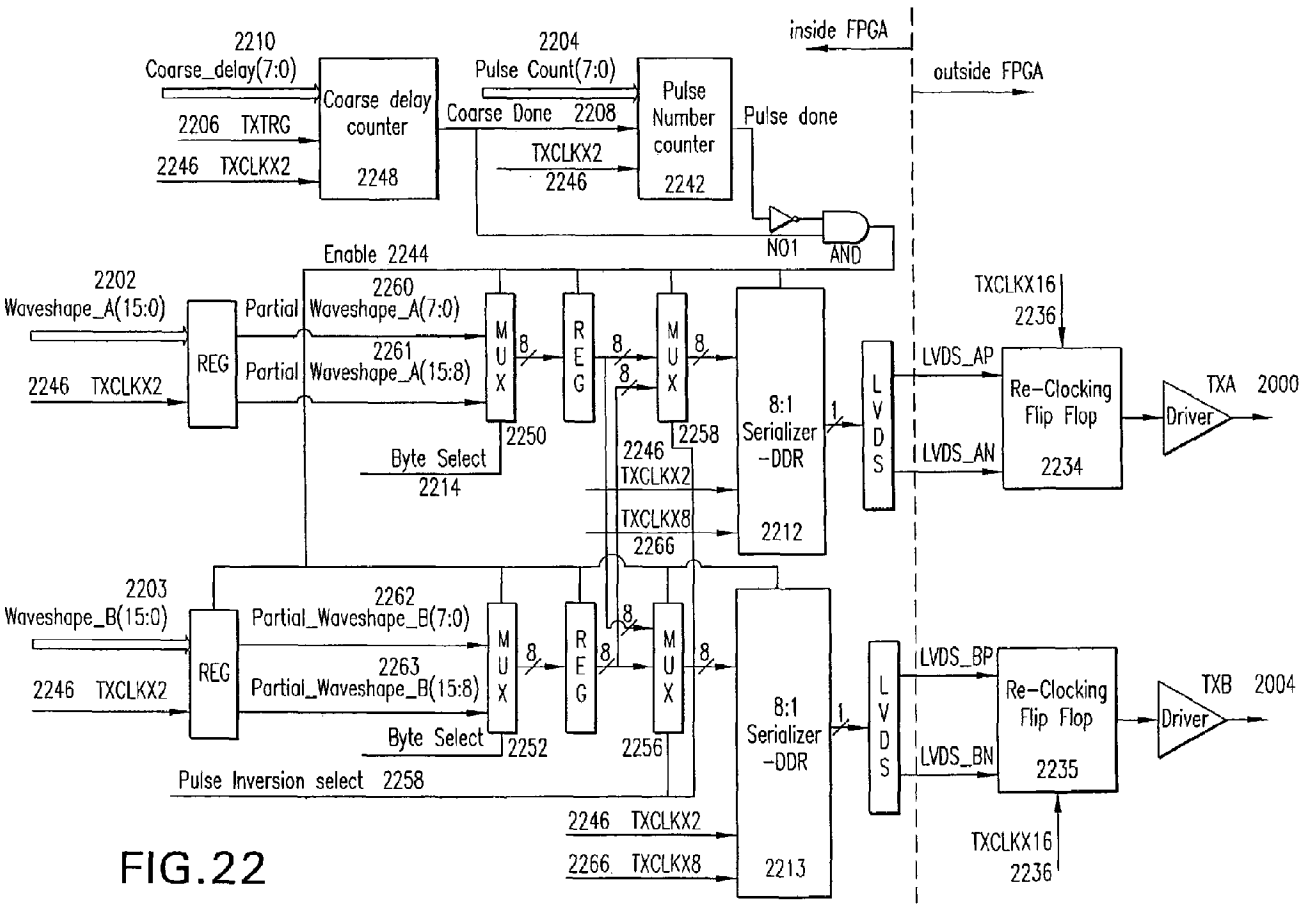
FIG. 22 is a block diagram for an exemplary transmit beamformer control.
Figure 22A:
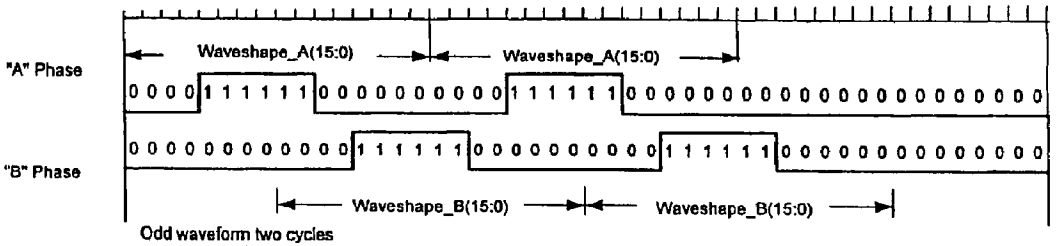
FIGS. 22A-22C illustrate how exemplary waveshape data can be used to change the fine delay, pulse width and dead time for "A" and "B" signals.
Figure 22B:
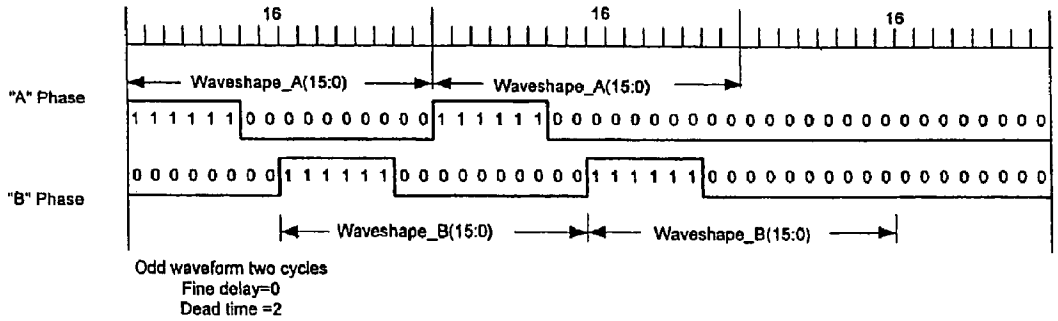
Figure 22C:
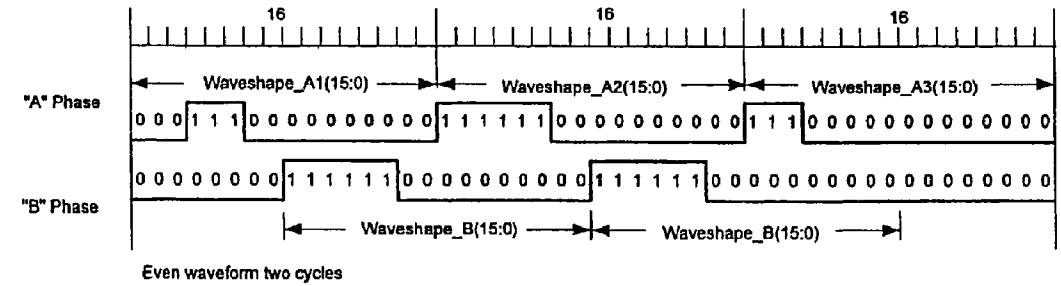

Referring now to FIGS. 22-22C, in an embodiment according to the present invention, one transmit pulse generation circuit 2200 is used for each transmit beamformer channel. A 16 bit A waveshape word 2202 is used to encode the fine delay, pulse width and dead time for the A signal. A 16 bit B waveshape word 2203 is used to encode the fine delay, pulse width and dead time for the B signal. The waveshape words 2202, 2203 can be stored in memory within, for example, a FPGA. The frequency of the transmit output signal is determined by the frequency of the transmit clock. The control inputs come from the transmit controller 1814, which can be implemented within the FPGA. These can be the pulse count 2204, the TXTRG 2206, and various clocks, as described below, and shown in FIGS. 22-22C.

Transmit pulse generation begins when a TXTRG pulse 2206 is received from the channel control board 1814. The TXTRG signal 2206 is sent to the transmit beamformer channels, and is the signal which the transmit beamformer delays are referenced to. The TXTRG pulse 2206 begins the counting of ½ intervals of the transmit frequency clock cycle denoted by TXCLK×2 2246. The current hardware implementation uses a clock of 2 times the transmit clock. The coarse delay 2210 is implemented by a Coarse Delay counter 2248 which is clocked by a clock, TXCLK×2 2246. The signal TXTRG 2206 causes the count to begin.

A COARSE DONE signal 2208 is generated when the number of clock cycles of TXCLK×2 2246 has reached the coarse delay input variable value 2210. The COARSE DONE signal 2208 enables the byte select circuit composed of multiplexers 2250 and 2252, Pulse Inversion select Circuit composed of multiplexers 2254 and 2256, and the 8:1 parallel-to-serial circuits 2212 and 2213. The 16 bit waveshape words 2202 and 2203 are transferred into 16 bit registers 2216 and 2217. The output of the A waveshape register 2216 is composed of the Partial Waveshapes: Partial_Waveshape_A(7:0) 2260 and Partial_Waveshape_A(15:8) 2261. Partial_Waveshape_A(7:0) 2260 is transferred to the either 8:1 parallel-to-serial circuit 2212 or 8:1 parallel-to-serial circuit 2213 through the Pulse Inversion Circuit composed of multiplexers 2254 and 2256. Following the transfer of Partial_Waveshape_A(7:0) 2260, Partial_Waveshape_A(15:8) 2261 is transferred to the either 8:1 parallel-to-serial circuit 2212 or 8:1 parallel-to-serial circuit 2213 through the Pulse Inversion Circuit composed of multiplexers 2254 and 2256. The Byte Select signal 2214 controls which of Partial_Waveshape A(7:0) 2260 or Partial_Waveshape_A(15:8) 2261 is multiplexed through to the Pulse Inversion Circuit. In this way, the full 16 bits of Waveshape_A 2202 is transferred to the 8:1 parallel-to-serial circuits for serialization into a one bit data stream.

As can be seen from FIG. 22, the transfer of the Waveshape_B 2203 is done in a similar manner.

The 8:1 parallel-to-serial circuit 2212 and 2213 have double data rate (DDR) outputs. COARSE DONE 2208 begins the count of the number of output pulses. When the pulse number counter finishes counting the number of pulses, the Enable signal 224 goes low causing the registers 2216 and 2217 to stop outputting the Partial Waveshapes. The 16-bit waveshape of the "A" phase 2202 is converted to 1 serial bit in two TXCLK×2 2246 cycles. The 16-bit waveshape of the "B" phase 2203 is also converted to 1 serial bit in two TXCLK×2 2246 cycles. Pulse inversion may be achieved by swapping the "A" and "B" phases before the signals are sent to the parallel-to-serial circuits. The signal swap occurs if the Pulse Inversion signal 2258 is enabled on the Pulse Inversion MUX circuit 2254 and 2256.

The 8:1 parallel-to-serial circuit with double data rate (DDR) output is clocked with TXCLK×8 2266 which is at a frequency of 8 times the transmit clock. With DDR output, the waveshape is shifted out at a rate of 16 times the transmit clock frequency. The signals from 8:1 parallel-to-serial circuit 2212 or 8:1 parallel-to-serial circuit 2213 are transferred out of the FPGA using the LVDS standard before it is resynchronized by clock TXCLK×16 2236.

The "A" phase signal is re-synchronized by a low jitter positive emitter coupled logic (PECL) flip-flop 2234 and a low jitter clock, TXCLK×16 2236, at 16 times the transmit frequency. This can eliminate jitter added by the circuit inside the FPGA. The "B" phase signal is also re-synchronized by flip-flop 2235.

Both the "A" and "B" signals go to respective driver circuits 2238, 2240 to increase their current drive capability. The output of the drivers become signals TXB 2004 and TXA 2002 and connect to the transmit multiplexers in the front end circuit 2000.

Re-sending of the waveshape data 2202 and 2203 continues until the pulse number counter 2242 has reached the number specified by the pulse count input variable 2204 and the enable signal 2244 changes state.

The 16 bit word which constitutes Waveshape_A 2202 may change from one transmit cycle to the next. The same applies to Waveshape_B 2203. This allows for the generation of transmit waveforms with arbitrarily specified pulse widths from one cycle to the next. Waveshape_A 2202 and Waveshape_B 2203 are specified independently. For example, either odd or even transmit waveforms may be generated.

FIGS. 22A-22C illustrate how the waveshape data can be used to change the fine delay, pulse width and dead time for the "A" and "B" signals. In this example, the "B" output is identical to the "A" output except it is delayed by ½ of the transmit frequency period. FIG. 22C illustrates that arbitrary waveforms can be generated in the "A" phase and the "B" phase. Ny Waveshape_A may be different from the one preceding it, and any Waveshape_B may be different from one preceding it. In the example in FIG. 22C, the 16 bit waveforms used for Waveshape_A1(15:0), Waveshape A2(15:0) and Waveshape_A3(15:0) are different from one another. In this example, the Waveshape_B(15:0) is repeated twice, but it would be possible to specify that a Waveshape_B be different from the preceding Waveshape_B. The A and B waveforms are independent and can be used to implement transmit waveforms used for coded excitation methods, for example in applications involving contrast agent imaging and non-linear imaging.

The TXPower signal (shown as "TX High Voltage" in FIG. 18b) can control the amplitude of the output of the transmit pulser. As shown in this implementation, TXPower is common to all transmit channels. Optionally, the amplitude of the output pulse of each transmit channel can be controlled individually.

Figure 19:
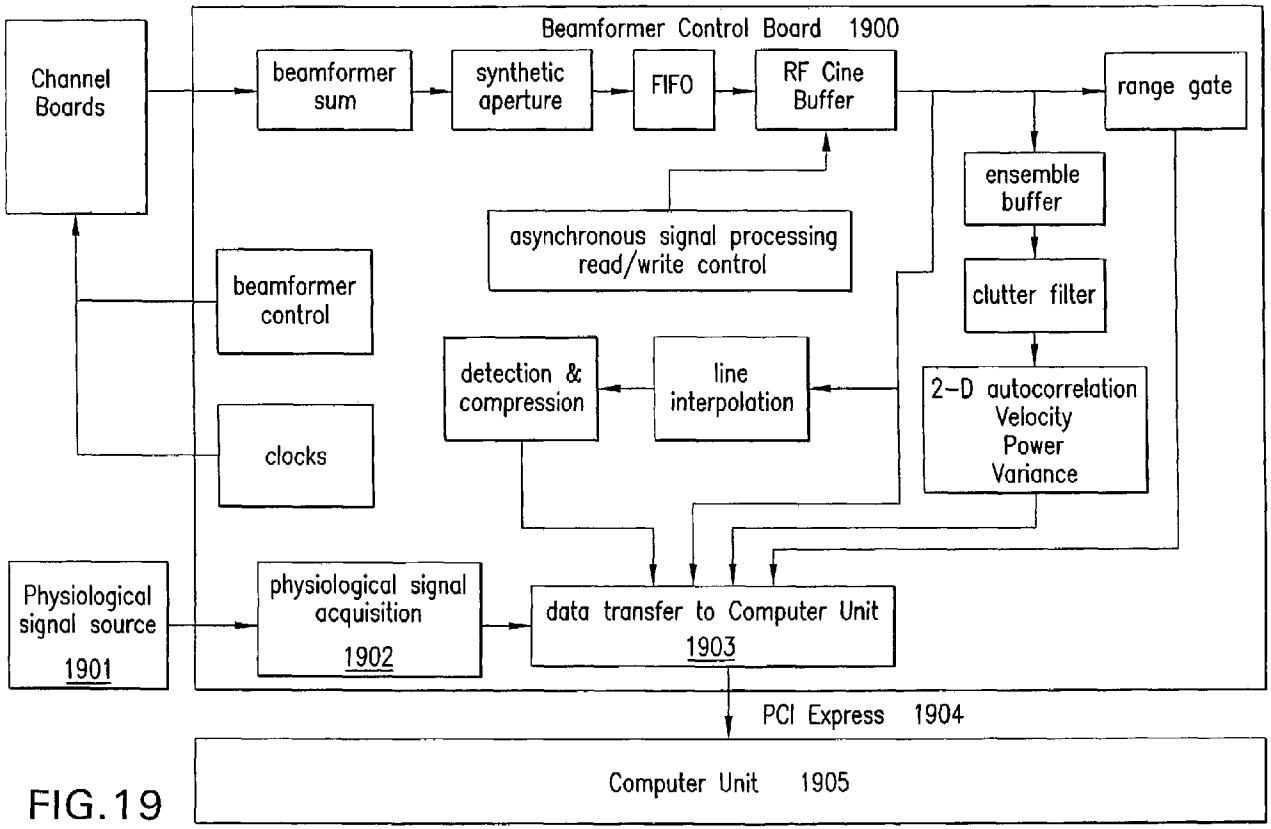
FIG. 19 is a system signal processing block diagram illustrating an exemplary beamformer control board.

FIG. 19 is a system signal processing block diagram illustrating an exemplary beamformer control board 1900. The beamformer control board 1900 is an exemplary embodiment of the beamformer control and signal processing block 1716. The design and operation of the beamformer control board 1900 is generally known to one of ordinary skill in the art. Embodiments of the exemplarily system can have the capability to acquire, process and display physiological signal sources 1901 of one or more of, for example, ECG, respiration, body temperature of the subject, or blood pressure. The physiological signal acquisition block 1902 can contain signal acquisition modules that can acquire those types of physiological signals.

The data transfer to computer unit 1903 transfers data from the beamformer control board 1900 to the computer unit 1905. Embodiments can use a PCI express bus 1904, as is known in the art, for this transfer, or similar buses.

FIG. 20 is an exemplary schematic 2000 of the front end circuit transformer 1702, transmit output stage 1703 and the receive MUX 1704 and the transmit MUX 1708. Other exemplary front end circuits can also be used with the described system. For example, front end circuits as described in U.S. Pat. No. 6,083,164, entitled "Ultrasound Front-End Circuit Combining the Transmitter and Automatic Transmit/Receive Switch," which is fully incorporated herein by reference and made a part hereof, can be used. The exemplary circuit 2000 depicted in FIG. 20 provides the multiplexing function of connecting an element to the receive channel if that element is part of the active aperture. The front end circuit also provides isolation of the receive channel from the transmit channel, as described herein. The transmit output stage receives a transmit waveform from the transmit pulse generator 1813 and in turn combines the transmit pulse information with transmit high voltage to create a high voltage waveform at an element which is part of the active transmit aperture.

In the exemplary schematic shown in FIG. 20, transmit pulsing is effected by D1 2010, D2 2012, QTDP 2008, QTDN 2006, QTXMUXP 2014, QTXMUXN 2016 and T1 2018. During transmit, the transmit output stage which is included in the active transmit aperture is connected by turning on QTXMUXP 2014 and QTXMUXN 2016 to allow the gate drive signals, TXA 2002 and TXB 2004, to reach QTDN 2006 and QTDP 2008. During transmit pulsing, either QTDN 2006 or QTDP 2008 are turned on separately, with timing as required to produce the intended transmit waveform. The pulser output appears on the left end of the transformer secondary, LTXS 2038, while the right end is clamped near 0 V by D1 2010 and D2 2012, which can be, for example, ordinary fast silicon switching diodes. During active pulsing, the receive multiplexing switch SW1 2020 can also be turned off to provide additional isolation. The amplitude of the output of the transmit pulser is determined by the transmit supply voltage applied to the center tap of the primary of T1 2018 through R1 2022. Two voltage supplies are available, V1 2024 and V2 2026, where V1 2024 is larger than V2 2026. They are connected to a common node at the R1 2022 as shown through FET switches QLSH 2028, QLSL 2030 and diode D3 2032. One or the other of the supply voltages is selected by turning on either QLSH 2028 or QLSL 2030 using control signals V1 NE 2034 and V2 NE 2036. Diode D3 2032 helps prevent current from flowing from V1 2024 to V2 2026 when V1 2024 is connected to R1 2022. This configuration allows for rapid switching of the transmit supply voltage between two levels, since it avoids the requirement to charge or discharge the supply voltage as held on voltage storage capacitors C4 and C5.

Receive switching is effected by QTDP 2008, QTDN 2006, QLSH 2028, QLSL 2030, and SW1 2020. SW1 2020 is a receive multiplexing switch which can be a single pole single throw (SPST) or a single pole double throw (SPDT) switch of a type such as a GaAs PHEMT (gallium arsenide pseudomorphic high electron mobility transistor). Alternatively, the receive multiplexing switch may be implemented with other types of field effect transistors or bipolar transistors. If SW1 2020 is a SPDT switch it is configured as shown in FIG. 20, where one terminal is connected to a terminating resistor and the other is connected to the receive channel input. If SW1 2020 is a SPST switch, the terminal connected to the terminating resistor and the terminating resistor is deleted.

During receive intervals, the receive multiplexing switch is configured such that there is a connection between the array element and the receive channel. The pulser drive MOSFETs, QTDN 2006 and QTDP 2008, are both turned on during receive, while QLSH 2028, QLSL 2030, QTXMUXN 2016 and QTXMUXP 2014 are held off. This causes LTXS 2038 to present mainly its leakage inductance as an impedance in series with the receive signal. For received signals too small to forward bias D1 2010 or D2 2012, these diodes present high shunt impedance, dominated by their junction capacitance. L1 2040 and the leakage inductance LTXS 2038 are used to level the receive mode input impedance, compensating for the junction capacitance of D1 2010, D2 2012 and the capacitance of the ganged switches forming the receive multiplexer.

Figure 21:
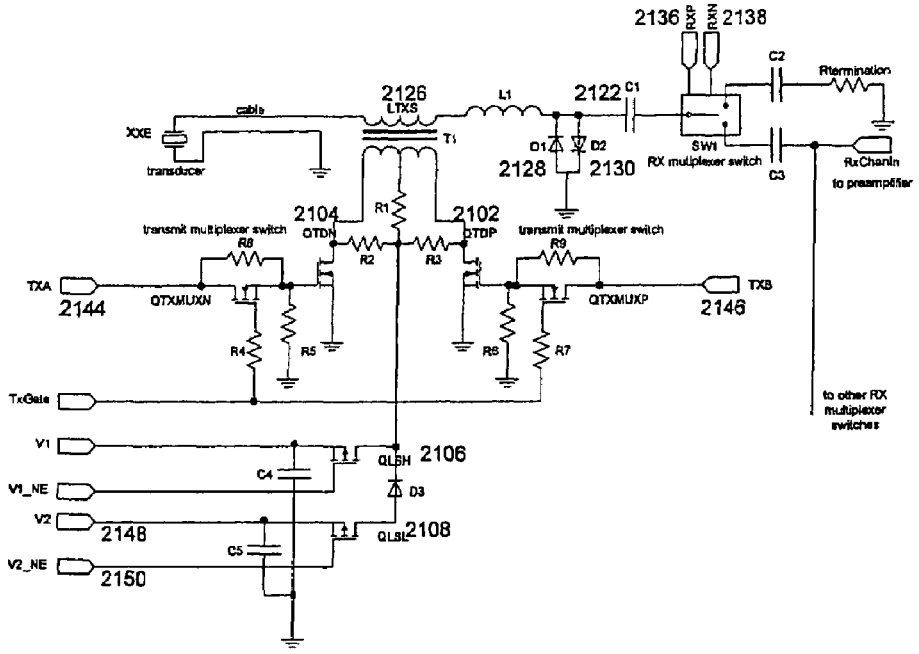
FIG. 21 is a schematic diagram of an alternative embodiment of a TX/RX Switch and Pulser and related circuitry.

In an alternative implementation of the front end circuit, and as shown in FIG. 21, signal RXCLMP is eliminated and its' function performed by TXA and TXB. The transmit function on this circuit is identical to the circuit of FIG. 20 with QTXMUXN and QTXMUXP gating signals TxDriveN and TXDriveP. In receive mode QTXMUXN and QTXMUXP are off thus blocking signals TXA and TXB. Resistors R8 and R9 shunt QTXMUXN and QTXMUXP so that when TXA and TXB are driven high for the duration of receive mode the voltage on the gates of QTDN and QTDP increases slowly resulting in gentle activation of these MOSFET switches. The gentle activation of QTDN and QTDP for receive mode is controlled by signal RXCLMP in the circuit of FIG. 20. In FIG. 21, resistors R5 and R6 pull the voltage on the gates of QTDN and QTDP to ground when transmit multiplexing switches are turned off after a transmit operation.

The pulser employs a center-tapped transformer and NMOS FETs, together with a switch-selectable level supply, to generate nominally square pulses. In order to control the delivered spectrum when connected to the transducer element thru a controlled impedance coax cable, it employs series and shunt resistances. These serve to reduce the time-variation of source impedance during operation of the pulser and provide back termination of the transducer during the interval immediately following transmit pulses. Not shown in the schematic is the drive circuit for the final stage MOSFETs. This circuit, (which is on the far side of a multiplexer as describe below), may be either a discrete switching MOSFET pulse amplifier or a collection of CMOS buffers sufficient to provide the required drive.

The transformer needed for the pulser is built as windings printed on the PCB augmented by small ferrite slabs fastened onto both sides of the PCB, around the windings. This technique is amenable to automated assembly provided the ferrite slabs can be packaged appropriately.

EXAMPLES

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Example 1

Figure 23:
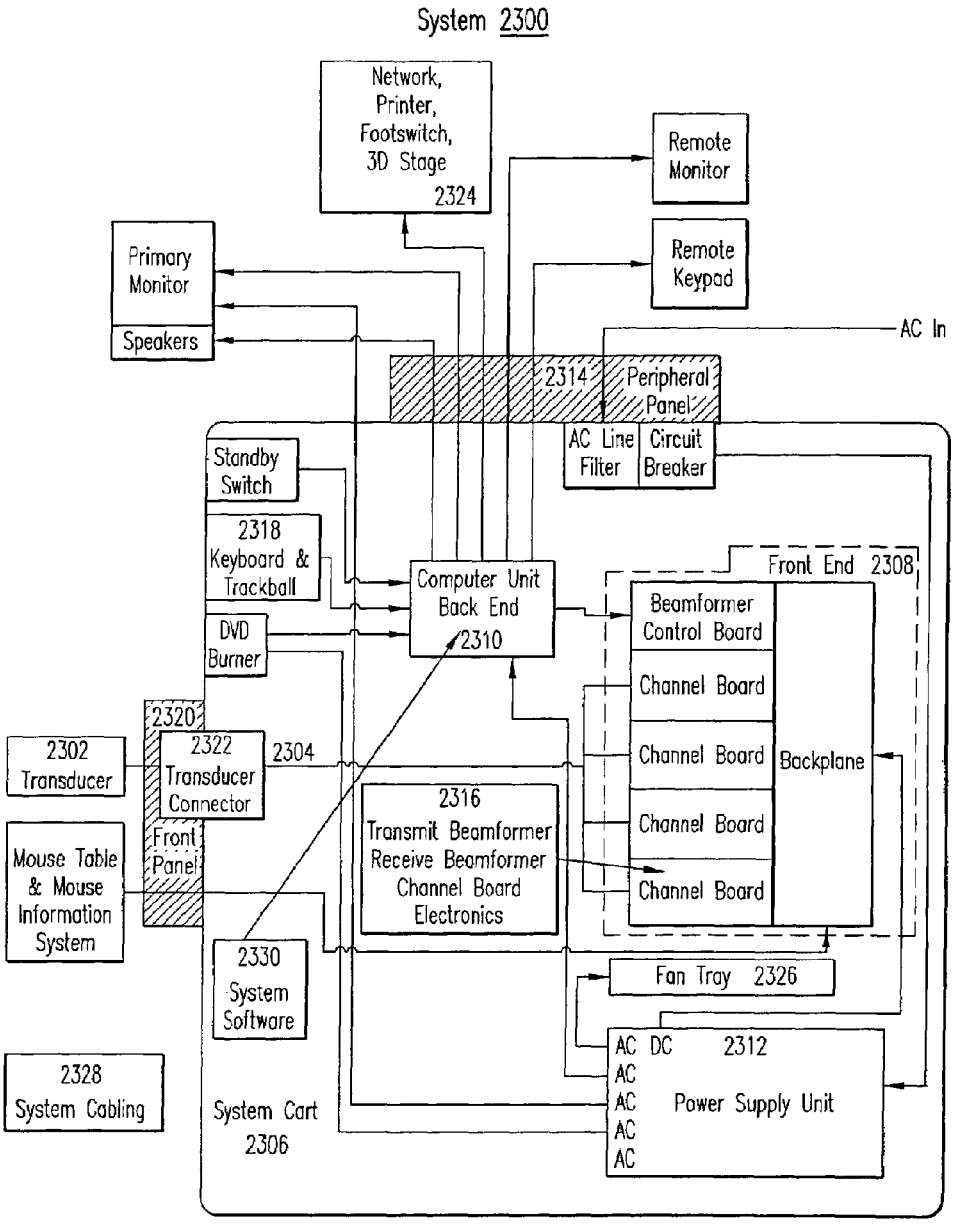
FIG. 23 is a block diagram showing an exemplary system according to an embodiment of the present invention.

FIG. 23 is a block diagram showing exemplary system according to an embodiment of the present invention. The exemplary system 2300 is interfaced with a linear array 2302 having, for example, up to 256 elements. A bundle of micro coax cables 2304 provides transmission of the signals between the array 2302 and the processing unit 2306. The exemplary system further comprises a processing unit.

The processing unit 2306 is partitioned into two major subsystems. The first is the front end 2308, which includes the beamformer, the front end electronics, the beamformer controller and the signal processing module. The second is the computer unit 2310, or back end. The front end subsystem 2308, is concerned with transmit signal generation, receive signal acquisition, and signal processing. The back end 2310, which can be an off-the-shelf PC motherboard, is concerned with system control, signal and image processing, image display, data management, and the user interface. Data can be transferred between the front and back end sub-systems by, for example, a PCI express bus, as is known in the art to one of ordinary skill.

The module which processes the receive signals is the receive beamformer, as previously described herein. The subsystem which generates the transmit signals is the transmit beamformer, also as previously described herein. Each channel of the transmit and receive beamformers is connected to a separate element in the array 2302. By altering the delay and amplitude of the individual transmit or receive signals at each element, the beamformer is able to adjust the focal depth, aperture size and aperture window as a function of depth. The exemplary system of FIG. 23 may support one or more various modes of ultrasound operation as are known in the art to one of ordinary skill. These modes are listed in Table 2, below:

TABLE 2

| Modes Supported |
|---|
| B-Mode |
| M-Mode |
| PW Doppler |
| Color Flow (Velocity) Doppler |
| Power Doppler |
| Tissue Doppler |
| 2nd Harmonic |
| Triplex |
| EKV |
| ECG triggered imaging |
| 3-D imaging |
| 3-D real-time (4 Hz) |
| RF Mode |
| Anatomical M-Mode |

System Specifications

Exemplary specifications of the system shown in FIG. 23 may include, for example, those specifications listed in Tables 3, below:

TABLE 3

| System Specifications | |
|---|---|
| Number of transducer elements supported | Up to 256 |
| Transmit channels (active aperture) | 64 |
| Receive channels | 64 |
| Transducers supported | Linear, curved linear |
| Center frequency range | 15 to 55 MHz |
| Data acquisition method | Quadrature sampling |
| BF sampling frequency range | 15 to 62 MHz |
| Receive BF fine delay implementation | Interpolation filter |
| Receive delay resolution | T/16 |
| ADC number of bits | 10 |
| Transmit delay resolution | T/16 |
| TGC | yes |
| Synthetic Aperture | yes |
| Maximum transmit voltage | 80 Vpp |
| Transmit power control | yes |
| Multiple Transmit focal zones | yes |
| Transmit cycle adjustment | 1-32 |
| B-mode frame rate max | 200 |
| CFI frame rate max | 160 |
| PW Doppler maximum PRF | 150 KHz |
| CFI maximum PRF | 75 KHz |
| Doppler beam steering | yes |
| Cine buffer size | 300 frames |
| Physiological signal acquisition | yes |
| Transducer connectors | One or more |

System Cart

The system or portions thereof may be housed in a portable configuration such as, for example, a cart, including beamformer electronics 2316, a computer unit 2310, and a power supply unit 2312. The user interface includes an integrated keyboard 2318 with custom controls, trackball, monitor, speakers, and DVD drive. The front panel 2320 of the cart has connectors 2322 for connecting an array-based transducer 2302 and mouse physiological information such as ECG, blood pressure, and temperature. The rear peripheral panel 2314 of the cart allows the connection of various peripheral devices such as remote monitor, footswitch, and network 2324. The cart has a system of cooling fans 2326, air guides, and air vents to control the heat of the various electronics.

In one embodiment the computer unit 2310 may be an off-the-shelf Intel architecture processor running an operating system such as, for example, Microsoft Windows XP. The computer unit 2310 may be comprised of, for example, an Intel 3 GHz CPU (Xeon Dual Processor or P4 with Hyper-threading); 2 GB DDR memory; PCI Express x4 with cable connector; 100 Mbps Ethernet; USB 2.0; Graphics controller capable of 1024×768×32 bpp@100 Hz; Audio output (stereo); 2×120 GB 7200 RPM Hard disk drives (one for O/S+software; one for user data) and 300 W ATX power supply with power-factor correction.

In one embodiment the power supply unit 2312 may be comprised of the following: a universal AC line input (100, 120, 220-240 VAC, 50 or 60 Hz), where the AC input is provided by a detachable cable that connects to a system AC input terminal block and has AC distribution using IEC terminal blocks. In one embodiment, the inrush current is limited to 6 A or less during the first 100 ms of power up. The system cart of FIG. 23, and other embodiments of the invention, is further comprised of system cabling 2328. System cabling 2328 includes a main AC line cord; AC cordage for line filter, circuit breaker, power supply unit; AC cordage inside the power supply unit 2312; a computer unit 2310 power supply cord; monitor power supply cord; DVD drive power supply cord, a fan tray 2326 power supply cord and other power cordages as used in the embodiments according to the invention. System cabling 2328 further comprises instrument electronics cables, which include instrument electronics sub-rack power cable; PCI Express cable; transducer connector cable; mouse information system (MIS) cable; 3D stage cable; standby switch cable; etc. System cabling 2328 further comprises computer cables, which may include video extension cable(s) (VGA, DVI, SVideo, etc.); keyboard/mouse extension cable(s); keyboard splitter; mouse splitter; remote mouse cable; remote keypad cable; remote video cable; USB extension cable(s); Ethernet extension cable; printer extension cable; speaker extension cable, etc.

Cooling

Filtered ambient air is provided through the use of fans 2326 to the system cart electronics which include, for example, the beamformer electronics (i.e., the beamformer card cage 2316, power supply unit 2312, and computer unit 2310. The cooling system supports, for example, in one embodiment an ambient operating temperature range of +10 to +35° C., and the exhaust air temperature is kept below 20° C. above the ambient air temperature, though other ambient operating ranges are contemplated within the scope of this invention.

Electro-Magnetic Interference (EMI) Shielding

In one embodiment, the exemplary system is provided with a contiguous EMI shield in order to prevent external electromagnetic energy from interfering with the system operation, and to prevent electromagnetic energy generated by the system from emanating from the system.

The system shielding extends to the transducer cable 2304 and the array 2302, and the transducer connector 2322. The computer 2310 and power supply units 2312 may be housed in separate shielded enclosures within the system. All shields are maintained at approximately ground potential, with very low impedance between them. There is a substantially direct connection between the chassis ground of the system and earth ground. Also, in one embodiment the AC supply may be isolated from the system power supply by an isolation transformer as part of the power supply unit 2312.

Electronics Overview

Figure 24:
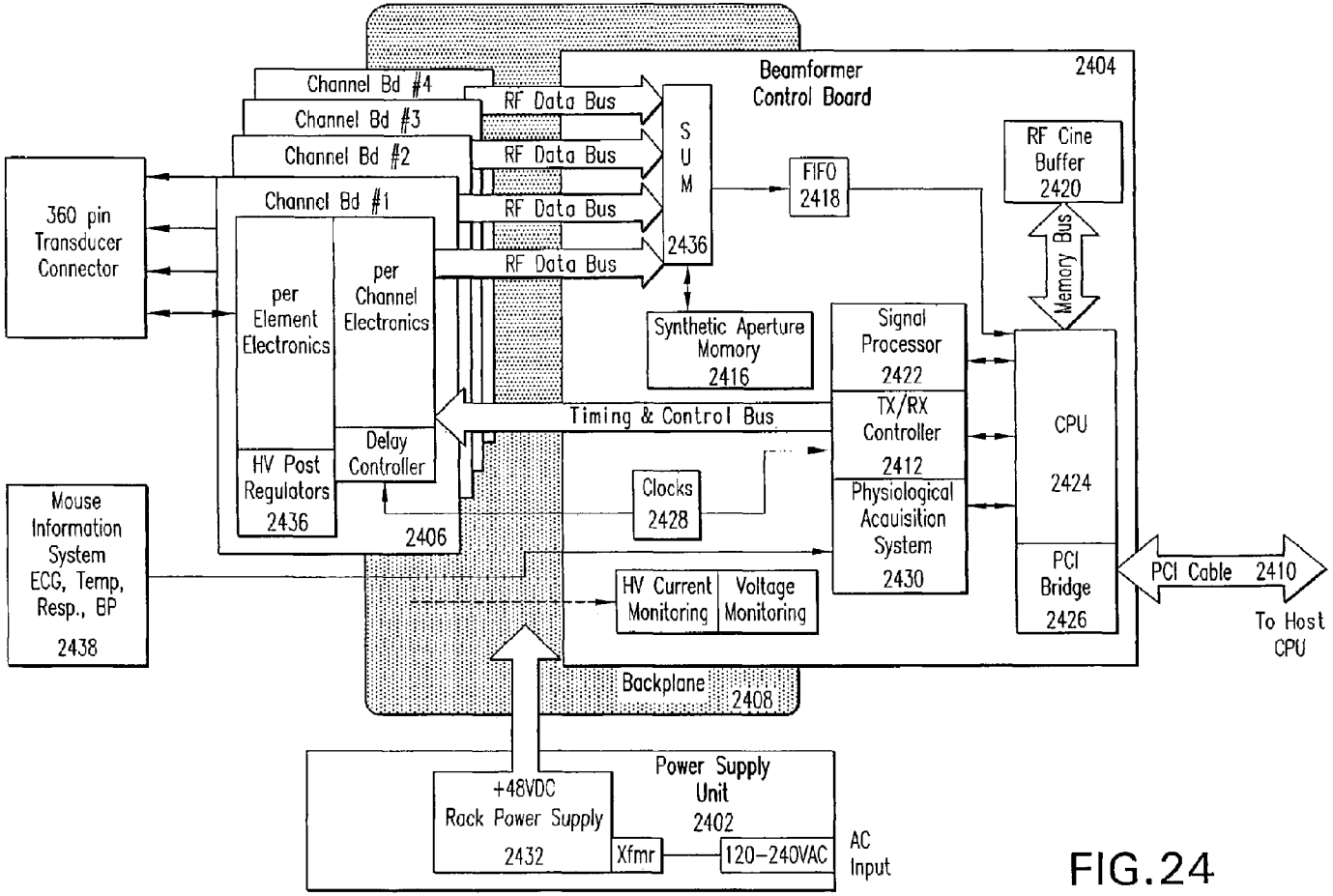
FIG. 24 illustrates a systems electronics overview of an exemplary high frequency ultrasonic imaging system.

An overview of an embodiment of the electronics for an exemplary system according to the invention is shown in FIG. 24. In this view, the exemplary system comprises of a power supply unit 2402, instrument electronics subrack, and computer unit. The power supply unit 2402 distributes both AC and DC power throughout the cart. A DC voltage of, for example, 48V is supplied to the instrument electronics subrack though other voltages are contemplated within the scope of this invention. The instrument electronics subrack houses a beamformer control board 2404, four identical channel boards 2406, and a backplane 2408. The boards 2406 mate with the backplane 2408 via, for example, blind mate connectors. The instrument electronics communicate with the computer unit via, for example, a PCI express connection 2410.

Channel Board

Exemplary channel boards are shown, and have been previously described, in reference to FIGS. 18a-18d. The channel boards 2406 generate the transmit signals with the proper timing for transmit beamforming, and acquiring, digitizing and beamforming the receive signals. In this exemplary embodiment of FIG. 24, there are four channels boards 2406, each containing 16 transmit channels and 16 receive channels Each channel board 2406 also contains 64 front end circuits, including transmit output stages, power supply circuitry, an FPGA for the transmit beamformer, an FPGA to provide the partial sum of the receive beamformer, the beamformer bus and connections to the backplane.

As can be seen in FIG. 18a, four front end circuits are multiplexed to each transmit and receive channel. There is one front end circuit for each element in the array, and each front end circuit comprises a transmit output stage, transmit and receive multiplexer switches, a diode limiter, and components for receive filtering, as previously described in reference to FIGS. 18a-18d.

The transmit channels and transmit output stages generate bipolar pulses at a specified frequency ranging from about 15 to about 55 MHz, with a specified cycle count and amplitude. The transmit waveforms generated by each channel have a specific delay relative to the other channels with a resolution equal to approximately 1/16 of the period of the transmit frequency. The delay profile across the active transmit aperture is controlled by the transmit beamformer controller. A low jitter master clock is used to generate the transmit burst signals. The transmit output stage includes a means of adjusting the peak to peak voltage on a per channel basis, in order to create an apodized transmit aperture.

The receive channels provide variable gain adjustment, filtering and digitization of the receive signals, and receive beamforming. The gain is implemented with a variable gain amplifier which also acts as the preamplifier. Gain is varied throughout the acquisition of the ultrasound line according to a predetermined gain profile known as the TGC curve. Anti-aliasing filters precede the ADC (analog-to-digital converter) to prevent aliasing and to limit the noise bandwidth.

As shown in FIG. 18a, dual ADCs 1807, 1808 are used for each channel, since the signal is acquired as a quadrature signal. The ADC clocks are phased 90° relative to one another. The sampling frequency is set according to the center frequency of the array being used. The 10 bit output of the ADCs is sent to a dual port RAM. The receive beamformer reads the quadrature samples and carries out interpolation filtering according to the dynamic receive focusing scheme which is controlled by the receive beamformer controller. After interpolation filtering, the outputs from each receive channel are summed and then sent to the CPU via the high speed data transfer bus.

The receive beamformer is setup via the RX Control Bus. The transmit beamformer is setup via the TX Control Bus. The control parameters are updated before the start of each ultrasound line. The control parameters are TX aperture, TX delay profile (coarse and fine delay), RX aperture, RX delay profile (initial, coarse and fine delay), RX phase, and RX apodization. When all the control parameters are set and the system is ready—a start-of-line (SOL) signal is sent to begin a transmit/receive cycle.

Transmit Output Stage

Multiplexing of the transmit channels occurs prior to the transmit output stage. Since the transmit beamformer can work with arrays with up to 256 elements, there are 256 transmit output stages, one per element. As shown and described in reference to FIGS. 20 and 21, each output stage consists of two MOSFETs driving a center tapped transformer, with the supply voltage at the center tap controlling the pulse amplitude. The output waveform is approximately a square pulse with a variable number of cycles. One end of the secondary of the transformer leads to the array element, the other to the receive protection circuit. Reactive impedance elements provide impedance matching and filtering. A FET switch in series with the gate of each MOSFET provides the multiplexing. The transformer and inductors are implemented, for example, as traces on the printed circuit board. There is a ferrite core for the transformer which is inserted into an opening in the board.

Transmit Channel

Each transmit channel is multiplexed to four output stages as can be seen in FIG. 18. There are two transmit signals per channel, one to drive each phase of the push-pull output stage. As can be seen in FIGS. 20 and 21, the analog section of the transmit channels consist of a push-pull type driver circuit capable of driving the gate capacitance of the output stage MOSFETs with the appropriate rise and fall times. These are multiplexed to the output stages by analog switches.

Transmit Beamformer

As can be seen in FIG. 22, the transmit beamformer uses DDR memory to produce transmit waveforms clocked at a maximum of approximately 800 MHz. Each channel uses a separate DDR memory output. The output clock rate is about 16× the center frequency (fc), thereby providing capability for the appropriate delay resolution. Jitter is reduced by re-clocking the DDR output with PECL. As can be seen in reference to FIG. 22A, with a clock rate of about 16×fc, transmit waveshaping can be effected, by adjusting the width of the positive or negative half cycles. This capability can introduce "dead time" between the positive and negative half cycles to improve the shape of the output pulse.

Front End Circuit

For a transducer array comprised of 256 elements, there are 256 front end circuit sections, one dedicated to each array element. As can be seen in reference to FIG. 17, each front end circuit comprises a front end transformer 1702, a transmit output stage 1703, transmit MUX 1708, a receive MUX 1704, a diode limiter, and components for receive filtering.

Receive Channel

Also as can be seen in reference to FIG. 17, each receive channel comprises the circuit elements which are involved with the acquisition of the receive signal. The receive multiplexer 1704 connects the 64 receive channels to the elements within the active aperture, which is a subset of up to 64 contiguous elements within the 256 element array.

Receive Beamformer

The receive beamformer, such as the one shown in FIG. 17, is a module which independently processes and sums the digital data acquired by each channel in the receive aperture. Its functions may include, for example: dynamic control of the receive aperture size, i.e., the number of channels used during the acquisition of each receive sample; dynamic control of receive apodization, i.e., the window applied to the receive aperture; dynamic receive focusing, i.e., up sampling of the receive signal and the adjustment of the delay applied to each receive channel during the acquisition of each, sample, through the use of interpolation filters and variation of aperture position within the array.

Channel Board Configuration

As shown in the exemplary system of FIG. 24, there are four channel boards 2406, each containing 16 transmit and 16 receive channels, all plugging into a backplane. Each channel board is assigned an address based on its position in the backplane to allow independent control of each board.

Beamformer Control Board

The beamformer control board 2404 of the exemplary system of FIG. 24 provides and uplink of data to the host CPU (back end) and centralized timing and control for the hardware electronics. The link to host CPU is via a PCI express bus 2410, which allows a data bit rate of approximately 250 MB/s in each direction per lane. An x8 lane width PCI Express link provides a peak full-duplex bandwidth of approximately 4 GB/s.

The TX/RX controller 2412 provides master timing using start of frame and start of line synchronization signals to the transmit beamformer and receive beamformer. It sets up the beamformer parameters in memory via a custom local bus. All the low jitter clock frequencies for beamforming are generated on the beamformer control board 2404.

The RF partial sum data from each channel board 2406 is summed 2414 together with synthetic aperture data 2416. Then the ray line data goes into a first-in-first-out (FIFO) memory 2418 where it sits temporarily before being copied to the RF Cine buffer 2420. The RF Cine buffer 2420 stores full frames of RF data and is randomly accessible. Data is read from the RF Cine buffer 2020 and copied to the host CPU via the PCI Express link 2410. Alternatively, the data can be processed by the signal processor module 2422 before being sent to the main computer unit. The data is then buffered, processed further and displayed by the application software and application user interface that runs on the main computer unit.

The data traffic control and reading/writing of control parameters is facilitated by the embedded CPU 2424. The embedded CPU 2424 itself is accessible by the host CPU via the PCI Express link 2410. Other functions provided by the beamformer control board 2404 are the physiological acquisition system and power supply monitoring. FIG. 19, previously referenced herein, is a block diagram of an embodiment of a beamformer control board 1900.

TX/RX Controller

Transmit Beamformer Control:

The transmit (TX) beamformer control updates the transmit beamformer parameters each transmit line. The parameters include number of coarse delay cycles at the transmit center frequency (fc), number of fine delay cycles (at 16×fc), transmit waveshape (at 16×fc), number of transmit cycles, transmit select, and transmit voltage. The transmit beamformer control also schedules the updating of parameters for duplex mode, triplex mode, or multiple focal zones.

Receive Beamformer Control:

The receive beamformer control controls the receive delay profile, aperture size and apodization for each channel. The delay control consists of coarse and fine delays, which are controlled by the dual port RAM read pointer and the interpolation filter coefficient selector bit, respectively.

Figure 26:
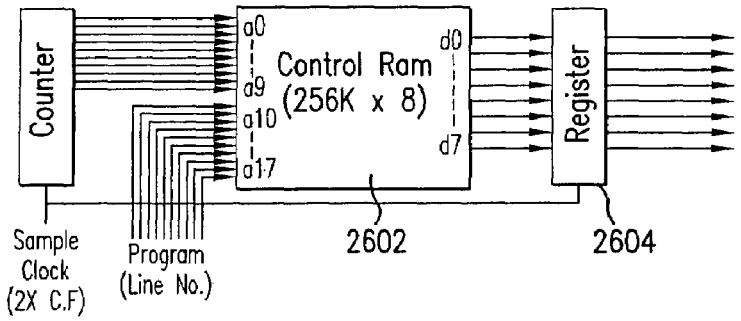
FIG. 26 illustrates an exemplary control RAM for storing receive control signals.

The aperture control signal controls the aperture size dynamically by specifying when the output of each channel becomes active. This is done by controlling the clear signal of the final output register of the interpolation filters. Dynamic receive apodization is controlled by five bits of apodization data with which the signal in each channel is multiplied. The receive control signals are read out from a control RAM at the input sample clock rate as shown in FIG. 26.

Figure 27:
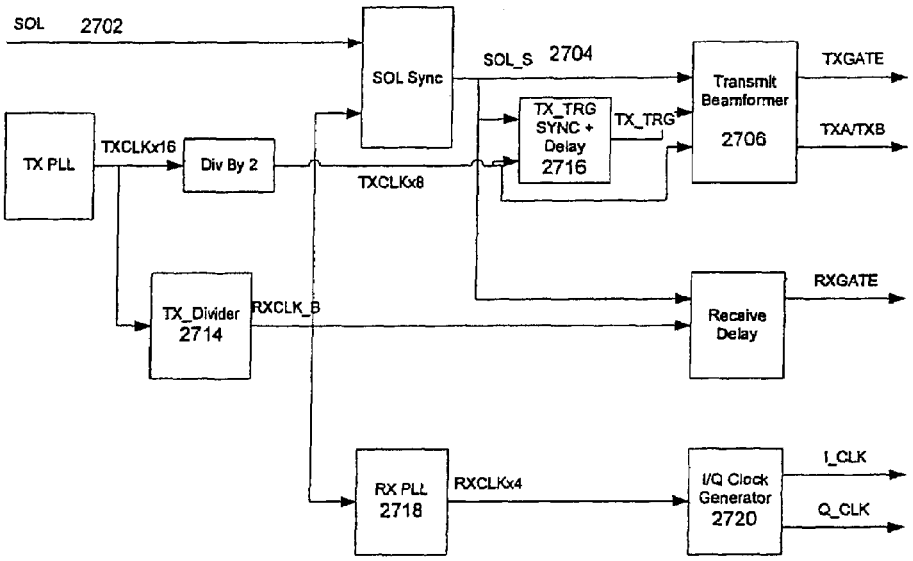
FIG. 27 is a block diagram of an exemplary transmit/receive synchronization scheme.

Transmit/Receive Synchronization:

A block diagram of transmit/receive synchronization is shown in FIG. 27. For B-Mode and M-Mode imaging different transmit and receive frequencies can be used. However, line-to-line timing differences (jitter) between the transmit cycle and receive cycle may be introduced because the clocks are asynchronous. A method to synchronize the transmit and receive clocks is to use a programmable divider (TX_Divider) 2714 to generate the receive clock (RXCLK_B) from the transmit clock (TXCLK×16) as shown in the embodiment of FIG. 27. The receive frequency is a fixed ratio of the transmit frequency. The ratio is transmit clock frequency times 16 divided by N, where N is an integer. For example, in order to generate a transmit clock frequency of 30 MHz and a receive clock (RXCLK_B) frequency of 26.7 MHz, the TX_Divider 2714 is set to divide by 18. Due to the nature of the divider, RXCLK_B is in good phase alignment with TXCLK×16, and the two clocks always have a minimum phase difference. RXCLK_B is used to synchronize the start of line trigger (SOL) 2702. The synchronized start of line trigger (SOL_S) 2704 generates TX_TRG. TX_TRG is synchronized to TXCLK×8 by TX_TRG SYNC 2716. A delay between SOL_S and TX_TRG can be added if necessary. TX_TRG signals the transmit beamformer to begin a transmit cycle. RXGATE is synchronized to RXCLK_B and signals the receive beamformer to begin data acquisition. A multiplier (RX PLL) 2718 provides the RXCLK×4 clock frequency that is needed by the I/Q Clock Generator 2720 to generate the I and Q clocks.

Figure 27A:
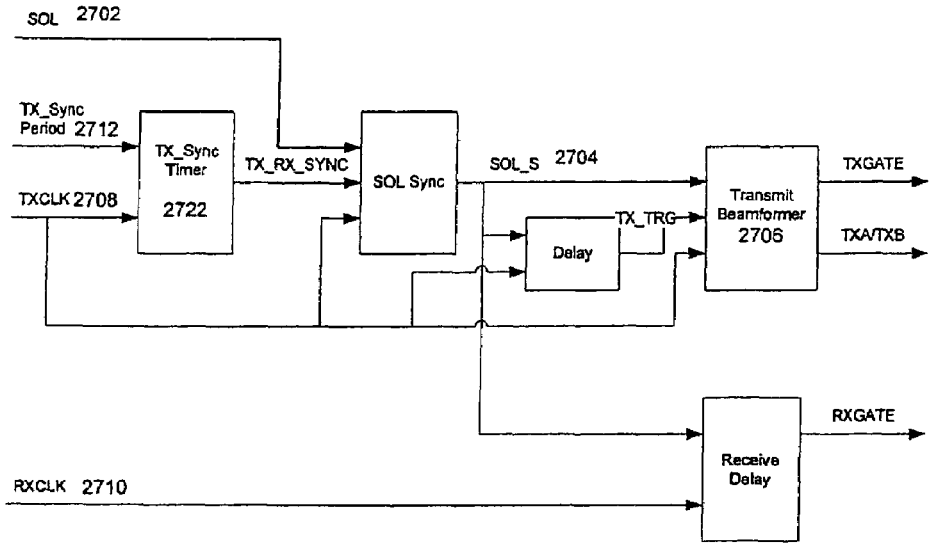
FIG. 27A is a block diagram of an alternate exemplary transmit/receive synchronization scheme.

FIG. 27A illustrates an alternative method of maintaining consistent synchronization between the transmit cycle and receive cycle by delaying the start of line trigger (SOL) 2702 to a point when the phase difference between the transmit clock and the receive clock is at a known state. The SOL trigger 2702 is synchronized by the TX_RX_SYNC pulse. The TX_RX_SYNC pulse is generated by the TX_Sync Timer 2722. The synchronized start of line trigger (SOL_S) 2704 can now start the control timing signals for the transmit beamformer 2706 and receive beamformer data acquisition. TX_TRG is a delayed version of SOL_S that signals the transmit beamformer to begin a transmit cycle. TX_TRG is synchronized to TXCLK. The transmit beamformer 2706 generates the TXGATE multiplexer control signals and TXA/TXB transmit pulses to the front end module. RXGATE signals the receive beamformer to start data acquisition. RXGATE is synchronized to RXCLK 2710.

The phase difference between transmit 2708 and receive clocks 2710 is fixed as long as the TX_Sync_Period 2712 is calculated correctly. The TX_Sync_Period 2712 is the minimum number of transmit clock cycles required to achieve synchronization. For example, if the transmit clock frequency is 30 MHz and the receive clock frequency is 25 MHz, TX_Sync_Period 2712 will be 6 cycles of the transmit clock.

Clock Generator

The clock generator 2428 provides the appropriate clock frequencies for transmit and receive beamforming. It comprises a low jitter master clock, a programmable divider, clock buffers and re-synchronization circuits. The frequencies are: transmit frequency (fc)—25 to 50 MHz; receive frequency—20 to 50 MHz in-phase and quadrature; digital clocks—fc×2, ×4, ×8, ×16. The fastest clock used in this exemplary embodiment can be 800 MHz (50 MHz×16).

PCI Express Bridge

The PCI Express bridge 2426 connects the host CPU and the embedded CPU 2424 via a PCI bus 2410. This allows DMA transfers from the RF cine buffer 2420 to the host processor memory and vice versa. PCI Express builds on the communication models of PCI and PCI-X buses. PCI Express uses the same memory mapped address space as PCI and PCI-X with single or burst read/write commands. However, PCI Express is a point-to-point serial interconnect using a switch to connect different devices, whereas PCI and PCI-X are parallel multi-drop buses. PCI Express can be used as a chip-to-chip or board-to-board communication link via card edge connectors or over a cable.

The bandwidth of the PCI Express link may be, for example: Uplink—210 MB/s burst and 140 MB/s sustained rate for RF Data, MIS Data, and diagnostics; Downlink—20 MB/s burst and <1 MB/s sustained rate for writing control parameters.

Synthetic Aperture FPGA

The partially summed beamformer RF data from the channel boards 2416 is first processed in the synthetic aperture FPGA. The processing comprises beamformer final summation, synthetic aperture and write to FIFO.

RF Cine Buffer

Functionally, the RF cine buffer 2420 is, for example, a 1 GByte dual port RAM. The RF cine buffer 2420 is a random access memory block that stores RF data organized in lines and frames. The data can be input and output at different rates to support asynchronous signal processing. The data stream is made up of interleaved I and Q beamformed data. The FIFO buffer provides storage of the beamformer data while the memory is being read by the CPU for the next display period.

In one embodiment, buffer specifications may include, for example: Storage—300 Full Size Frames (512 ray lines× 1024 samples/line×32 bits I&Q data); Buffer Size—>629 M bytes; Input rate—140 Mbytes/sec; Output rate—140 Mbytes/sec (RF Data Rate) 32 Mbytes/sec (Video Rate).

Asynchronous Signal Processing

Figure 28:
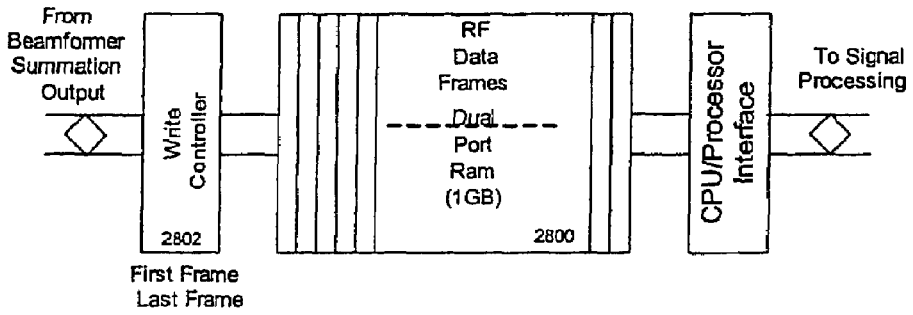
FIG. 28 illustrates an exemplary RF memory buffer for storage of beamformer output.

According to an embodiment of the described exemplary ultrasound system, it is capable of very high acquisition frame rates in some modes of operation, in the range of several hundred frames per second. The display rates do not have to be equivalent to the acquisition rates. The human eye has a limited response time, and acts as a low pass filter for rapid changes in motion. It has been demonstrated that frame rates above 30 fps have little benefit in adding to perceived motion information. For this reason, displayed ultrasound image information can be processed at a rate of 30 fps or lower, even when the acquisition rates are much higher. To uncouple acquisition from signal processing, a large RF buffer memory is used to store beamformer output data. An exemplary structure for buffering the beamformer output date is shown in FIG. 28. As shown in the FIG. 28, the memory buffer 2800 can hold many frames of RF data. For a depth of 512 wavelengths, the storage of a full line of 16 bit quadrature sampled RF uses 4 K bytes (1024 I,Q samples*32 bits/pair). With 512 raylines per frame, a 1 G byte memory buffer can then hold 512 2D frames. To keep track of frames written to the buffer, the write controller maintains "first Frame" and "last Frame" pointers, which can be read by the signal processing task, and point respectively to the first frame in the buffer available for reading, and the last frame available for reading.

During active acquisition, the beamformer summation output is written by the Write Controller 2802 to the next available frame storage area, which is typically the storage area immediately following that pointed to by the "last frame" pointer. As the data in each new frame is acquired, the "first frame" and "last frame" pointers are updated so that the data is written to the correct address in the buffer. When acquisition is stopped (freeze), the buffer then contains the last N frames, with the "first frame" pointer indicating the oldest frame in the buffer.

The signal processing module 2422 has access to the RF memory buffer 2420. It accesses one acquisition frame at a time, at the display frame rate to produce the displayed estimate data. While the system is scanning, a timer signals the signal processing module that a display frame is required. At that time, the signal processing module 2422 will check to see if a new acquisition RF frame is available, and if so, will read the data and begin processing it. If the acquisition rate is faster than the display rate, the acquisition frames will be decimated prior to processing and display. After the system has been put in freeze, the RF frames stored in the memory buffer can be processed at any desired rate, up to the original acquisition rate.

Signal Processing Module

The beamformer control board 2404 comprises a signal processor 2422 in the data path to reduce the data load and/or computation load on the host CPU. The processor 2422 may be, for example, a FPGA with a sufficient number of multipliers and memory, or a CPU such as, for example, a 970 PPC or a general purpose DSP. The signal processing functions performed are divided between the signal processing module 2422 on the beamformer control board 2404, and the main computer unit (i.e., host computer). They include post-beamforming gain control, B-Mode amplitude detection and log compression, PW Doppler spectral estimation, color flow clutter filter and frequency/power estimation, asynchronous signal processing or frame averaging. Factors that may be considered in deciding where the processing takes place include the processing speed required, the complexity of the process, and the data transfer rates required.

B-Mode Signal Processing

For B-Mode imaging, the signal processing module 2422 performs processes which may include line interpolation, detection and compression.

Color Flow Imaging (CFI) Signal Processing

In one embodiment according to the present invention, Doppler color flow imaging is combined with B-Mode imaging such that the common blocks of the B-Mode signal path and the Doppler color flow signal path are time multiplexed to provide both types of processing. Typically, the B-Mode lines are acquired in between the CFI ensembles at rate of 1 or 2 lines for each ensemble, depending on the relative ray line densities of B-Mode and CFI (typical CFI images use half the ray line density of B-Mode), as is known to one of ordinary skill in the art.

For CFI, the Signal Processing Module 2422 performs processes that may include: ensemble buffering; clutter filter; velocity estimate calculation; power estimate calculation and variance estimate calculation.

After the I and Q waveforms from the receive beamformer summed output have passed through the clutter filter, the various parameters of the Doppler signal are estimated by a Doppler frequency and power estimator in either the host computer or the CPU 2424 on the beamformer control board. The parameters estimated for each sample depth in the ensemble may include Doppler frequency, Doppler power, and the variance of the frequency estimates. These parameters may be used in a decision matrix to determine the probability that the frequency estimate is a true estimate of the Doppler spectrum, rather than a noise or clutter signal estimate. Color flow velocity estimates are derived from the Doppler frequency estimates. All of the estimates are derived using a 2-D autocorrelation method as is known to one of ordinary skill in the art.

PW Doppler Signal Processing

Pulsed Doppler acquisition may be either by itself, in duplex mode, or in triplex mode. In duplex mode, the PW Doppler transmit pulses are interleaved with the B-mode transmit pulses so that the B-mode image is updated in real time while the PW Doppler signal is acquired. The method of interleaving depends on the Doppler PRF selected. The components shared between B-Mode imaging and Pulsed Doppler processing are time multiplexed to accomplish both types of processing.

In triplex mode, Pulse Doppler is combined with B-Mode and color flow imaging. The simplest implementation of triplex mode is a time interleaving of either a B-Mode line or a CFI line, in a fixed sequence that eventually results in a full frame of B-Mode and CFI image lines. In this implementation, the PRFs for both Pulsed Doppler and CFI are reduced by half, compared with their normal single modes of operation.

The I and Q samples for each ray line are range gated (a selected range of I or Q signals are separated out from the full range available and averaged to produce a single I,Q pair), to select the region of interest for the Doppler sample volume. The length of the range gate can be varied, if desired, by the user to cover a range of depth. The resulting averaged I,Q pairs are sent to a spectral processor, as well as an audio processor, which converts the I, Q Doppler frequency data to two audio output streams, one for flow towards the transducer (forward) and the other for flow away from the transducer (reverse).

For PW Doppler imaging, the signal processing module 2422 performs processes including range gating (digital integration).

M-Mode Signal Processing

For M-Mode imaging, the signal processing module 2422 performs processes including detection and compression.

EKV Signal Processing

EKV is an acquisition method in which extremely high frame rate images are generated (1000 frames per second and higher) as a post processing operation using ECG (electrocardio-graph) signals used as timing events. EKV imaging may be implemented with either a single element mechanically scanned transducer, or with a transducer array. EKV imaging involves the acquisition of ultrasound lines at a PRF of 1000 Hz or higher at each line position in the 2-D image over a time period. The time period over which ultrasound lines are acquired at each line position, referred to as the EKV Time Period, can be for example, 1 second, which is long enough to capture several cardiac cycles in a mouse or other small animal. The acquisition of each ultrasound line involves the firing of a single transmit pulse followed by acquisition of the returning ultrasound data. For example, if there are 250 lines in the 2-D image, a total of 250,000 ultrasound lines will be acquired in the EKV data set. Each frame of the EKV image is reconstructed by assembling the ultrasound lines which were acquired at the same time during the cardiac cycle.

In one embodiment, the sequence of acquisition of the EKV data set may be such that the ultrasound line position remains static while the ultrasound lines are acquired over the time period. For example, if the time period is 1 second, and the PRF is 1 kHz, 1000 ultrasound lines will be acquired at the first ultrasound line position. The line position can then be incremented, and the process repeated. In this way all EKV data for all 250 lines in the 2-D image will be acquired. The disadvantage of this method of sequencing is that length of time required to complete the full EKV data set can be relatively long. In this example the time would be 250×1 second=250 seconds.

In a preferred embodiment which makes use of an array, the method of interleaving allows for a reduction in the length of time required to complete the EKV data set. For example if the PRF is 1 kHz there is a 1 ms time period between pulses during which other lines can be acquired. The number of ultrasound lines which can be acquired is determined by the two-way transit time of ultrasound to the maximum depth in tissue from which signals are detected. For example, if the two-way transit time is 20 μsec, 50 ultrasound lines at different line positions may be interleaved during the PRF interval. If we label the line positions L1, L2 . . . L50, one exemplary interleaving method can be implemented as follows:

| Time | Position of acquired ultrasound line |
|---|---|
| 0 μsec | L1 |
| 20 μsec | L2 |
| 40 μsec | L3 |
| . . . | . . . |
| 980 μsec | L50 |
| 1000 μsec | L1 |
| 1020 μsec | L2 |
| 1040 μsec | L3 |
| . . . | . . . |
| 1980 μsec | L50 |
| 2000 μsec | L1 |
| . . . | . . . |

The sequence in the above table is repeated until the EKV Time Period has elapsed, at which time there will be a block of data consisting of 1000 ultrasound lines acquired at 50 different line positions, from line 1 to line 50. The acquisition of the block of data is then repeated in this manner for the next 50 lines in the 2-D image, line 51 to line 100, followed by acquisition over lines 101 to 150, etc., until the full 250 line data set is complete.

The total time required for the complete data set over 250 lines is reduced by a factor equal to the number of lines interleaved, which in this example is 50. Therefore the total length of time required would be 5 seconds.

Embedded CPU

The embedded CPU 2422 on the beamformer control board 2404 is, in one embodiment, a 32-bit embedded microprocessor with a PCI interface 2426 and a DDR memory interface. The main function of the embedded CPU 2424 is data traffic control. It controls data flow from the receive beamformer FIFO 2418 to the RF cine buffer 2420, from the RF cine buffer 2420 to the signal processing module 2422, and from the signal processing module 2422 to the host PC.

The beamformer control and diagnostics information is memory mapped on the target PCI device as registers. The embedded CPU 2424 decodes the location of the registers and relays the information over the appropriate local bus. The local bus can be, for example, PCI, custom parallel (using GPIO), I2C serial, or UART serial, as each are known in the art.

Physiological Acquisition System

The physiological acquisition system 2430 (or "mouse acquisition system") filters and converts analog signals from the mouse information system inputs 2438. These signals may include subject ECG, temperature, respiration, and blood pressure. After data conversion, the data is transferred to the embedded CPU 2424 memory via local bus, and then on to the host CPU for display via the PCI Express link 2410.

Power Supply Monitoring

The beamformer control board 2404 monitors the rack power supply 2432 and lower voltages generated on each board. For example, the rack power supply 2432 may provide +48 VDC to the backplane 2408. In one embodiment, two high voltage post regulators 2436 on each channel board 2406 supply the transmit portion of the front end circuit. The beamformer control board 2404 monitors these regulators for over-current or over-voltage situations Backplane The backplane 2408 mounts to the instrument electronics card cage. In one embodiment it has blind mate edge connectors to allow each of the boards to plug in, though other connection schemes are contemplated within the scope of this invention. It provides interconnection between boards, and input/output connectors for signals outside the card cage. In one embodiment, the size of the backplane is 8 U high by 84 HP wide so that it may fit in a 8 U×19" rackmount VME-style card cage. The card cage depth may be 280 mm in one embodiment.

System Software

Figure 29:
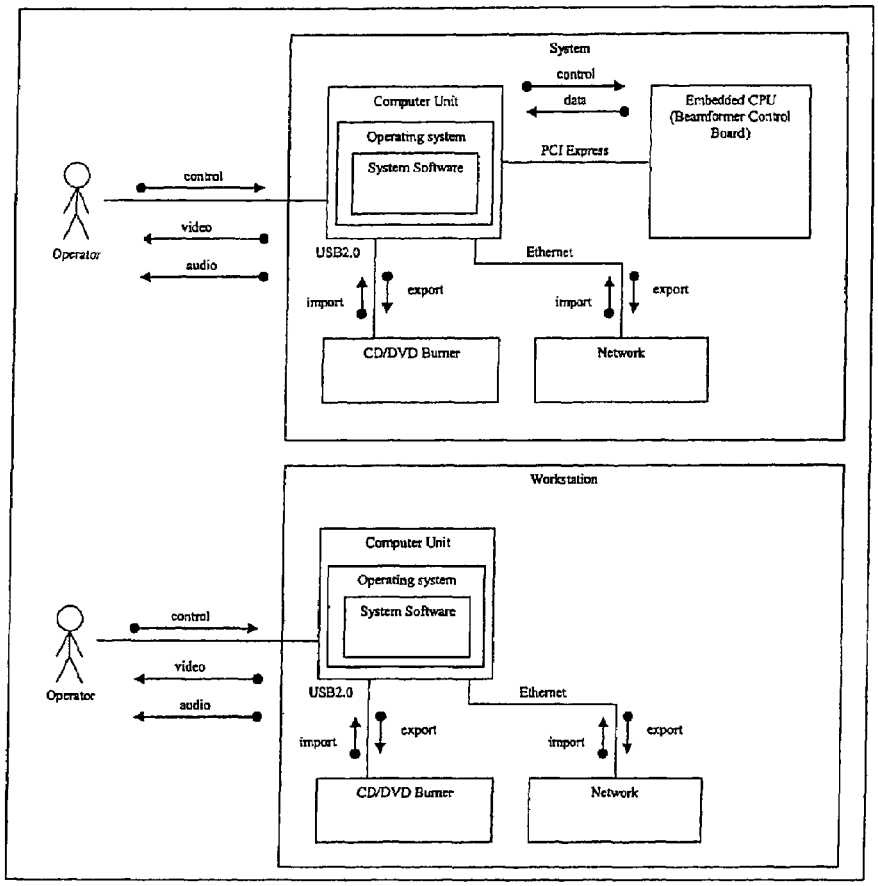
FIG. 29 illustrates an exemplary system software overview an exemplary high frequency ultrasonic imaging system.

An overview of an embodiment of system software 2330 is shown in FIG. 29. Generally, the system software 2330 operates on a processor platform such as, for example, an Intel processor platform running Windows XP operating system. The processor platform of one embodiment of the system is provided by the computer unit 2310, previously described herein. Alternatively, the system software 2330 may be loaded on a standalone workstation for reviewing studies. The workstation does not contain beamformer hardware nor does it have a transducer for acquisition of new data. It can review previously acquired study data and perform a limited set of processing functions. For example, the user may add measurements, playback at different frame rates, or change the color map.

Figure 30:
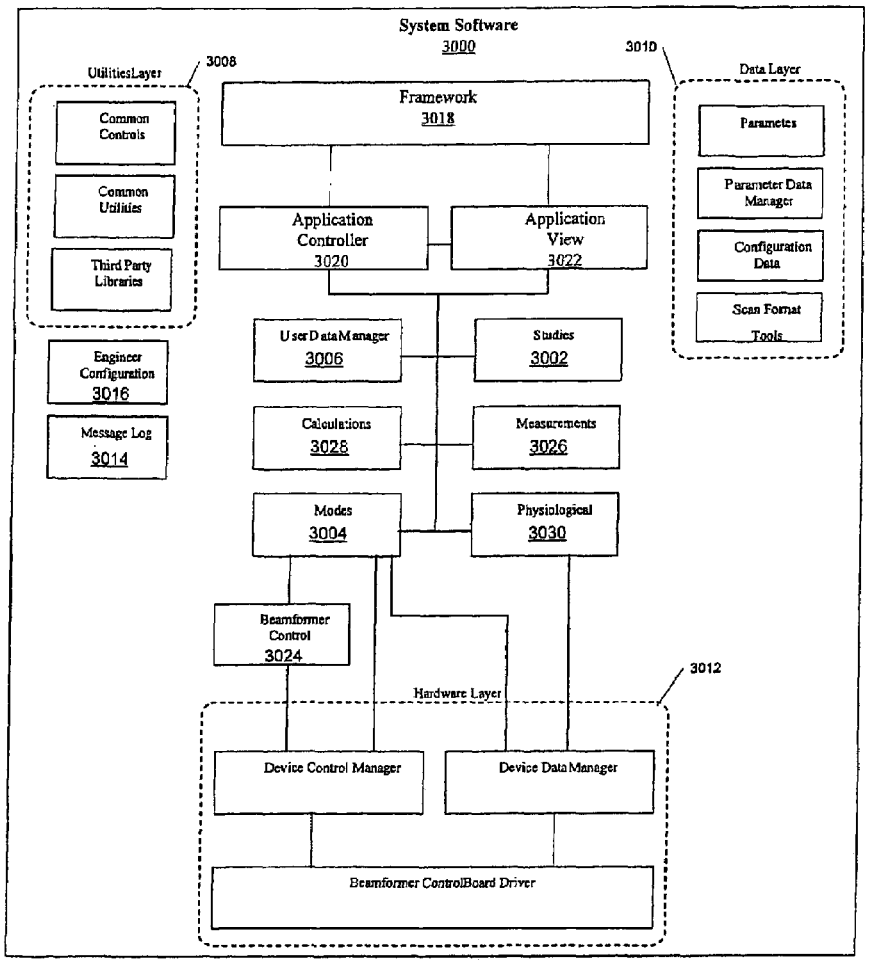
FIG. 30 is an exemplary main system software application overview for an exemplary high frequency ultrasonic imaging system.

FIG. 30 is an embodiment of a main software application that may be used to practice one or more aspects of the present invention. The system software 3000, as shown in FIG. 30, may be loaded when the system powers-up and can provide an interface for an operator of the system.

The framework 3018 which determines the overall structure of the components can be used to produce an application executable by the operating system of the processing platform of the computer unit 2310 and to interface with the operating system. For example, the framework 3018 may produce a Windows application and interface with the Windows operating system.

The application controller 3020 software component can be the state machine for the system software 3000. It may control the interaction between the operator, the system software 3000 and the front end 2308.

The application view 3022 software component can provide a foundation to support the presentation of the system software 3000 based on the state machine in the application controller 3020 software component as previously described herein.

The studies component 3002 may allow the operator to perform studies, review study data, edit content, and import or export study data. As previously described herein, there can be various operating modes supported by the system for acquiring data and can be managed by a modes 3004 software component of the system software 3000. The supported modes may include, for example, B-Mode, 3D Mode, M-Mode, PW-Doppler, Color Flow Doppler, etc. Each mode has adjustable parameters, cine loop acquisition, and main image display area, which may be managed by the modes 3004 software component. Some modes may operate simultaneously, e.g., PW-Doppler and B-Mode.

The beamformer control 3024 software component can generate the imaging parameters for the front end based on the settings in the system software 3000.

The user data manager 3006 software component may maintain user preferences regarding how the system is configured.

The measurements 3026 software component may allow the operator to make measurements and annotations on the mode data.

The calculations 3028 software component may allow the operator to perform calculation on measurements.

The utilities layer 3008 software component contains common utilities that are used throughout the application as well as third party libraries.

The hardware layer 3012 software component is used to communicate to the beamformer hardware via the PCI Express bus, as previously described herein.

The physiological 3030 software component can be used to control the physiological data collection through the hardware layer 3012 as previously described herein.

The data layer 3010 may contain a database of all the different sets of parameters required for operation. The parameters may be set depending on the current user configuration and mode of operation.

The message log 3014 and engineering configuration 3016 may be used for diagnostic reporting and troubleshooting.

Transducer Select Board

Referring back to FIG. 24, it can be seen that in this embodiment according to the present invention that the system can have one transducer connector 2438 on the front of the cart and the user can physically unplug the first transducer and then plug in another when switching transducers. In one embodiment this may be a 360-pin transducer connector 2438. In another embodiment, a transducer select board with two transducer connectors at the front panel can also be used and enables switching between transducers without physically handling the transducers.

Example 2

Figure 31:
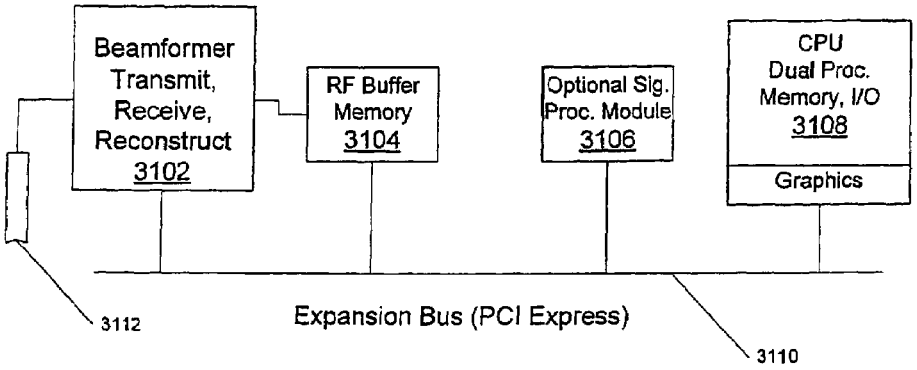
FIG. 31 illustrates an exemplary modular system overview for an exemplary high frequency ultrasonic imaging system.

Another exemplary embodiment of the high frequency ultrasound imaging system comprises a modular, software-based architecture described below and as shown in FIG. 31.

The embodiment of FIG. 31 comprises four modules, which are part of a processing unit, for the exemplary system; a beamformer module 3102; an RF buffer memory 3104; a signal processing module 3106; and a system CPU 3108. The beamformer module 3102 comprises the circuitry for transmitting and receiving pulses from the transducer, as well as the delay processing used for beamforming. Its output can be summed RF data or optionally down-converted I and Q data from quadrature sampling techniques. The output of the beamformer module 3102 may be written to a large RF buffer memory 3104, as described herein.

The CPU/signal processing module 3106 is responsible for processing the RF data from the beamformer 3102 for image formation, or Doppler sensing. The signal processing module 3106 can comprise a CPU module with the processing tasks implemented in software executing in a general purpose computing environment. Alternatively, the signal processing module 3106 can be implemented with some signal processing functions in hardware or in software executing on dedicated processors, in which case an additional signal processing module can be implemented as a plug-in card to the system CPU 3108.

If a dedicated hardware solution is chosen for the signal processing module 3106, it can be implemented with high performance CPUs. Optionally it can be implemented with digital signal processing chips (DSPs). One type of DSP which may be used is of the floating point variety, as are known in the art, and can be controlled by the host CPU, as well as being "data driven."

The system CPU 3108 can act as both a user interface/control system as well as a signal/image processing subsystem. System control information can be distributed using memory mapped I/O, wherein modules interface to the peripheral bus of the CPU module. Optionally, the system CPU 3108 can be physically separate from the beamformer module 3102 and can be connected via a PCI Express cable (or equivalent) 3110. An exemplary PCI Express cable 3110 is one that supports transfers up to 1 GB/sec and lengths of three meters. Some or all of the memory that exists on various modules can be mapped into the CPU's 3108 memory space, allowing for access to parameters and data.

The system CPU 3108 in the exemplary architecture can perform a number of real-time processing tasks, including signal processing, scan conversion, and display processing. These tasks can be managed in a manner that does not require a "hard" real-time operating system, allowing for expected system latencies in the scheduling of processing routines. In addition, the system CPU 3108 can be responsible for managing the user interface to the system, and providing setup and control functions to the other modules in response to user actions. The CPU motherboard and operating system can support multiple CPU's, with fast access to a high speed system bus, and near real-time task management.

Transmit Beamformer

The beamformer module 3102 of this exemplary system comprises a transmit beamformer. The transmit beamformer can provide functions which may include, for example, aperture control through selection of a subset of array elements, delay timing to start of transmit pulse, transmit waveform generation, and transmit apodization control. For this exemplary embodiment, a transducer array 3112 is utilized. In one embodiment, this transducer array 3112 contains up to 256 elements. To eliminate the need for high voltage switching of transmitter pulse drivers to transducer elements, the transmit beamformer component of the beamformer module 3102 may be comprised of a number of transmitters equivalent to the number of transducer array elements. For instance, in an exemplary array transducer having 256 elements the transmit beamformer comprises 256 transmitters. Optionally, the transmit beamformer can comprise less than 256 transmitters and a high voltage switching method to connect an individual transmitter to a specific element. High voltage multiplexers are used to select a linear subset of elements from a 256 element array.

Optionally, the transmit beamformer component of the beamformer module 3102 may comprise high voltage pulser drivers for all 256 elements of the exemplary array, and a switching mechanism which connects a subset of transmit waveform generators to the appropriate drivers/array elements. This optional embodiment uses 256 TX/RX switches for protection of the receiver inputs with low level multiplexing to select the subset of array elements for the receive aperture. The low level multiplexing can optionally be combined with the TX/RX switches and in some cases has less attenuation of the receive signals and faster switching, when compared with a high voltage MUX scheme.

Transmit delays of 1/16 wavelength can be used and provide appropriate focusing and side lobe reduction in the transmit beam. For desired steering and focus control, the maximum delay times, when measured in wavelengths, can be at least 0.7 times the largest transmit aperture. For example, with 128 transmitters and an array spacing of 1.5 wavelengths, the largest transmit aperture is 192 wavelengths. At 20 MHz center frequency, the maximum transmit delay times can be at least 6.72 microseconds.

For 1/16 wavelength accuracy, the highest center frequency of interest specifies the delay resolution. At 50 MHz, this gives a delay accuracy of 1.25 nsec, which uses the equivalent of an 800 MHz clock and a 13 bit counter to achieve the maximum delay time of 6.72 usec. Optionally, instead of a high frequency clock a four phase clock at 200 MHz can be used. This would allow selecting a specific transmit delay by selecting one of the four phases of the 200 MHz clock as input to an 11 bit counter, which is preloaded with the number of 200 MHz clocks in the delay time.

Figure 32:
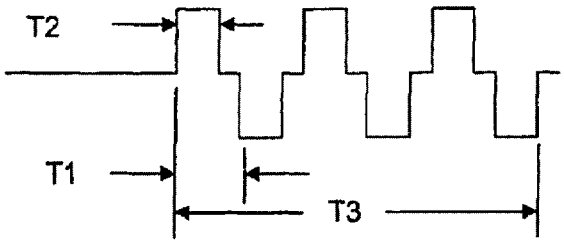
FIG. 32 displays an exemplary transmit frequency, half cycle on time, and pulse durations.

The transmit beamformer component of the beamformer module 3102 further comprises a bi-polar transmit pulser. This type of pulser drive is typically specified with three parameters: T1, which is a transmit frequency (duration of half cycle); T2, which is a half cycle on time (duration of either positive or negative half cycle pulse); and T3, which is a pulse duration (number of half cycle pulses in total transmit). These durations are shown in FIG. 32.

The control of the half cycle pulse duration, T2, allows for closer approximation to a sine wave drive, with improved transducer output. It can also be used to obtain a somewhat crude apodization of the transmit pulse power, provided that sufficiently fine control of the duration is provided.

Transmit apodization can be used to reduce spurious lobes in the transmit beam, which can be either side lobes or grating lobes. Apodization of the transmit aperture results in reduced power output and worse lateral resolution, so it is not always desirable. Often a small amount of apodization capability, such as providing for only a few levels of power output, is sufficient to achieve a good compromise between spurious lobe reduction and lateral resolution. The pulse width modulation scheme mentioned above for transmit waveform generation is one possible means of providing limited transmit apodization. A second method is to provide not one, but possibly four or more levels of high voltage for the pulser drivers, with a means to select one of these levels on each pulser.

Receive Beamformer

The beamformer module 3102 also comprises a receive beamformer component. There are several different receive beamforming implementations which can be used in the exemplary system. The digital methods discussed below have least one A/D converter for each element in the receive aperture. In this exemplary embodiment, the A/D converter bit depth is 10 bits, which gives the desired beamforming accuracy at −50 dB signal levels. The A/D dynamic range is chosen to reduce spurious lobes and thus provide contrast resolution as desired. Eight bit A/D converters can be used if appropriate. Embodiments of the exemplary system use 64 receive channels, combined using synthetic aperture to implement a 128 channel receive aperture for applications where maximum frame rate is not needed. One optional method for digital receive beamforming implementation samples the ultrasound signals from the individual elements at a rate which is at least twice as high as the highest frequency in the signal (often called the Nyquist rate.) For example, a 50 MHz, 100% bandwidth transducer the Nyquist sampling rate is 150 MHz or higher.

Bandwidth Sampling

Another optional sampling method for the receive beamformer component of the beamformer module 3102 is bandwidth sampling. Sampling theory, as known to one skilled in the art, provides that if a continuous function only contains frequencies within a bandwidth, B Hertz, it is completely determined by its value at a series of points spaced less than 1/(2*B) seconds apart. Sampling a band-limited signal results in multiple copies of the signal spectrum appearing at a fixed relationship to the sampling spectrum. Provided these replicated spectra don't overlap, it is possible to reconstruct the original signal from the under-sampled data. For example, consider a signal with a maximum bandwidth of 20 MHz centered at 30 MHz, and sampled at a rate of 40 MHz. In this situation, the spectrum is replicated as shown in FIG. 32. The original spectrum is replicated in the 0-20 MHz portion of the frequency spectrum (it is also reflected about the fs/2 frequency, but this can be accounted for in subsequent signal processing), where the 40 MHz sample rate is adequate to preserve all the information in the signal.

Figure 33:
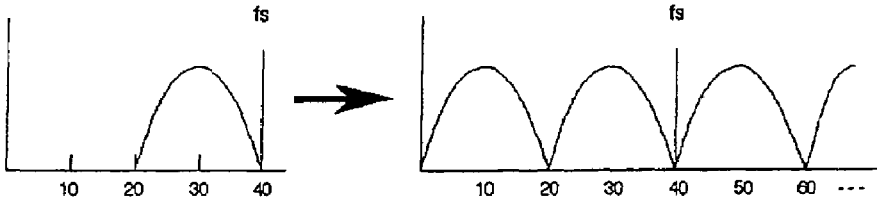
FIG. 33 illustrates exemplary bandwidth sampling of 30 MHz signal spectrum.

FIG. 33 illustrates bandwidth sampling of 30 MHz signal spectrum, which may be utilized in an embodiment of the receive beamformer component of the beamformer module 3102. Sampling the signal spectrum in FIG. 33 using normal Nyquist sampling requires a sample rate of 80 MHz or higher. Using bandwidth sampling at ¾ of the wavelength, as described above, transducer center frequencies up to 60 MHz can be managed with 80 mega samples per second (MSPS) 10 bit A/D converters, which are known in the art and are available from several vendors. In the example given above, the signal spectrum had no frequency components outside of the 20 MHz bandwidth region (66.7% of the center frequency). In practice, a transducer spectrum often has skirts that can extend beyond the 66.7% bandwidth region, creating overlapping spectra and inaccurate signal reconstruction. These skirts can be dealt with by using a bandpass anti-aliasing filter prior to the A/D converter that keeps the power in the spectral skirts extending beyond the bandwidth limits to a desired level, such as 5-10%.

Quadrature Sampling

Another form of bandwidth sampling, known as quadrature sampling, can optionally be used in an embodiment of the receive beamformer component of the beamformer module 3102. In this sampling method, two samples are taken at 90° phase with respect to the center frequency. These samples can be repeated at an interval which is consistent with the bandwidth of the signal. For example, if the quadrature samples are taken at every period of the center frequency, the sample rate supports a 100% bandwidth signal. The sample pair resulting from quadrature sampling is not a true complimentary pair, since the samples are taken at different times, however they are true samples of the analytic waveforms, and concurrent quadrature samples can be found by interpolating the samples of the two I and Q sampled waveforms to the same point in time. Quadrature sampling may be implemented with one high sample rate converter sampling at four times the center frequency or with two lower frequency converters each operating at the center frequency but with clocks differing in phase by 90° with respect to the center frequency Nyquist Sampling Optionally, yet another form of sampling can be used in the receive beamformer. This form of sampling is Nyquist sampling combined with bandwidth sampling. Normal Nyquist sampling is used for the lower transducer center frequencies and bandwidth sampling for the higher frequencies. Commercially available 10 bit A/Ds with maximum sample rates of 105 MSPS are available. With this sample rate capability, a 30 MHz center frequency transducer with 100% bandwidth can be sampled adequately at Nyquist rates. At 40 MHz, Nyquist sampling can be used for transducers with bandwidths up to approximately 60%, so for this center frequency or higher, bandwidth sampling can be used. If these higher sample rates are used, the beamformer processing circuitry also accommodates the higher clock rates and increased storage requirements.

A variation of quadrature sampling can be used to provide a higher bandwidth beamforming capability for those applications that can benefit from it (for example, harmonic imaging) In this method, two quadrature sample pairs may be acquired for every cycle of the center frequency. For example, consider the sampling of a signal which has a center frequency of 30 MHz and significant spectral content beyond 100% bandwidth, such that the spectrum extends to frequencies less than 15 MHz and/or greater than 45 MHz. Two A/D converters per channel may be used to acquire the RF signal at that channel, each sampling periodically at twice the center frequency, 60 MHz. The sample clock of the second A/D converter is delayed by ¼ the period of the 30 MHz center frequency relative to the sampling clock of the first A/D converter. Every second sample acquired by the A/D converters will be multiplied by −1. The sample stream originating from the first A/D converter will then be the down-converted quadrature (Q) sample stream, and that originating from the second A/D converter becomes the down-converted in-phase (I) sample stream. The fine delay required for receive beamforming may be implemented by interpolation of the quadrature samples. This method allows for accurate sampling of the RF signal over 200% bandwidth of the center frequency.

In an alternative method of providing higher bandwidth beamforming capability which requires one A/D converter per receive channel, the RF output of the beamformer can be formed using two acquisition pulses, similar to a synthetic aperture approach. For example, consider a 30 MHz signal spectrum with 100% bandwidth, so that the −6 dB spectrum extends from 15 to 45 MHz. In this case, the signal can be sampled at a 60 MHz sample rate, and the sign of every other sample flipped, to provide a down-converted sample stream that can be taken as the Q channel of a quadrature down-conversion scheme. On the next acquisition, the sampling clock is delayed by ¼ of the period of 30 MHz, providing (after flipping the sign of alternate samples) the I quadrature waveform. These two quadrature waveforms are then time shifted and combined after beamforming to reconstruct an RF signal that is accurate for 200% bandwidth of the 30 MHz center frequency. This is adequate to capture all the information from an ultrasound transducer with 100% bandwidth. The frame rate is reduced by half compared with single pulse ray line acquisition. Higher frame rates can be achieved over a region of interest by reducing the number of image lines.

In the exemplary embodiment of FIG. 31, receive beamformer delay implementation is performed using the interpolation method. In this approach to beamforming, the A/D converters all sample concurrently, at a constant sample rate (using bandwidth or quadrature sampling). The delays for steering and dynamic focusing are implemented in two steps: 1) a coarse delay stage that implements a delay which is an integral number of sample clocks cycles, and 2) an interpolation filter that interpolates to 1/16 of a wavelength time positions in between the coarse samples. The coarse delay stage performs the function of a programmable shift register, whose maximum length is equivalent to the maximum delay time desired in sample periods. The order of these two stages can be reversed if desired, depending on implementation considerations.

Bandwidth sampling interpolation may be described using the following example. For an exemplary 30 MHz array using bandwidth sampling, the sample rate on all A/D converters can be set to 40 MHz, providing a 66.7% bandwidth. With 128 receive channels, about 10 micro-seconds is desired for maximum delay, thus implementation uses a programmable shift register of about 400 stages. At 40 MHz, the programmable interpolators need only calculate one of eleven intermediate sample values (for 1/16 wavelength accuracy), equally spaced between adjacent 40 MHz samples. The interpolators can be specifically designed for bandwidth sampling to provide for accurate signal reconstruction. Samples can be taken from the output of all channels' interpolators, and summed to produce the sampled RF waveform for the desired beamforming direction.

The signal reconstruction process for interpolating between bandwidth sampled data points is simplified for the example 30 MHz array given above. In this case, every odd sample can be taken as samples of the Q component of the quadrature baseband representation of the signal (with alternate sign), while even samples can be considered to be samples of the I component. A simple bandlimited interpolator can be used to find the I and Q signal values at the appropriate intermediate time point, which can then be combined to reconstruct the RF value. If desired, all of the bandwidth sampled data points can be down-converted by the interpolation filters, resulting in a baseband quadrature sampled beamformer output, which can simplify downstream signal processing.

Quadrature sampling interpolation may be described using the following example. In this example, the input signals for each channel are assumed to be quadrature sampled, at one quadrature pair per cycle of the transducer center frequency, providing an input bandwidth of 100% around the center frequency. The two samples in the pair are taken at 90 degrees phase difference with respect to the center frequency, which provides actual samples of the Q and I baseband signals, but the waveforms are sampled at different points in time. Before the Q and I data can be combined, this sampling offset is corrected using interpolation filters. The interpolation required for correcting the sample offsets can optionally be incorporated into the interpolation filters used for beamforming.

Since the quadrature sampling method proposed generates baseband I and Q signals, the interpolation filters are operating on these signals, rather than the RF waveforms. The samples for all channels are taken at the same time, which leads to I and Q waveforms with the same phase relative to an RF waveform common to all channels. This is equivalent to using mixers on all channels to derive I or Q signals, where the carrier frequency for the mixers all have the same phase. However, correct summation of the I and Q samples from different channels can be provided by adjusting the carrier phase on each channel to match the phase of the time delayed echo waveforms. This amounts to a phase rotation of the interpolated I, Q samples according to the interpolation point relative to 0 degrees phase of the RF center frequency period. This rotation can also be incorporated into coefficients of a FIR interpolation filter, to produce a corrected I and Q output from each channel that can be summed coherently.

Figure 34:
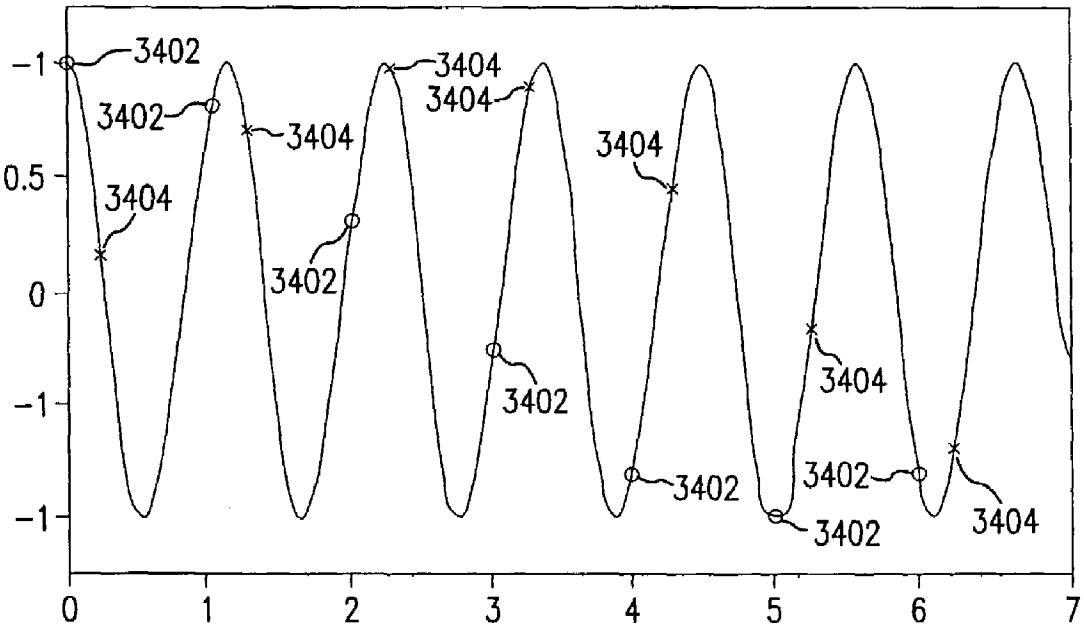
FIG. 34 illustrates an exemplary quadrature sampled sine wave at 0.9 times the sample frequency.

As way of explanation of the quadrature sampling interpolation beamforming method, one can first consider a simpler conceptual model, rather than an actual implementation. In this model, interpolation will be implemented to 16 separate points over the period of the center frequency, providing 1/16 wavelength accuracy for beamforming. This level of accuracy has been shown to be sufficient to provide no significant degradation of beam profiles. Considering a quadrature sampled waveform as shown in FIG. 34, the signal is a sine wave whose frequency is 0.9 times the frequency of sampling (which is, for example, 1 Hz in this instance). The Q samples are shown as 'o's 3402, while the I samples are shown as 'x's 3404. As can be seen from the figure, the Q and I samples are samples of much slower changing waveforms, which represent the baseband Q and I waveforms. The interpolation filters operates on these waveforms, to compute 16 interpolation points per period of the sampling frequency.

Referring to FIG. 34, which shows a quadrature sampled sine wave at 0.9 times the sample frequency. The interpolation points are chosen so that the actual sample values don't fall on an interpolation point. This provides that the filter function inherent in the interpolation filter is applied to all points. The positions of the 16 interpolated points with respect to the Q and I sample points are shown in FIG. 34A.

Typically, a four point FIR filter is sufficient for accurate interpolation. To interpolate the points 0-3, between Q and I samples, a window of eight samples can be used, as shown in FIG. 34B.

Figures 34A, 34B, 34C:
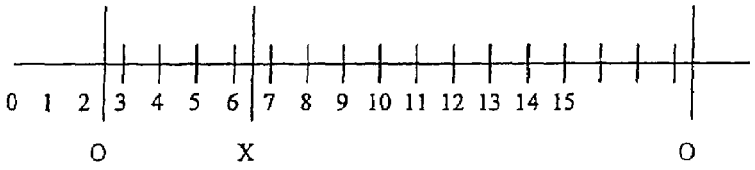
FIG. 34A is an exemplary illustration of the 16 sample points of FIG. 34 with respect to Q and I sampling points.
FIG. 34B is an exemplary illustration of a window of eight samples used by an exemplary FIR filter for interpolation of points 0-3, between Q and I samples.
FIG. 34C is the exemplary window of FIG. 34 moved forward by one sample in order to interpolate points 4-15.

To interpolate the points 4-15, the window is moved forward by one sample, as shown in FIG. 34C.

Using these windows, a set of eight coefficients for each interpolation position can be computed, which when multiplied times the sample values in the window, yields the interpolated I and Q values. In the case of the first window, the interpolated I value would be the sum of the even numbered products (0,2,4,6) while the Q values would be the sum of the odd numbered products (1,3,5,7). In the case of the second window, the I and Q values would be reversed.

Figure 35:
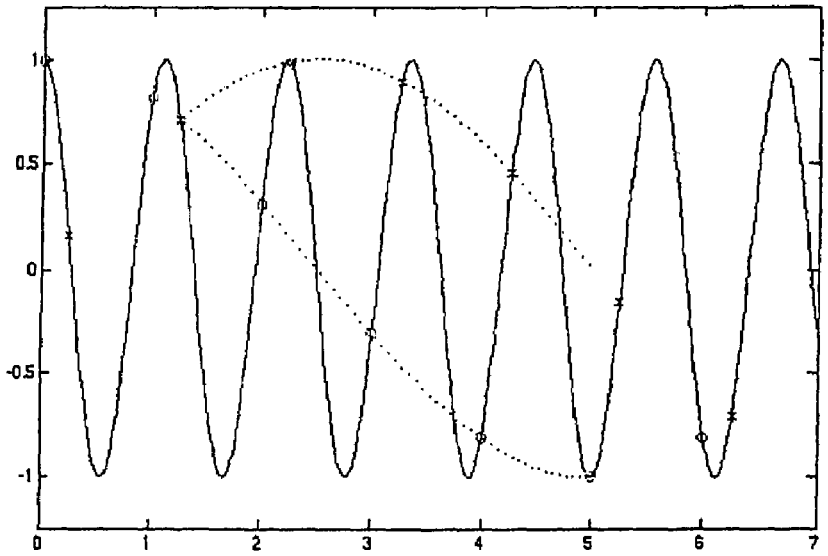
FIG. 35 displays exemplary interpolated points for I and Q waveforms.

FIG. 35 is a plot of the interpolated values for the example sine wave given in FIG. 34 over the sine wave of FIG. 34. In the figure, the interpolated points are shown as the dotted lines and start after the fourth sample point, which is the first position that a window can be applied (in this case, window #2).

Figure 36:
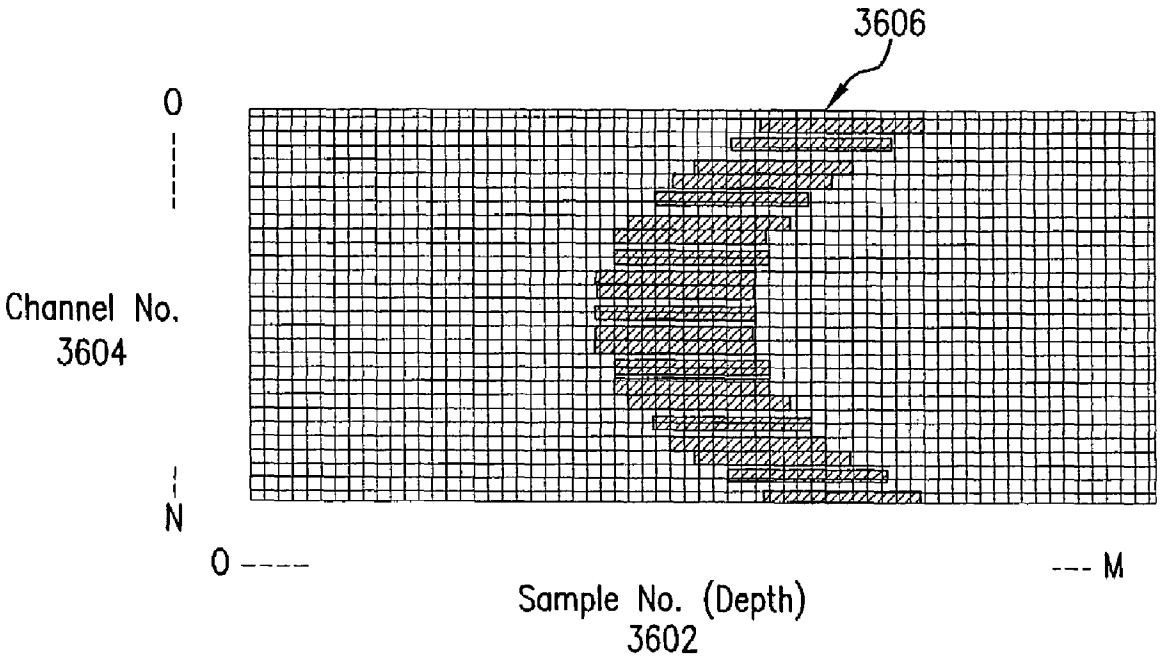
FIG. 36 displays exemplary quadrature samples data set for single ray line acquisition from a linear array.

FIG. 36 is an illustration of a data set for the acquisition of a single ray line of echo information from a linear array, consisting of the quadrature sampled signals from each of the transducer elements over a depth range. This data set can be viewed as an array with depth 3602 along one axis and channel number 3604 along the other. To reconstruct a single range point along the ray line from the data set above, an eight sample window is positioned in each channel's data row at the appropriate sample number, which corresponds to depth, and one of the 16 interpolation points is chosen which provides the exact delay required. As shown in FIG. 36, the various channel windows are positioned along a parabolic arc 3606, which corresponds to the curvature of focus needed to reconstruct the range point. The beamforming parameters for the range point are then defined by providing a starting sample number and interpolation number for each channel included in the aperture.

Figure 37A:
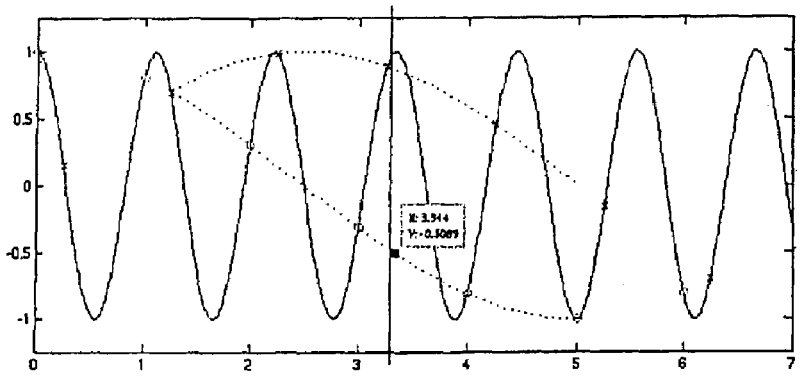
FIGS. 37A and 37B display two exemplary channel signals returned from the same range point, but with a path length difference corresponding to one-half wavelength.
Figure 37B:
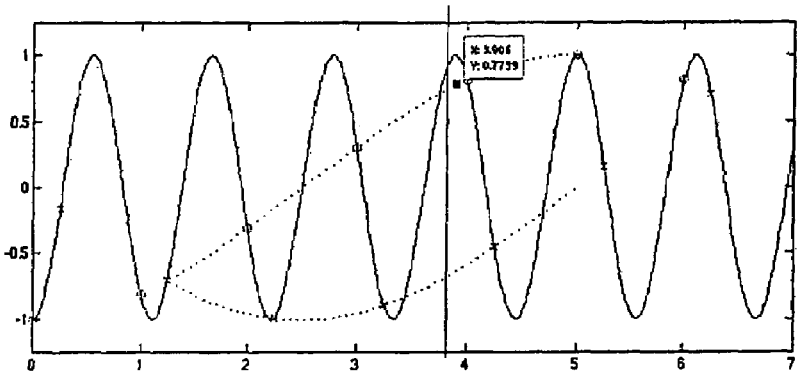

After applying the appropriate interpolation filters to each of the channel data shown above, and I and Q sample is obtained for each channel that corresponds to the appropriate delay for the range point. As previously described herein, these I and Q sample pairs can not be simply summed to derived a beamformed I,Q pair, since the phase of the I,Q sample from each channel is different. Before the I,Q pairs from each channel can be summed, each channel's I,Q pair is phase rotated to correspond the same phase with respect to the delay time implemented. For example, if two channels are receiving an echo return, where the path length difference to the range point corresponds to exactly ½ wavelength of the echo frequency, and these echo returns are sampled at the same times by our quadrature sampling scheme, the samples will fall on different points on the RF signals, and the resulting I,Q waveforms will be 180 degrees out of phase. This situation is illustrated in FIGS. 37A and 37B, in which the reconstruction points on the waveforms of the two channels are indicated by the vertical lines. When the I and Q values at the reconstruction point from the waveforms of the two channels are summed in the beamformer they should add constructively, however, it is apparent that the values are quite different and will not add constructively. To sum the two I and Q values a vector rotation must be performed first. The amount of rotation is calculated by determining the distance of the reconstruction point from the start of a sample period, which is effectively the interpolation point number times 1/16 wavelength (plus 1/32 of the period, to be precise). This distance can be converted into an angle by taking the fraction of the total period and multiplying by 2*pi. The rotation equations are then given below:

$$Qr=I*\sin(angle)+Q*\cos(angle) \quad (1)$$

$$Ir=I*\cos(angle)-Q*\sin(angle) \quad (2)$$

Using these rotation equations on the interpolated I and Q samples allows the rotated I's and Q's to be summed coherently. The rotation of the I and Q samples can be incorporated into the 8 coefficients used for interpolation. For example, when using the first interpolation window, where the even samples are I samples, the sin (angle) in equation (1), above, can be multiplied by each of the I coefficients, and the cos (angle) term multiplied by each of the Q coefficients. The resulting FIR filter then provides the rotated Q value, when all product terms are added together. Similarly, another set of coefficients can be used to compute the rotated I value. In this scheme, the FIR filter operates twice per sample period, using different coefficients, to produce an output stream of rotated Q and I values. This stream can be summed with the stream of rotated Q and I values from other channels to produce the beamformer output, which in this case is interleaved I,Q data representing the down-converted summed RF. Alternatively, the interpolation of the Q and I values may be implemented with separate FIR filters, each with 4 coefficients. In this scheme, the phase rotation is implemented in a stage following the interpolation.

The sampling scheme in which two quadrature pairs are acquired for each period of the center frequency also requires a phase rotation after interpolation of the quadrature samples. In this scheme two A/D converters per channel may be used to acquire the RF signal at that channel, each sampling periodically at twice the center frequency. The sample clock of the second A/D converter is delayed relative to the sampling clock of the first A/D converter by ¼ of the period of the center frequency. Every second sample acquired by the A/D converters will be multiplied by −1. Interpolated values can be calculated for 16 separate points over the period of the center frequency, or for 8 points over the period of the sample clock. The interpolation points calculated over a span of two sample clock periods may be numbered from 0 to 15. The amount of phase rotation required is the interpolation point number multiplied by 2*pi/16. For example, when the interpolation point is located at ⅛ of a sample clock period after the start of odd numbered sample clock cycles, the amount of phase rotation will be 2*pi/16. When the interpolation point is located at ⅛ of a sample clock period after the start of even numbered sample clock cycles, the amount of phase rotation will be 2*pi*(9/16). The interpolation points may be shifted by 1/32 of the center frequency so that the actual sample values don't fall on an interpolation point on order to ensure that the filter function inherent in the interpolation filter is applied to all points. After the phase rotation, the values can be summed to provide the beamformer output. The amplitude of the envelope of the received signal output from a quadrature beamformer may be determined by calculating the square root of the sum of the squares of the I and Q samples. A compression curve may then be applied to the envelope amplitude values. Doppler processing can use the summed I and Q sample stream directly to derive Doppler frequency estimates and/or compute FFT spectral data.

Figure 25:
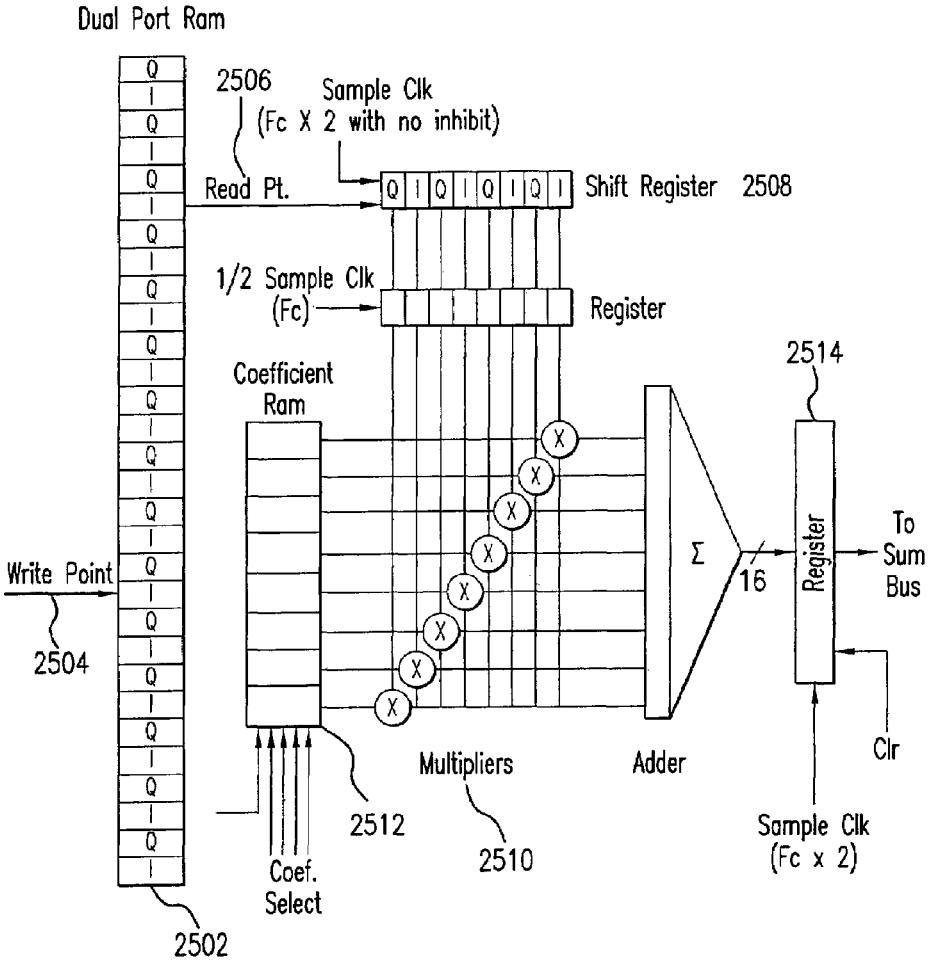
FIG. 25 shows an exemplary single channel delay scheme for quadrature sampling.

A possible implementation for interpolation filters operating on quadrature samples is described below. In one embodiment the interpolation filters and control logic can be implemented with an FPGA device. As provided above in reference to FIG. 31, receive beamformer delay implementation may be performed using the interpolation method. A high level diagram of a delay implementation is shown in FIG. 25. This diagram shows the functions after A-to-D conversion for a single beamformer channel. The outputs of the two A/D converters are multiplexed into a single sample stream at a constant rate of two times the center frequency. For 10 bit A/D converters, we then have a series of 10 bit samples coming from the A/D converters, with the first sample designated as a Q sample, followed by the I sample of the quadrature pair. This stream is the input to the dual port ram 2502 shown in FIG. 25.

At the start of an acquisition line, a write pointer 2504 and a read pointer 2506 in the dual port ram are reset to the top of the ram 2502. As each new sample comes in, the sample is written to the ram 2502 at the address of the write pointer 2504, which is then advanced to the next sequential location. When the write pointer 2504 reaches the end of the ram 2502, it wraps around to the beginning of the ram 2504 for the next write operation. The dual port rams 2502 are large enough to store samples for the maximum delay required by the steering and focusing needed for the acquisition line.

The input side of the dual port ram 2502, with the writing of each new sample and subsequent incrementing of the write pointer 2504, needs no channel unique control mechanism, since all channels can write their input data at exactly the same time and to the same addresses. The output side of the dual port ram 2502 uses independent channel control. FIG. 26 illustrates one mechanism for implementing the control signals required for a single channel. In the embodiment of FIG. 26, a control ram's 2602 address is incremented at the input sample clock rate (2× the center frequency, Fc). The ram 2602 then provides a registered output 2604 where each bit provides an independent control signal.

Returning to FIG. 25, it is shown and described how the receive delays are implemented in one embodiment according to the present invention. For echoes returning from a point located along the centerline of the receive aperture, the echo first appears in the signals from the element or elements closest to the center of the aperture, then later in the elements near the outer portion of the aperture. This means that to align echoes in signals from the center and the outer edge of the aperture, the center signals can be delayed a period of time before they can be summed with the signals from the outer edge. In the dual port ram 2502 example, longer delays are achieved by letting the read point 2506 lag further back behind the write point 2504. Therefore, the center channel in the aperture will have the greatest difference between read point 2506 and write point 2504, while the outer channels will have the smallest difference.

For dynamic focusing, the focal point is moved outward along the receive line at the half the speed of sound, so that focal point is always at the location of the echo being received. For a constant aperture, as the focal point moves out in range, the delay between the center and outer channels of the aperture decreases. With dynamic aperture, or constant f (i.e., focal length divided by the aperture size) number operation, the delay between inner and outer channels increases until the maximum aperture is reached, then the delay decreases.

Using dynamic aperture and dynamic focus with the dual port ram delay scheme, yields the following operation of the dual port ram pointers 2504, 2506: The center channel is delayed by the maximum delay amount (the amount for the full aperture) by letting the write pointer 2504 move ahead of the read pointer 2506 until the delay is achieved. At that point, the read pointer 2506 is moved ahead at the same rate as the write pointer 2504. An outer channel's initial delay is set by letting the write pointer 2504 move ahead of the read pointer 2506 by the appropriate amount. This initial delay offset can be less than the offset of the read 2506 and write pointers 2504 of the center channel. At this point, the read pointer 2506 is moved ahead at the same rate as the write pointer 2504 until the channel is made active in the aperture.

After a channel is made active in the aperture, its delay gradually increases with time to approach that of the center channel. This is accomplished by occasionally not moving the read pointer 2506 ahead when the write pointer 2504 is moved. This increases the offset between the read 2506 and write pointer 2504 gradually with time.

Figure 26A:
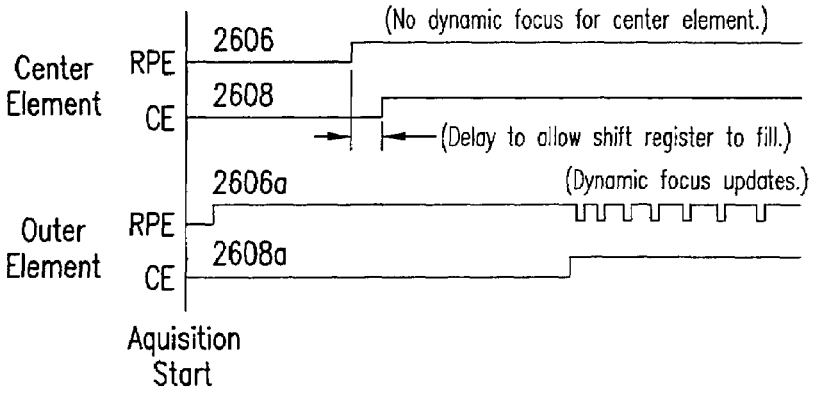
FIG. 26A shows exemplary beamformer delay control signals for center and outer elements of an arrayed transducer.

The above operation can be directed with only two binary state control signals as shown in FIG. 26A. The first signal is a read pointer advance enable (RPE) 2600, which allows the read pointer 2506 to advance concurrently with the write pointer 2504. When this signal is true at the time of the Fc*2 sample clock, the write pointer is advanced after the data is written to the dual port ram 2502, and the read pointer 2506 is advanced at the same time. When the signal is false, the write pointer 2504 is advanced following a write operation, but the read pointer 2502 remains the same. The RPE control signal 2606, 2606a is used not only to set the initial delay of a channel, but also to implement the dynamic focus coarse delays.

The second control signal (CE) 2608, 2608a merely specifies when the channel's output becomes active, so that it participates in the summation of all active channels. This can be accomplished by the CE signal 2608, 2608a controlling the 'clear' input of the final output register of the interpolators. A channel is made active in the aperture according to when its element sensitivity pattern allows it to receive the returning echoes with less than some threshold amount of attenuation. This time must be consistent with the initial delay time implemented by the first control signal. It should be noted that the CE signal 2608 specifies the time a channel becomes active in terms of the number of quadrature samples from the start of the acquisition line. This is because when a channel first participates in the sum of channels, it must contribute a quadrature pair. In the case of the Fc*2 sample clock, there are two clocks for every quadrature sample pair.

FIG. 26 illustrates the control signals as they might appear for a center element (2606 and 2608), and an element at the outer edge (2606a and 2608a) of the full aperture. However, with an even number of channels/elements, there is no actual center element, since the center of the aperture falls between two elements.

For the center channel, RPE 2606 is held low for the maximum delay time needed. This allows the write point 2504 to move ahead while the read point 2506 stays put. After the delay time is reached, RPE 2606 is set high (true) to allow the read pointer 2506 to advance at the same rate as the write pointer 2504. Since there is no dynamic focus required for the center channel, RPE 2606 remains high for the remainder of the acquisition line. The center channel CE signal 2608 brings the channel active shortly after the delay time is reached. The offset is to allow the shift register and register used for the interpolation filter to fill. The CE signal 2608 then removes the clear on the output register so the channel's data can enter the summation bus.

For the outer channel, RPE 2606a is held low for only a short time, since its initial delay is much shorter than the center channel. Then RPE 2606a is set high, allowing this delay to be maintained until the channel is made active. At that time, the RPE signal 2606a is set low for a single clock cycle occasionally to implement the dynamic focus pattern. The CE signal 2608a removes the clear on the output register when the channel can participate in the summation.

Referring back to FIG. 25, the interpolation filters provide the fine delay resolution for beamforming. There are 16 interpolation points per wavelength of the center frequency, providing 1/16 lambda delay resolution. For each interpolation point, two eight point FIR filters are applied—one to generate the analytic signal I sample, and the other to generate the Q sample. This means that the interpolation filter operates twice per period of the center frequency, or at the Sample Clk (Fc*2) rate. The I and Q samples are output in succession to the output register, which if enabled, feeds the samples into the summation bus.

The input for the interpolation filters comes from the read address of the dual port ram 2502, which typically advances by one sample (I or Q) for each Sample Clk (Fc*2). When a read is performed of the dual port ram 2502, the sample is input to an eight sample shift register 2508, which holds the last eight samples read. If the read operation of the dual port ram 2502 is not enabled (RPE low), then no data enters the shift register 2508, and the read pointer 2506 is not advanced. The shift register 2508 still holds the last eight samples, and no samples are lost when the read pointer 2506 does not advance; the read pointer 2506 simply falls further behind the write pointer.

Every two sample clock cycles, the samples in the shift register 2508 are transferred in parallel to the inputs of the interpolation filter multipliers 2510. There they remain for the two multiply/accumulate operations that generate the I and Q outputs. When no dynamic focusing is occurring, the samples moved to the multiplier inputs shift forward in time by two samples for each center frequency period. The filter then outputs an I and Q sample for each period of the center frequency. With dynamic focus, occasionally the read cycle of the dual port ram is disabled, and the samples moved to the multiplier inputs shift forward by only one sample. This allows the interpolation point to move forward in time by less than a full period of the center frequency. With dynamic focus on an outer channel, the interpolation point is gradually moving back in time, towards the same time as the center channel.

The coefficients used by the interpolation filters are stored in a small ram 2512, which can be loaded by the system CPU. The ram 2512 can hold 32 sets of coefficients, 16 for the I interpolation point and 16 for the Q interpolation point. The coefficients are selected by five address lines, four of which are control lines that come from the control ram 2602. These four lines must provide a new address every other sample clock (Fc*2). The other line selects the I or Q coefficient set for the interpolation point chosen, and can be toggled with the operation of the filter, producing an I and Q sample every period of the center frequency. Finally, the output register 2514 for the interpolation filter holds the output samples before they enter the summation bus. This register's clear input is controlled by the CE control line. This allows a channel to be disabled from contributing to the sum bus until the interpolation output is valid.

Figures 1, 25B:
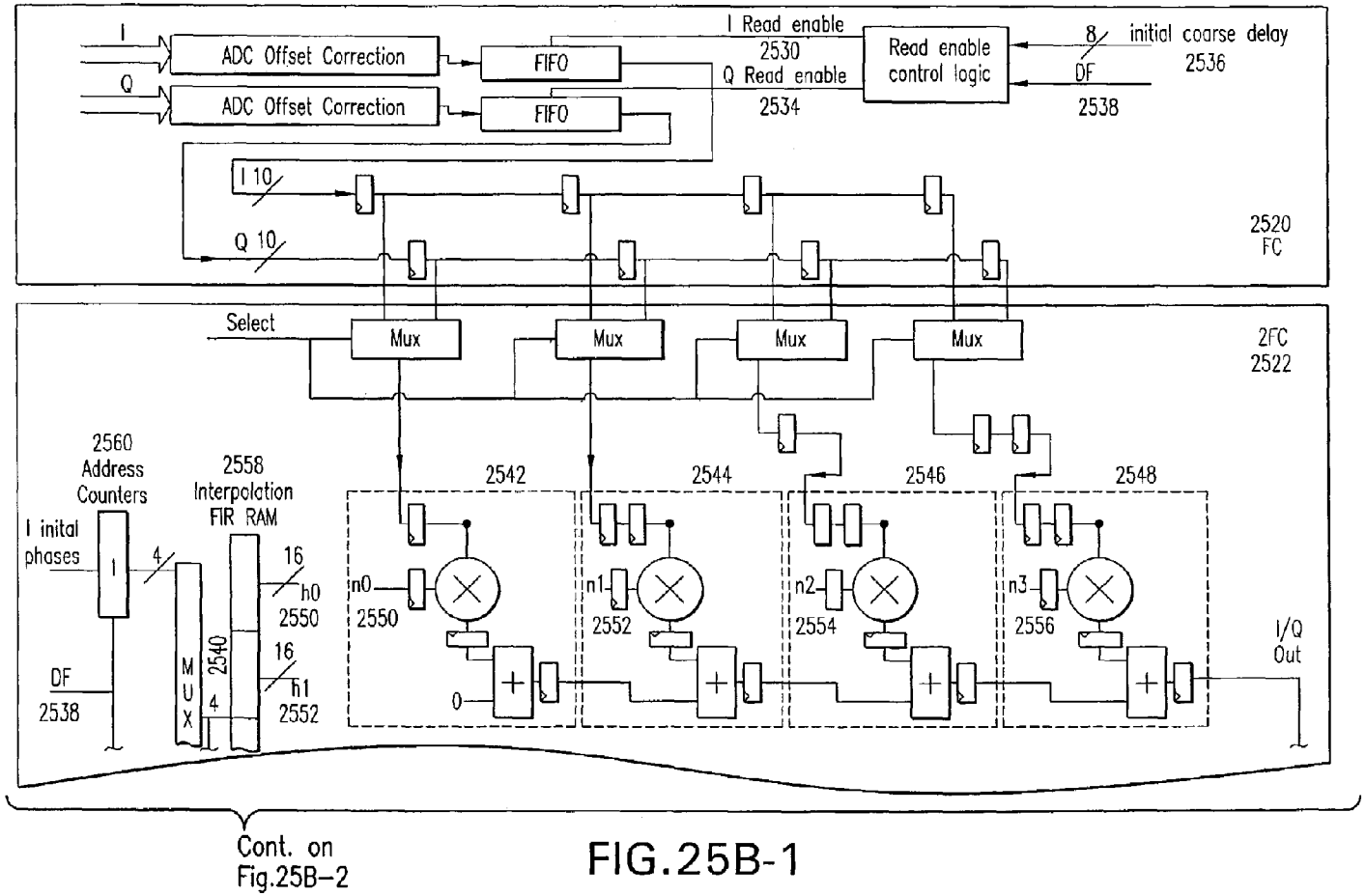
FIG. 25B is an alternative way of implementing interpolation filters, phase rotation and dynamic apodization according to an embodiment of the invention.
Figures 2, 25B:
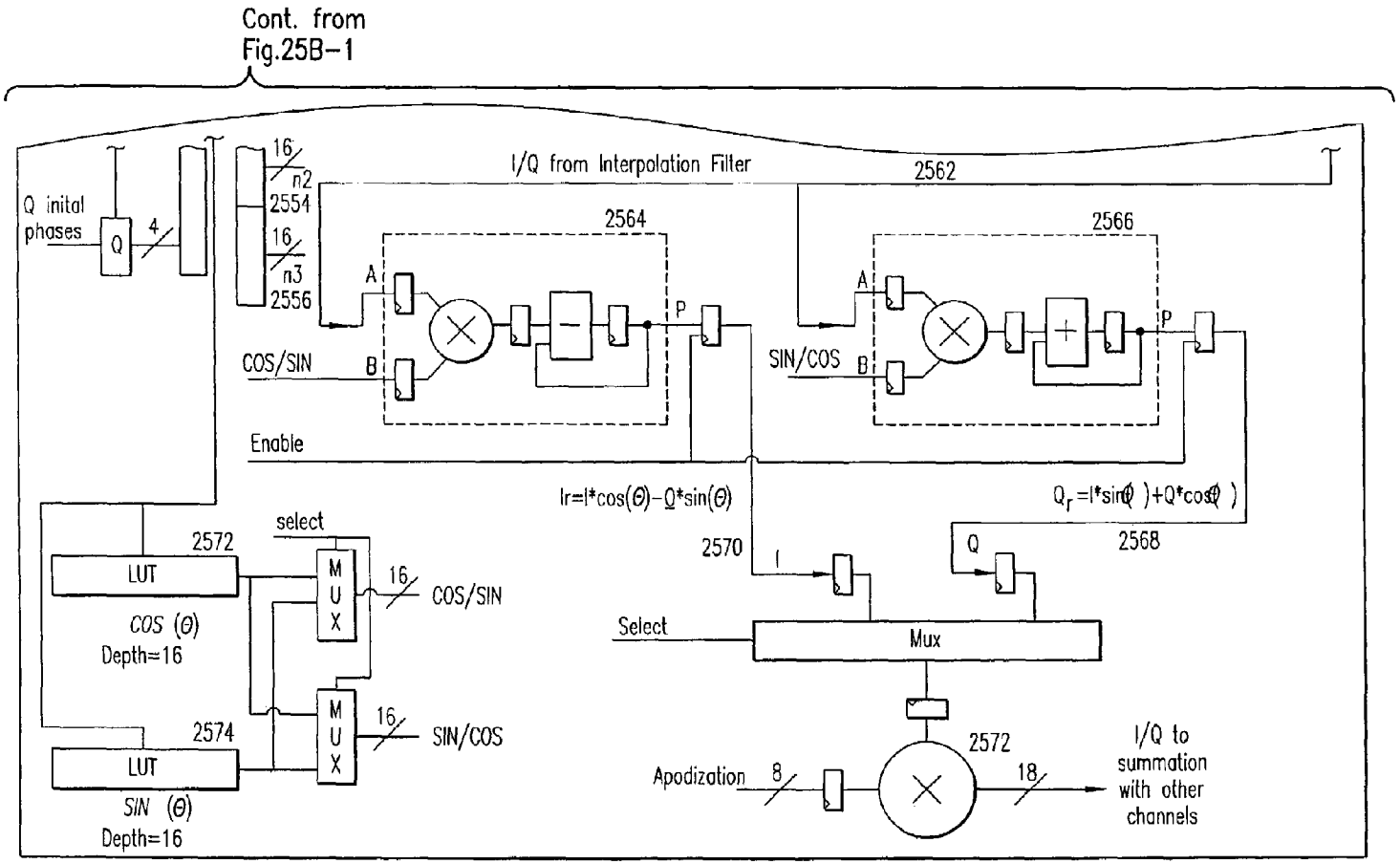

Another way to implement the interpolation filters, phase rotation and dynamic apodization is shown in FIG. 25B. In this figure, all digital circuit elements in the upper box 2520 which require a clock are clocked at the receive frequency clock. All digital circuit elements in the lower box 2522 which require a clock are clocked at twice the receive frequency clock. The input I/Q data from the analogue to digital converters (ADCs) 2524, 2526 are written to separate FIFOs 2528, 2530. The samples output from the ADCs 2524, 2526 may undergo an offset correction in which a predetermined constant value is added. The samples from the output of the ADC offset correction stage 2524, 2526 are stored simultaneously into the FIFOs 2528, 2530, so the writing of the new sample into the FIFOs does not require separate timing logic. All the channels share the same write enable signals. The read side of the FIFO of each I and Q channel 2528, 2530 uses independent read enable signals 2532, 2534, controlled by receive delay signals generated by the Beamformer Controller.

The start of the read enable signals 2532, 2534 of each FIFO is delayed by a number of receive clock cycles equal to the initial coarse delay value 2536 required for each channel. If the read enable signal 2532, 2534 is held low while data is written into the FIFO 2528, 2530, the read out of the FIFO will be suspended and the coarse delay 2536 will increase. When the read enable signal 2532, 2534 goes high, the coarse delay 2536 that is applied remains constant. To align echoes in the signals from the center and the outer edge of the aperture, the center signals will be delayed a period of time before they can be summed with the signals from the outer edge. The delay value for sampled data at the center of the aperture is greater than that of the outer edges.

Dynamic receive focusing requires a control signal DF 2538 which goes high when the interpolation filter index 2540 needs to be changed. The interpolation filter index 2540 is a modulo 16 number ranging from 0 to 15. The interpolation filter index 2540 will decrease when the interpolation point has shifted by 1/16 wavelength. When the interpolation filter index 2540 decreases from 0 to 15, the FIFO read enable signal 2532, 2534 will go low for one clock cycle, to increase the coarse delay 2536 by one.

The fine delay is implemented by interpolation. In this example, the interpolation filters are implemented as systolic FIR filters with 4 taps 2542, 2544, 2546, 2548. There are 16 sets of coefficients for the 16 interpolation points. Each interpolation point has 4 coefficients 2550, 2552, 2554, 2556. By interleaving the I and Q samples and operating the filter at twice the receive clock frequency, the same interpolation filter can be used for both the I and Q samples. Different sets of coefficients are used for the I and Q interpolation, since the I and Q samples acquired by the ADCs are sampled at different points in time but are interpolated to the same point in time. To correct the sampling offset, the interpolation filter index for the Q samples will be offset from that of the I samples by 4. The coefficients used in the interpolation filter can alternate between I coefficients and Q coefficients by switching the address of the RAM 2558 which stores the coefficients. The interpolation filter indices are represented by the address counters 2560 for the coefficients. The address counters 2560 for the I and Q coefficients decrease by one when the DF signal 2538 goes high for one clock cycle. The output of the interpolation filter 2560 is I/Q interleaved.

The interpolated signals are fed to the phase rotation stage 2564, 2566 shown in FIG. 25B. There are two multiplier/accumulate elements in the phase rotation circuit. One is used to generate Qr=I*sin(angle)+Q*cos(angle) 2568 and the other to generate Ir=I*cos(angle)−Q*sin(angle) 2570. Sine and cosine coefficients are stored in RAMs as look-up-tables 2572, 2574. There are 16 sets of sine and cosine values. The addresses of the cosine and sine look up tables (LUT) 2572, 2574 are updated at the same time as the interpolation filter coefficients 2550, 2552, 2554, 2556. The phase rotation circuit 2564, 2566 also operates at twice the center frequency. Every second operating cycle produces a pair of valid Ir and Qr data.

For dynamic apodization, the outputs of the phase rotation 2568, 2570 are multiplied by a factor which is dynamically changed during receive. Also if the multiplication factor in a channel is set to zero, the channel does not contribute to the aperture. This way, dynamic aperture updating is achieved. I and Q samples are interleaved through a multiplexer (MUX) 2572 to a common multiplier, which reduces the multiplier resources required.

Multi-Line Beamforming with Interpolation Filters

Figure 38:
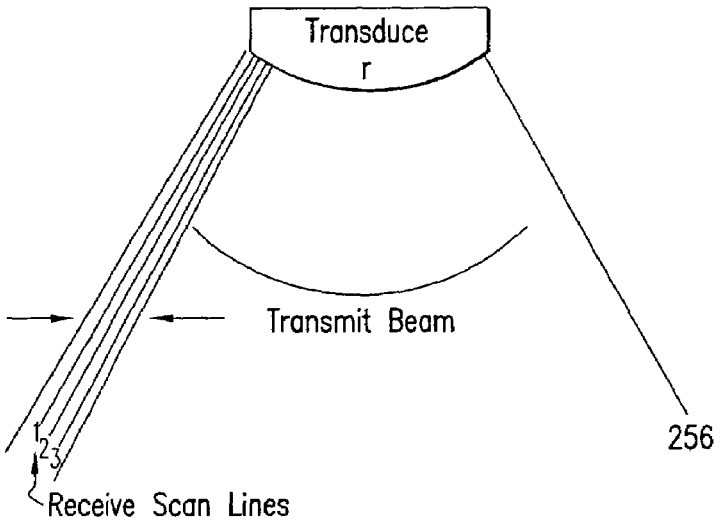
FIG. 38 displays 3-1 multi-line scanning with an exemplary curved array transducer.

The use of interpolation filters for beamforming allows multi-line scanning. In multi-line scanning, several receive lines are reconstructed in the same transmit beam, as shown in FIG. 38. The transmit beam is typically broadened with a large depth of field to cover the region where the receive lines will be acquired.

Since the adjacent receive scan lines in a multi-line scan have only small changes in the individual delays for each channel, the interpolation filter delay implementation allows all lines to be processed concurrently. This method works with bandwidth sampling, where the interpolation filters can be operated at a rate higher than the sample rate, as is shown in the exemplary conceptual implementation of the interpolation filter method for an individual channel in FIG. 39.

Figure 39:
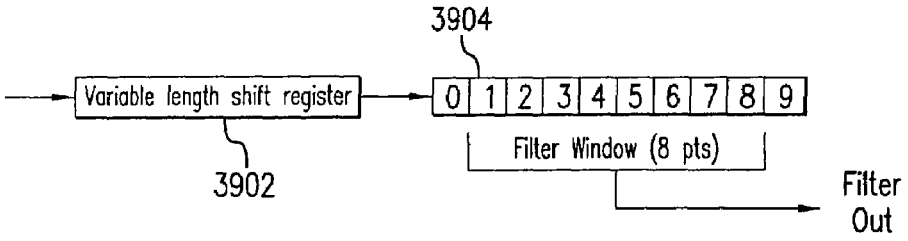
FIG. 39 displays a conceptual implementation of an interpolation delay method.

In FIG. 39, the digital samples from an individual receive channel's A/D converter are sent through a variable length shift register 3902 to implement a coarse delay of an integer number of samples. The output of the variable length shift register 3902 is then sent to a second shift register 3904, where the individual shift stages can be accessed. When this second shift register 3904 is filled, the interpolation filter can operate on a subset of samples, which for the example shown is eight samples. The interpolation filter provides the fine delay for 1/16 wavelength or better resolution. In the example above, the interpolation filter provides an interpolated sample between cells 4 and 5 of the filter shift register.

Figure 40:
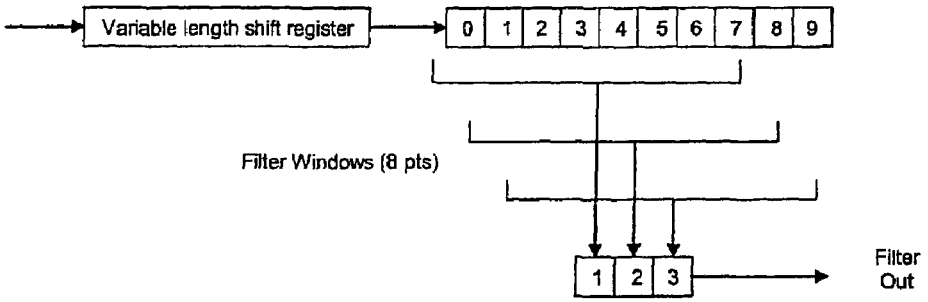
FIG. 40 displays an exemplary 3-1 multi-line operation of an interpolation delay method.

For 3-1 multi-line scanning, as shown in FIG. 40, the interpolation filter is operated three times for every sample shift. In the example of FIG. 40, the filter window is offset from the nominal position by one sample backwards for the first receive line, and one sample forward for the third receive line. In reality, there may be less than a sample difference in the delay values for the adjacent lines, requiring that all lines use the same filter window. The position of the filter windows for each line is programmable. In situations where the delay differences are greater than one sample, the filter shift register can be expanded to allow greater separations between windows. For bandwidth sampling, where there are only one or two samples per wavelength, the filter windows would often not need to be separated by more than one sample period.

The output of the filter operations, as shown in FIG. 40, is time multiplexed into a single output stream. This stream is summed with the contributions from other channels to produce the beamformer output. Note that for 3-1 multi-line the summation circuitry is capable of operating at three times the sample rate. The summation output of the beamformer can then be de-multiplexed to generate the three multi-line receive lines for downstream processing. The downstream processing is capable of processing three lines in the acquisition time of a single ray line.

In the exemplary receive beamforming methods described above, the output is a digital data stream of samples representing the sampled RF data along a reconstruction line. This stream is derived by summing the data samples from all receive channels that participate in the receive active aperture. The RF data stream can be captured in a buffer with sufficient storage to hold an entire ray line. This same buffer can be used for synthetic aperture acquisitions, and can be summed with the RF data from the second half of the receive aperture as it exits from the summation circuitry.

For Nyquist or bandwidth sampling schemes with no down-conversion, the summed RF data stream exits the beamformer as a raw RF stream. This data stream can be converted to a different format using a pair of complimentary 90 degree phase difference filters, often referred to as Hilbert transform filters. These filters effectively band-pass the RF signal and down-convert it at the same time to baseband quadrature data streams. These baseband I and Q data streams can then be combined to provide echo amplitude data for 2D imaging, or processed further for Doppler blood flow detection. The Hilbert transform filters can also be used to selectively filter and process a portion of the received signal spectrum, as is needed for harmonic imaging, or frequency compounding. In the case of frequency compounding, the filters can be time multiplexed to produce interleaved output samples from different frequency bands of the spectrum.

Referring back again to FIG. 31, the beamformer module 3102 can also comprise a beamformer control. To orchestrate the events to form a complete image frame, the beamformer uses some sort of controller. The controller can be implemented as a simple state machine, which specifies a series of beamformer events. Each beamformer event can specify a transmit action, a receive action, and/or a signal processing action. Transmit actions specify all the parameters associated with transmitting pulses from the array. These include the duration of connection of the pulsers to the desired elements in the array, the delay times of each pulser, the transmit waveform characteristics, and the transmit aperture apodization function. Receive actions specify all parameters associated with receiving and beamforming the returning echoes. These include specification of the elements connected to the receive channels, the TGC waveform to be used for each channel, the A/D converter sample rates, and the dynamic aperture, steering and/or dynamic focus patterns to be used in the reconstruction process. Finally, the signal processing actions specify what to do with the summation output, such as buffering it for synthetic aperture or sending it to the Hilbert transform filters. The Hilbert transform filters are specified to perform whatever action is needed for the beamformer event.

As is apparent from the above description, the control of the beamforming process can be complex, and a method of handling this complexity is to encode all the information prior to real-time scanning in memory blocks used to control the hardware. The beamformer controller's task is then reduced to 'pointing' to the appropriate portion of the memory block to retrieve the information needed for a beamformer event. Setting up the beamformer for a specific mode of operation is then accomplished by loading all the memory blocks with parameter information, then programming the various beamformer events with their respective pointers into the controller's state machine. To perform the scanning mode, the controller is then told to run, and steps through the events for an entire frame of acquisition data. At the end of the frame, the controller looks for a stop signal, and if none is found, repeats the whole sequence again.

Embodiments of the exemplary ultrasound system are capable of very high acquisition frame rates in some modes of operation, in the range of several hundred frames per second or higher. Just as with other embodiments according to the present invention, exemplary embodiments process displayed ultrasound image information at 30 fps or lower, even if the acquisition rates are much higher through the use of asynchronous processing as described in reference to FIG. 28. It is to be appreciated, however, that for Nyquist sampled data, the storage is increased by 50-100%.

Also as previously described, the signal processing hardware/software has random access to the RF memory buffer, and accesses the RF data from a single acquisition frame to produce the displayed estimate data. In this exemplary embodiment, the maximum frame rate for signal processing and display is 30 fps, which is typically set by a timer, which signals the signal processing task every $1/30^{th}$ of a second. When processing of a new display frame is complete, the signal processing/display task waits for the next 1/30 of a second time tick. At that time, the signal processing task reads the 'Last Frame' pointer from the Write Controller to see if a new frame is available. If the 'Last Frame' pointer has not advanced from the previously processed frame, signal processing does nothing, and waits for the next 1/30 of a second tick. If the 'Last Frame' pointer has changed, signal processing begins on the frame indicated by the pointer. In this manner, signal processing always starts on a 1/30 second tick, and always works on the most recent frame acquired. If acquisition is running much faster than 30 fps, then the 'Last Frame' pointer will advance several frames with each signal processing action.

After the system has been put in freeze, the RF frames stored in the memory buffer can be processed at any desired rate, up to the original acquisition rate. One simply calculates how many RF frames to advance in $1/30^{th}$ of a second, which is computed as a floating point value that can vary from a fraction less than one to as many frames as occurred in $1/30^{th}$ of a second during real time acquisition. With each $1/30^{th}$ of second tick, signal processing accumulates the frame advance value, until an integer boundary, is crossed. At that time, signal processing processes the frame which is that integer boundary number of frames ahead of the last frame it processed.

Synthetic aperture beamforming is also supported by this memory buffer scheme. In this case, the various lines which make up the synthetic aperture are acquired into the memory buffer sequentially, so that the size of an RF storage frame increases. This is simply a different parameter for the Write Controller, which keeps track of how many lines are written per acquisition frame. For readout, signal processing then combines the multiple RF lines in a synthetic aperture to produce the final result.

The RF data for cineloop playback also provides for reprocessing the data in different ways, bringing out new information. For example, the wall filters for color flow imaging can be changed during playback, allowing optimization for the specific flow conditions. Second, for the researcher who wants to work with RF data, the buffer memory can dumped to an external storage device, providing multiple frames of RF data to analysis. Finally, as a diagnostic tool, the buffer memory can be loaded with test RF data from the CPU, allowing debug, analysis and verification of the signal processing methods.

Figure 41:
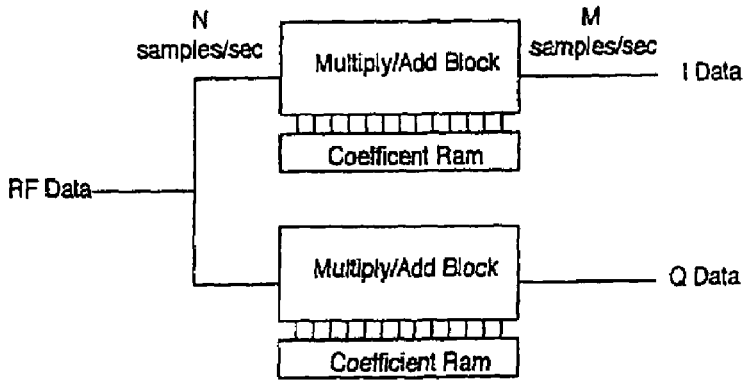
FIG. 41 is a schematic design of Complimentary Hilbert Transform Filters.

For the Nyquist sampled beamforming method, down-converted quadrature sampled data is derived from the RF data for amplitude detection and Doppler processing. This can be obtained with complimentary phase FIR filters that are designed to have a 90 degree phase difference over the frequencies in the pass band. These filters can also down-convert the sample stream to a lower sample rate, provided the output sample rate is still sufficient to sample the range of frequencies in the signal. To provide down-converted output samples, the filters operate on RF data that is shifted by an integral number of cycles of the center frequency of the spectrum. Alternately, different filters can be designed for non-integer number of cycle shifts to obtain smaller decimation ratios. A schematic design of an exemplary Hilbert filter, as are known in the art by one of ordinary skill, is shown in FIG. 41.

The filters are designed by first computing a low pass filter designed using a windowing method. The filter length should be around 40 taps to insure a good response over a broad range of frequencies, and should be a multiple of the number of samples in the period of the center frequency of the RF data. For example, if the sample rate is 120 MHz and the center frequency is 30 MHz, there are 4 samples in the period of the center frequency and an appropriate filter length would be 40 taps (10 periods). The low pass coefficients are then multiplied by a sine and cosine function, whose frequency matches the center frequency. In the 30 MHz example, each period of the sine and cosine function has 4 samples.

To obtain down-converted samples, the filters are applied on samples that are shifted by an integral number of cycles of the center frequency. In the 30 MHz center frequency case (sampled at 120 MHz), the RF samples are shifted by 4 samples at a time, leading to a decimation ratio of 4 to 1. With this decimation ratio, the input signal is restricted to 100% bandwidth, otherwise, aliasing of the output samples will result.

To obtain smaller decimation ratios, the filters can use alternate coefficient sets to preserve the phase information. In the 30 MHz example, to achieve a decimation ration of 4 to 2, two sets of coefficients are used—one for 0 degrees phase, and another for 180 degrees phase.

These alternate coefficient sets are obtained by sampling the sine and cosine at the appropriate phase increments before multiplying with the low pass filter coefficients. In this case where the shift between output samplers is ½ the period of the center frequency, a simple method to provide the decimation rate is to leave the coefficients the same, and invert the sign of the filter output for the ½ period increments.

The pass band characteristics of the filters can be modified using different windowing functions. This may be desirable in applications such as harmonic imaging or tracking filters. Frequency compound can be achieved without additional filters for high decimation ratios, provided that the filters can operate at the input sample rate. For the 30 MHz example, two filters can be used with different center frequencies that operate on RF data at two sample shift increments. The filter block output a different filter result every two samples. The two interleaved I,Q samples from the different filters are then detected and summed together to produce a 4 to 1 decimated detected output.

Example 3

An embodiment of the exemplary system interface to an array with up to 256 elements may be used to obtain ultrasound images. Table 4 shows exemplary depth range, field of view, frame rate in B-Mode and frame rate in color flow imaging (CFI) for acquiring images. These operating parameters can be used for the particular small animal imaging application described in the far left column. As would be clear to one skilled in the art, however, other combinations of operating parameters can be used to image other anatomic structures or portions thereof, of both small animal and human subjects.

A small animal subject is used and the animal is anesthetized and placed on a heated small animal platform. ECG electrodes are positioned on the animal to record the ECG waveform. A temperature probe is positioned on the animal to record temperature. The important physiological parameters of the animal are thereby monitored during imaging. The anesthetic used may be a for example isoflourane gas or another suitable anesthetic. The region to be imaged is shaved to remove fur. Prior to imaging, an ultrasound conducting gel is placed over the region to be imaged. The ultrasound array is placed in contact with the gel, such that the scan plane of the array is aligned with the region of interest. Imaging can be conducted "free hand" or by mounting the array onto a fixture to hold it steady.

B-Mode frame rates are estimated for the different fields of view indicated in Table 4. Higher frame rates are achievable with reduced field of view. Color flow imaging (CFI)

frame rates are estimated for the indicated color box widths, with line density one-half that of B-mode, and with the B-mode image acquired concurrently.

TABLE 4

Exemplary Depth Range, Field Of View, Frame Rate In B-Mode And Frame Rate In Color Flow Imaging (CFI) For Acquiring Images

| | Depth range | B-Mode Field of View | Color Box width | Frame Rate-B-mode | Frame Rate CFI |
|---|---|---|---|---|---|
| Mouse cardiology 30 MHz center frequency | 3-10 mm | 12 mm | 8 | At least 180 fps | At least 60 fps |
| Mouse abdominal 30 MHz | 2-12 mm | 19.2 mm | 12.8 | At least 100 fps | At least 30 fps |
| Mouse, shallow regions, Peripheral Vascular 40-50 MHz | 1-6 mm | 12.8 mm | 8 | At least 190 fps | At least 80 fps |
| Rat cardiology 20 MHz center frequency | 5-20 mm | 24 mm | 20 | At least 70 fps | At least 25 fps |

Unaliased velocities measurable with a 150 KHz PRF, for various center frequencies and angles are shown in Table 5 for Pulsed Wave (PW) Doppler.

TABLE 5

Unaliased Velocities Measurable With 150 KHz PRF, for Various Center Frequencies and Angles

| Center frequency | Maximum Unaliased Velocity, 0° angle | Maximum Unaliased Velocity, 30° angle | Maximum Unaliased Velocity, 60° angle |
|---|---|---|---|
| 20 MHz | 2.89 m/s | 3.34 m/s | 5.77 m/s |
| 30 MHz | 1.93 m/s | 2.22 m/s | 3.85 m/s |
| 40 MHz | 1.44 m/s | 1.66 m/s | 2.89 m/s |
| 50 MHz | 1.16 m/s | 1.33 m/s | 2.31 m/s |

A mouse heart rate may be as high as 500 beats per minute, or about 8 beats per second. As the number of frames acquired per cardiac cycle increases, the motion of the heart throughout the cardiac cycle can be more accurately assessed. The frame rate should be at least 10 frames per cardiac cycle, and preferably 20 for better temporal resolution. Therefore, in one embodiment frames are acquired at a rate of at least 160 frames per second, with a field of view large enough to include a long axis view of the mouse heart and surrounding tissue (10-12 mm). For example, using a 30 MHz linear array, the frame rate for a 12 mm field of view is about 180 frames per second. For smaller fields of view, the frame rates used are higher; (e.g., for a 2 mm field of view, with the 30 MHz linear array frame rates of over 900 frames per second can be used for viewing rapidly moving structures such as a heart valve).

The maximum velocities present in the mouse circulatory system (in the aorta) may be as high as 1 m/s in normal adult mice, but in pathological cases can be as high as 4-5 m/s. To acquire and display unaliased PW Doppler signals from the mouse aorta, the Pulse Repetition Frequency (PRF) for PW Doppler must be relatively high. In the exemplary system, PW Doppler mode PRFs as high as 150 KHz are used, which for a center frequency of 30 MHz and a Doppler angle of 60°, allows for unaliased measurement of blood velocities of 3.8 m/s.

The frame rate for B-Mode Imaging is determined by the two-way transit time of ultrasound to the maximum depth in tissue from which signals are detected, the number of lines per frame, the number of transmit focal zones, the number of lines processed for each transmit pulse and the overhead processing time between lines and frames. Images obtained with different transmit focal zone locations can be "stitched" together for improved resolution throughout the image at the expense of frame rate, which will decrease by a factor equal to the number of zones. Selection of lower or higher transmit center frequencies for increased penetration, or increased resolution, either user selectable or automatically linked to transmit focal zone location. Multi-line processing, which involves the parallel processing of ultrasound lines, can be used to increase frame rate.

PW Doppler features include a PRF range from about 500 Hz to about 150 KHz, alternate transmit frequency selection, the selection of range gate size and position, the selection of high-pass filter cut-off, and duplex mode operation in which a real-time B-Mode image is displayed simultaneously with the PW Doppler mode may be the same as the transmit frequency used in B-Mode, or it may be different. The ability to steer the PW Doppler beam is dependent on the frequency and pitch of the array used, and the directivity of the elements in the array, as would be appreciated by one skilled in the art. For an array with a pitch of 75 microns and operating in PW Doppler mode at a transmit frequency of 24 MHz, the beam may be steered up to approximately 20°. For this array, larger steering angles would result in unacceptably large grating lobes, which would contribute to the detection of artifactual signals.

Color flow imaging (CFI) can be used to provide estimates of the mean velocity of flow within a region of tissue. The region over which the CFI data is processed is called a "color box." B-Mode data is usually acquired nearly simultaneously with the Color Flow data, by interleaving the B-Mode lines with Color Flow lines. The Color Flow data can be displayed as an overlay on the B-Mode frame such that the two data sets are aligned spatially. CFI includes a PRF range from about 500 Hz to about 25 to 75 KHz, depending on the type of array. With 40 MHz center frequency and 0° angle between ultrasound beam axis and velocity vector, maximum unaliased velocity will be about 0.72 m/s. Beam steering can depend on the characteristics of the array, (specifically the element spacing), the transmit frequency, and the capabilities of the beamformer; e.g., steering may not be available at the primary center frequency, but may be available at an alternate (lower) frequency. For an array with a pitch of 75 microns and operating in CFI mode at a transmit frequency of 24 MHz, the beam can be steered up to approximately 20°. Larger steering angles would result in unacceptable grating lobe levels. Color flow imaging features can include the selection of the color box size and position, transmit focal depth selection, alternate frequency selection, range gate size selection, and selection of high pass filter cut-off. Power Doppler is a variation of CFI which can be used to provide estimates of the power of the Doppler signal arising from the tissue within the color box. Tissue Doppler mode is a variation of CFI in which mean velocity estimates from moving tissue are provided. Multi-line processing is a method which may be applied to the CFI modes, in which more than one line of receive data is processed for each transmit pulse transmitted.

The beamformer may be capable of supporting modes in which 2-D imaging and Doppler modes are active nearly simultaneously, by interleaving the B-Mode lines with the Doppler lines. 3-D imaging, as known to one of ordinary skill in the art, utilizes mechanical scanning in elevation direction.

Throughout this application, various publications are referenced. The disclosures of these publications in their entireties are hereby incorporated by reference into this application in order to more fully describe the state of the art to which this invention pertains.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ultrasound imaging system, comprising:

an arrayed ultrasonic transducer having a plurality of elements [for transmitting] *configured to transmit* into a subject a transmitted ultrasound signal at a transmit center frequency of [up to 55] *15* megahertz (MHz) *or greater*; *and* a signal processing unit operatively connected with said arrayed ultrasonic transducer and comprising:

a digital transmit beamformer subsystem comprising one or more field programmable gate arrays (FPGA), each having an FPGA clock frequency (FPGA fc), said digital transmit beamformer subsystem having a delay resolution time of [at least [1/(2×FPGA fc)] or greater] (*1/(2×FPGA fc)*) *or less*, a receive beamformer subsystem, a front end electronics module, a beamformer control module, a signal processing module, a parallel to serial converter, and a computer unit;

wherein said signal processing unit is configured to acquire a received ultrasound signal having a frequency of at least 15 MHz from said arrayed ultrasound transducer, and wherein said digital transmit beamformer subsystem is configured to transmit an ultrasound signal having said transmit center frequency by encoding a fine delay and half-cycle sections of said transmitted ultrasound signal into bit words that are converted to a serial bit stream by said parallel to serial converter, wherein said transmitted ultrasound signal comprises a positive transmit pulse having a positive pulse width and a negative transmit pulse having a negative pulse width, and said positive pulse width and said negative pulse width are independently adjustable.

2. The ultrasound imaging system of claim 1, wherein said bit words are up to 16 bit words.

3. The ultrasound imaging system of claim 1, wherein said transmitted ultrasound signal further comprises (i) a plurality of positive half-wave cycle sections, each comprising at least one said positive transmit pulse and (ii) a plurality of negative half-wave cycle sections, each comprising at least one said negative transmit pulse.

4. The ultrasound imaging system of claim 1, wherein said transmitted ultrasound signal comprises an adjustable number of cycles transmitted.

5. The ultrasound imaging system of claim 1, wherein said front end electronics module is constructed as a replaceable plug-in module.

6. The ultrasound imaging system of claim 1, wherein said arrayed ultrasonic transducer is selected from the group consisting of a linear array transducer, a phased array transducer, a two-dimensional (2-D) array transducer, and a curved array transducer.

7. The ultrasound imaging system of claim 1, wherein said transmitted ultrasound signal has a transmit center frequency of 15 MHz up to 55 MHz.

8. The ultrasound imaging system of claim 1, wherein said signal processing module utilizes quadrature sampling and has a receive sampling frequency, wherein said signal processing unit is configured so that said receive sampling frequency may be selectively chosen.

9. The ultrasound imaging system of claim 1, wherein said arrayed ultrasonic transducer has a field of view of at least 5.0 millimeters (mm);

and wherein said signal processing unit is [adapted for acquiring] *configured to acquire* a received ultrasound signal from said arrayed ultrasound transducer at [a] *an acquisition* frame rate of at least 20 frames per second (fps).

10. The system of claim 1, wherein:

[said] *the* arrayed ultrasound transducer is [capable of generating and transmitting] *configured to generate and transmit* into a subject ultrasound at a frequency of up to at least [55 megahertz (MHz)] *80 MHz* and at a pulse repetition frequency (PRF) of at least 500 hertz (Hz), [and]

*the arrayed ultrasound transducer* is [capable of receiving] *futher configured to receive* ultrasound from the subject, the arrayed ultrasound transducer has a field of view of at least 5.0 millimeters (mm)[;], *and*

[wherein said] *the* system further comprises a processing unit [for generating] *configured to generate* a color flow Doppler or pulsed wave Doppler ultrasound image from the received ultrasound.

11. The ultrasound imaging system of claim 1, wherein said FPGA fc is the highest operable frequency of the one or more [FPGA] *FPGAs*.

12. The ultrasound imaging system of claim 1, wherein said transmit center frequency is adjustable.

13. The ultrasound imaging system of claim 3, wherein each fine delay of said at least one said positive transmit pulse within each positive half wave cycle is adjustable, and each fine delay of said at least one said negative transmit pulse within each negative half wave cycle is adjustable.

14. A signal processing unit for an arrayed ultrasound imaging system, *the signal processing unit* comprising:

a digital transmit beamformer subsystem configured to operate [up to 55 MHz] *at a* transmit center frequency *of 15 Megahertz (MHz) or greater*, wherein said digital transmit beamformer subsystem further comprises one or more field programmable gate arrays (FPGA), each having an FPGA clock frequency (FPGA fc), said digital transmit beamformer subsystem having a delay resolution time of [at least [1/(2×FPGA fc)] or greater] *(1/(2×FPGA fc)) or less*;

a digital receive beamformer subsystem;

a front end electronics module;

a beamformer control module;

a signal processing module;

a parallel to serial converter; and a computer unit, wherein said signal processing unit is configured to acquire a received ultrasound signal from an arrayed ultrasound transducer having a plurality of elements, and wherein said digital transmit beamformer subsystem is configured to transmit an ultrasound signal having said transmit center frequency by encoding a fine delay and half-cycle sections of said transmitted ultrasound signal into bit words that are converted to a serial bit stream by said parallel to serial converter, wherein said transmitted ultrasound signal comprises a positive transmit pulse having a positive pulse width and a negative transmit pulse having a negative pulse width, and said positive pulse width and said negative pulse width are independently adjustable.

15. The signal processing unit of claim 14, wherein said bit words are up to 16 bit words.

16. The signal processing unit of claim 14, wherein said transmitted ultrasound signal comprises an adjustable number of cycles transmitted.

17. The signal processing unit of claim 14, wherein said front end electronics module is constructed as a replaceable plug-in module.

18. The signal processing unit of claim 14, wherein said arrayed ultrasonic transducer is selected from the group consisting of a linear array transducer, a phased array transducer, a two-dimensional (2-D) array transducer, and a curved array transducer.

19. The signal processing unit of claim 14, wherein said transmit center frequency is 15 MHz up to 55 MHz.

20. The signal processing unit of claim 14, wherein said FPGA fc is the highest operable frequency of the one or more FPGA.

21. The signal processing unit of claim 14, wherein said transmit center frequency is adjustable.

22. A digital transmit beamformer for an arrayed ultrasound imaging system, *the digital transmit beamformer* comprising:

one or more FPGAs, each having an FPGA clock frequency (FPGA fc); and a parallel to serial converter, wherein said digital transmit beamformer is configured to transmit an ultrasound signal having a transmit center frequency [up to 55] *of 15* MHz *or greater* with a delay resolution time of [at least [1/(2×FPGA fc)] or greater] *(1/(2×FPGA fc)) or less* by encoding a fine delay and half-cycle sections of said transmitted ultrasound signal into bit words that are converted to a serial bit stream by said parallel to serial converter, wherein said transmitted ultrasound signal comprises a positive transmit pulse width and a negative transmit pulse width, and said transmit pulse width and said negative transmit pulse width are independently adjustable.

23. The digital transmit beamformer of claim 22, wherein said transmitted ultrasound signal comprises an adjustable number of cycles transmitted.

24. The digital transmit beamformer of claim 22, wherein said digital transmit beamformer is configured to be operatively connected with an arrayed ultrasonic transducer and said arrayed ultrasonic transducer is selected from the group consisting of a linear array transducer, a phased array transducer, a two-dimensional (2-D) array transducer, and a curved array transducer.

25. The digital transmit beamformer of claim 22, wherein said transmit center frequency is 15 MHz up to 55 MHz.

26. The digital transmit beamformer of claim 22, wherein said bit words are up to 16 bit words.

27. The digital transmit beamformer of claim 22, wherein said FPGA fc is the highest operable frequency of the one or more FPGA.

28. The digital transmit beamformer of claim 22, wherein said transmit center frequency is adjustable.

29. The ultrasound imaging system of claim 8, wherein said receive sampling frequency is chosen at a frequency different from said transmit center frequency.

30. The ultrasound imaging system of claim 8, wherein said receive sampling frequency is chosen at a frequency the same as said transmit center frequency.

31. The ultrasound imaging system of claim 8, wherein said digital transmit beamformer subsystem further comprises a transmit focal [dept] *depth* such that said receive sampling frequency is dependent upon said transmit focal depth.

32. The ultrasound imaging system of claim 30, wherein said receive sampling frequency decreases as said transmit focal depth increases.

33. The system of claim 9, wherein the signal processing unit *is* further [produces] *configured to produce* an ultrasound image from the received ultrasound signal.

34. The system of claim 9, wherein the arrayed ultrasonic transducer has a center operating frequency of at least 15 MHz and the arrayed ultrasonic transducer has an element pitch equal to or less than 2.0 times the wavelength of sound at the arrayed ultrasonic transducer's transmit center frequency.

35. The system of claim 9, wherein the arrayed ultrasonic transducer has an element pitch equal to or less than 1.5 times the wavelength of sound at the arrayed ultrasonic transducer's transmit center frequency.

36. The system of claim 9, wherein the front end electronics module further comprises a transmit circuit and a receive channel, wherein the transmit circuit comprises a transmit supply voltage connected through two field-effect transistors (FETs) to a transformer with a center-tapped winding in which the arrayed ultrasonic transducer is operatively connected to a first end of a secondary winding of the transformer and an input to the receive channel is connected to a second end of the secondary winding of the transformer such that said transmit supply voltage is set to substantially zero and said two FETs are turned on when said receive channel is receiving a signal and said transformer generates a transmit signal and couples the transmit signal to the arrayed ultrasonic transducer when said transmit circuit is transmitting a signal.

37. The system of claim 9, wherein each element of said arrayed ultrasonic transducer having a plurality of elements is operatively connected to a receive channel.

38. The system of claim 9, wherein at least two lines of ultrasound are generated, transmitted into the subject and received from the subject at each element of the array for each frame of the generated ultrasound image.

39. The system of claim 9, wherein one line of ultrasound is generated, transmitted into the subject and received from the subject at each element of the array for each frame of the generated ultrasound image.

40. The system of claim 9, wherein the elements of the arrayed ultrasonic transducer having a plurality of elements are separated by a distance equal to the wavelength of the [center] transmit *center* frequency of the *arrayed ultrasonic* transducer.

41. The system of claim 9, wherein a length of the arrayed ultrasonic transducer having a plurality of elements is equal to [a] *the* field of view of the *arrayed ultrasound* transducer.

42. The system of claim 9, wherein the [received ultrasound signal is acquired at a] *acquisition* frame rate [of] *is* at least 200 fps.

43. The system of claim 9, wherein the [received ultrasound signal is acquired at a] *acquisiton* frame rate *is* within the range of about 100 fps to about 200 fps.

44. The system of claim 9, wherein the ultrasound image has a lateral resolution of about 150 microns (μm) or less.

45. The system of claim 9, wherein the *signal processing unit is further configured to focus the* transmitted ultrasound signal [can be focused] at a depth of about 1.0 mm to about 30.0 mm.

46. The system of claim 33, wherein the received ultrasound signal is processed by said signal processing unit to generate the ultrasound image at a display rate that is [slower] *lower* than the acquisition *frame* rate.

47. The system of claim 33, wherein the ultrasound image is produced by said signal processing unit in an ultrasound mode selected from the group consisting of B-mode, M-mode, Doppler mode, RF-mode, and 3-D mode.

48. The system of claim 46, wherein the display rate of the generated ultrasound image is 100 fps or less.

49. The system of claim 48, wherein the display rate of the generated ultrasound image is 30 fps or less.

50. The system of claim 36, wherein the front end electronics module further comprises two or more signal samplers for each receive channel.

51. The system of claim 50, wherein the signal samplers are analog to digital converters.

52. The system of claim 50, wherein the signal samplers *are configured to* use quadrature sampling to sample a received signal.

53. The system of claim 52, wherein the signal samplers comprise sampling clocks shifted 90 degrees out of phase.

54. The system of claim 53, wherein the sampling clocks have a receive clock period approximately equal to the center frequency of a received ultrasound signal.

55. The system of claim 54, wherein a delay resolution of less than the receive clock period is used to process the [acquired] *received ultrasound* signal.

56. The system of claim 55, wherein the delay resolution is 1/16 of the receive clock period.

57. The system of claim 37, wherein the number of elements of said arrayed ultrasonic transducer having a plurality of elements is greater than the number of receive channels.

58. The system of claim 37, wherein the arrayed ultrasonic transducer having a plurality of elements comprises at least 64 elements that are operatively connected to at least 32 receive channels.

59. The system of claim 37, wherein the arrayed ultrasonic transducer having a plurality of elements comprises 256 elements that are operatively connected to 64 receive channels.

60. The system of claim 37, wherein the arrayed ultrasonic transducer having a plurality of elements comprises 256 elements that are operatively connected to 128 receive channels.

61. The system of claim 37, wherein the arrayed ultrasonic transducer having a plurality of elements comprises 256 elements that are operatively connected to 256 receive channels.

62. The system of claim 37, wherein the arrayed ultrasonic transducer having a plurality of elements comprises 256 elements.

63. The system of claim 62, wherein 512 lines of ultrasound are generated, transmitted into the subject and received from the subject for each frame of the generated ultrasound image.

64. The system of claim 62, wherein 256 lines of ultrasound are generated, transmitted into the subject and received from the subject for each frame of the generated ultrasound image.

65. The system of claim 39, wherein the [received ultrasound signals are acquired at an] acquisition *frame* rate [of] *is* at least 200 [frames per second (fps)] *fps*.

66. The system of claim 40, wherein the [center] transmit *center* frequency is selected from the group consisting of 15 MHz, 20 MHz, 30 MHz, 40 MHz, 50 MHz, and 55 MHz.

67. The system of claim 44, wherein the ultrasound image has [a] *an* axial resolution of about 75 microns (μm) or less.

68. The system of claim 67, wherein the ultrasound image has a spatial resolution of about 30 microns (μm) or less.

69. The system of claim 45, wherein the *signal processing unit is further configured to focus the* transmitted ultrasound signal [can be focused] at a depth of about 3.0 mm to about 10.0 mm.

70. The system of claim 45, wherein the *signal processing unit is further configured to focus the* transmitted ultrasound signal [can be focused] at a depth of about 2.0 mm to about 12.0 mm.

71. The system of claim 45, wherein the *signal processing unit is further configured to focus the* transmitted ultrasound signal [can be focused] at a depth of about 1.0 mm to about 6.0 mm.

72. The system of claim 45, wherein the *signal processing unit is further configured to focus the* transmitted ultrasound signal [can be focused] at a depth of about 3.0 mm to about 8.0 mm.

73. The system of claim 45, wherein the *signal processing unit is further configured to focus the* transmitted ultrasound signal [can be focused] at a depth of about 5.0 mm to about 18.0 mm.

74. The system of claim 10, wherein the PRF is between about 500 Hz to about 75 KHz.

* * * * *